United States Patent [19]

Crews, Jr. et al.

[11] Patent Number: 5,679,791
[45] Date of Patent: Oct. 21, 1997

[54] 1-(3-HETEROCYCLYLPHENYL)-S-TRIAZINE-2,4,6-OXO OR THIOTRIONE HERBICIDAL AGENTS

[75] Inventors: Alvin Donald Crews, Jr., Voorhees; Gary Mitchell Karp, Princeton Junction; Mark Christopher Manfredi, Hamilton; Michael Anthony Guaciaro, Hightstown, all of N.J.

[73] Assignee: American Cyanamid Company, Parsippany, N.J.

[21] Appl. No.: 686,288

[22] Filed: Jul. 25, 1996

[51] Int. Cl.⁶ .................................................. C07D 251/34
[52] U.S. Cl. .......................................................... 544/222
[58] Field of Search ............................................. 544/222

[56] References Cited

U.S. PATENT DOCUMENTS

| 4,512,797 | 4/1985 | Parg et al. | 71/93 |
| 4,876,253 | 10/1989 | Fuhrer et al. | 514/241 |
| 4,927,824 | 5/1990 | Adler et al. | 514/241 |
| 5,356,863 | 10/1994 | Satow et al. | 504/243 |

FOREIGN PATENT DOCUMENTS

| 077938 | 5/1983 | European Pat. Off. . |
| 640600 | 3/1995 | European Pat. Off. . |
| WO85/01939 | 5/1985 | WIPO . |

*Primary Examiner*—John M. Ford
*Attorney, Agent, or Firm*—Gregory M. Hill

[57] ABSTRACT

There is provided a 1-(3-heterocyclylphenyl)-s-triazine-2,4,6-oxo or thiotrione compound having the structural formula I

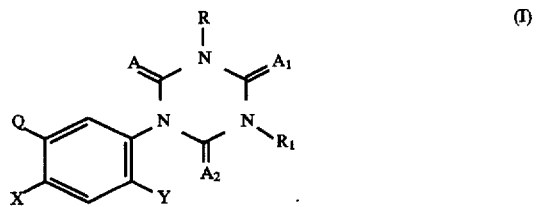

Further provided are a composition and a method comprising that compound for the control of undesirable plant species.

3 Claims, No Drawings

1-(3-HETEROCYCLYLPHENYL)-S-TRIAZINE-2,4,6-OXO OR THIOTRIONE HERBICIDAL AGENTS

BACKGROUND OF THE INVENTION

Weeds cause tremendous global economic losses by reducing crop yields and lowering crop quality. In the United States alone, agronomic crops must compete with hundreds of weed species.

In spite of the commercial herbicides available today, damage to crops caused by weeds still occurs. Accordingly, there is ongoing research to create new and more effective herbicides.

Certain heterocyclylphenyl herbicidal agents are known (see, e.g., WO 85/01939, EP 77938-A2 and U.S. Pat. No. 5,356,863). However, none of those publications disclose heterocyclylphenyl compounds which are substituted with a 1,3,5-triazine-2,4,6-trione group.

Fungicidal 1,3,5-triazine-2,4,6-triones are described in U.S. Pat. No. 4,876,253 and U.S. Pat. No. 4,927,824. However, those patents do not disclose any heterocyclylphenyl substituted 1,3,5-triazine-2,4,6-triones. Further, the patentees do not disclose any herbicidal utility for their compounds.

EP 640600-A1 and U.S. Pat. No. 4,512,797 disclose herbicidal 1,3,5-triazine-2,4,6-triones. However, those publications do not disclose any heterocyclylphenyl substituted 1,3,5-triazine-2,4,6-trione compounds.

It is an object of the present invention to provide compounds which are highly effective for controlling undesirable plant species.

It is also an object of the present invention to provide methods for controlling undesirable plant species.

Those and other objects of the present invention will become more apparent from the detailed description thereof set forth below.

SUMMARY OF THE INVENTION

The present invention describes 1-(3-heterocyclylphenyl)-s-triazine-2,4,6-oxo or thiotrione compounds which are useful as herbicidal agents.

The 1-(3-heterocyclylphenyl)-s-triazine-2,4,6-oxo or thiotrione compounds of the present invention have the structural formula I

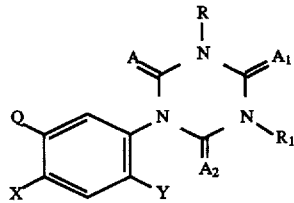

(I)

wherein

X and Y are each independently hydrogen, halogen, nitro, cyano, $C_1$-$C_4$alkyl, $C_1$-$C_4$haloalkyl, $C_1$-$C_4$alkoxy, $C_1$-$C_4$haloalkoxy or $S(O)_mR_2$;

m is an integer of 0, 1 or 2;

$R_2$ is $C_1$-$C_4$alkyl or $C_1$-$C_4$haloalkyl;

R is hydrogen, $C_1$-$C_6$alkyl, $C_2$-$C_{12}$alkoxyalkyl, $C_3$-$C_{12}$alkylcarbonylalkyl, $C_3$-$C_{12}$haloalkylcarbonylalkyl, $C_3$-$C_{12}$alkoxycarbonylalkyl, $C_3$-$C_{12}$haloalkoxycarbonylalkyl, $C_3$-$C_6$alkenyl, $C_3$-$C_6$alkynyl, an alkali metal, phenyl optionally substituted with one to three halogen, $C_1$-$C_4$alkyl, $C_1$-$C_4$alkoxy or $C_1$-$C_4$haloalkoxy groups, or benzyl optionally substituted with one to three halogen, $C_1$-$C_4$alkyl, $C_1$-$C_4$alkoxy or $C_1$-$C_4$haloalkoxy groups;

$R_1$ is hydrogen, $C_3$-$C_6$alkenyl, $C_3$-$C_6$alkynyl, cyano, $C_1$-$C_{12}$alkyl optionally substituted with one or more halogen atoms, or one cyano, $C(O)R_3$, $C(W)R_4$, $OC(O)R_5$, $CH_2OC(O)R_5$, $OR_4$, $CH_2OR_4$ or $CR_6(OR_7)_2$ group, or one phenyl group optionally substituted with one to three halogen, $C_1$-$C_4$alkyl, $C_1$-$C_4$alkoxy or $C_1$-$C_4$haloalkoxy groups, or phenyl optionally substituted with one to three halogen, $C_1$-$C_4$alkyl, $C_1$-$C_4$alkoxy or $C_1$-$C_4$haloalkoxy groups;

$R_3$ is OH, $OR_8$, $SR_8$ or $NR_9R_{10}$;

W is O, $NOR_9$, $NCOR_9$ or $NNHCONH_2$;

$R_4$, $R_5$ and $R_6$ are each independently hydrogen, $C_1$-$C_4$alkyl or $C_1$-$C_4$haloalkyl;

$R_7$ is $C_1$-$C_4$alkyl;

$R_8$ is $C_1$-$C_6$alkyl optionally substituted with $C_1$-$C_4$alkoxy, $C_1$-$C_4$alkylthio, halogen, hydroxy, $C_3$-$C_6$cycloalkyl, furyl or phenyl optionally substituted with one or more halogen, cyano, nitro, $C_1$-$C_4$alkyl, $C_1$-$C_4$haloalkyl, $C_1$-$C_4$alkoxy or $C_1$-$C_4$haloalkoxy groups, $C_3$-$C_6$alkenyl optionally substituted with $C_1$-$C_4$alkoxy, halogen, $C_3$-$C_6$cycloalkyl or phenyl optionally substituted with one or more halogen, cyano, nitro, $C_1$-$C_4$alkyl, $C_1$-$C_4$haloalkyl, $C_1$-$C_4$alkoxy or $C_1$-$C_4$haloalkoxy groups, $C_3$-$C_6$alkynyl optionally substituted with $C_1$-$C_4$alkoxy or halogen, $C_3$-$C_6$cycloalkyl, $N=C(R_4R_5)$, or an alkali metal, alkaline earth metal, manganese, copper, zinc, cobalt, silver, nickel, ammonium or organic ammonium cation;

$R_9$ and $R_{10}$ are each independently hydrogen, $C_1$-$C_6$alkyl, benzyl optionally substituted with one or more halogen, cyano, nitro, $C_1$-$C_4$alkyl, $C_1$-$C_4$haloalkyl, $C_1$-$C_4$alkoxy or $C_1$-$C_4$haloalkoxy groups, or phenyl optionally substituted with one or more halogen, cyano, nitro, $C_1$-$C_4$alkyl, $C_1$-$C_4$haloalkyl, $C_1$-$C_4$alkoxy or $C_1$-$C_4$haloalkoxy groups;

Q is selected from

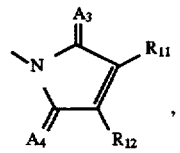

Q1

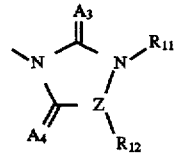

Q2

-continued
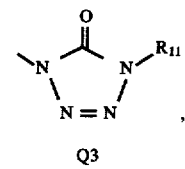  Q3
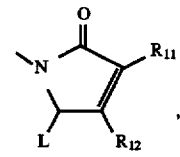  Q4
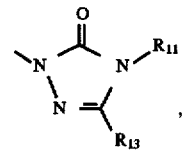  Q5
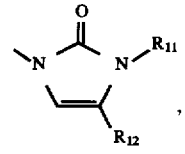  Q6
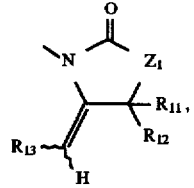  Q7
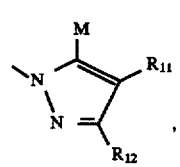  Q8
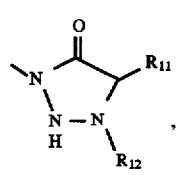  Q9
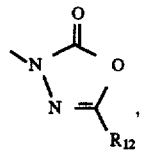  Q10
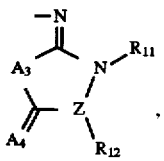  Q11
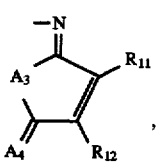  Q12
-continued
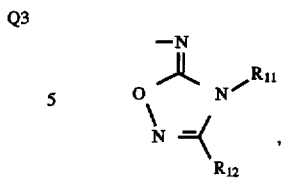  Q13
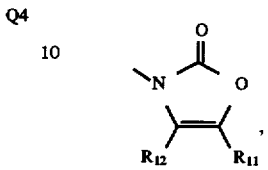  Q14
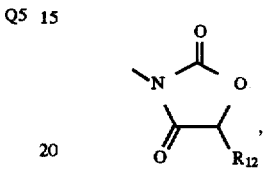  Q15
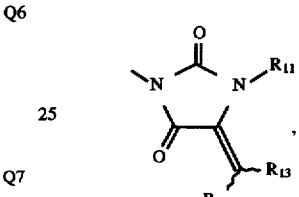  Q16
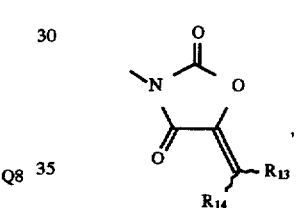  Q17
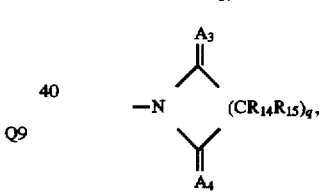  Q18
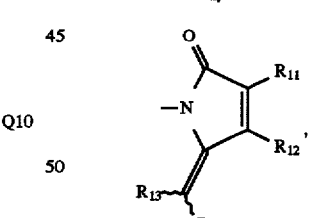  Q19
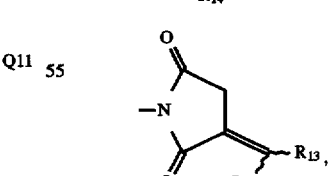  Q20
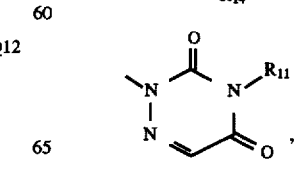  Q21

-continued

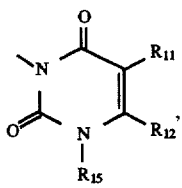
Q22

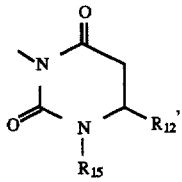
Q23

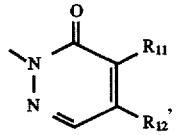
Q24

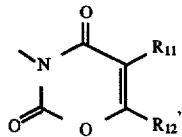
Q25

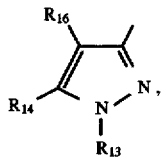
Q26

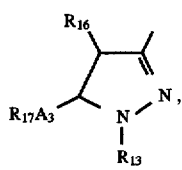
Q27

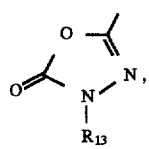
Q28

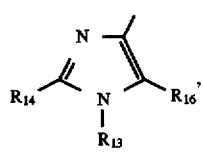
Q29

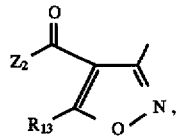
Q30

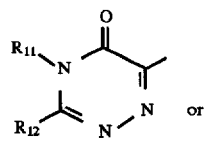
Q31 or

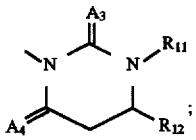
Q32

$R_{11}$ and $R_{12}$ are each independently hydrogen, $C_1$-$C_6$alkyl optionally substituted with one or more halogen atoms, or $C_3$-$C_6$cycloalkyl optionally substituted with one or more halogen atoms, and when $R_{11}$ and $R_{12}$ are taken together with the atoms to which they are attached, they represent a four- to seven-membered saturated or unsaturated ring optionally interrupted by O, S(O)$_r$, or N, and optionally substituted with one to three methyl groups or one or more halogen atoms;

$R_{13}$, $R_{14}$ and $R_{15}$ are each independently hydrogen, $C_1$-$C_3$alkyl or $C_1$-$C_3$haloalkyl;

$R_{16}$ is hydrogen or halogen;

$R_{17}$ is $C_1$-$C_4$alkyl or $C_1$-$C_4$haloalkyl;

A, $A_1$, $A_2$, $A_3$ and $A_4$ are each independently O or S;

L is hydroxy, halogen, $C_1$-$C_3$alkoxy or $C_1$-$C_3$alkylthio;

M is halogen or $C_1$-$C_3$alkyl;

Z is N or CH;

$Z_1$ is $NR_9$ or O;

$Z_2$ is $OR_7$ or $NR_9R_{10}$;

r is an integer of 0, 1 or 2; and q is an integer of 2, 3 or 4.

This invention also relates to compositions containing those compounds and methods for using those compounds and compositions. Advantageously, it has been found that the compounds of the present invention, and compositions containing them, are useful for the control of undesirable plant species. The compounds of the present invention are especially useful for the selective control of undesirable plant species in the presence of crops.

DETAILED DESCRIPTION OF THE INVENTION

The present invention provides a method for controlling undesirable plant species which comprises applying to the foliage of said plants or to the soil or water containing seeds or other propagating organs thereof, a herbicidally effective amount of a formula I, 1-(3-heterocyclylphenyl)-s-triazine-2,4,6-oxo or thiotrione compound.

The 1-(3-heterocyclylphenyl)-s-triazine-2,4,6-oxo or thiotrione compounds of the present invention have the structural formula I

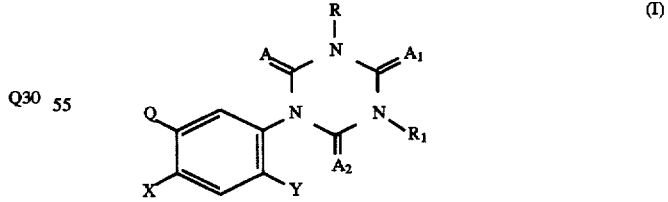
(I)

wherein X, Y, R, $R_1$, A, $A_1$, $A_2$ and Q are as described above.

Preferred formula I compounds of this invention are those wherein

X is hydrogen or halogen;

Y is hydrogen, halogen, nitro or cyano;

R is hydrogen, $C_1$-$C_4$alkyl, $C_1$-$C_4$alkoxymethyl, ($C_1$-$C_4$alkoxy)carbonylmethyl, $C_3$-$C_6$alkenyl or $C_3$-$C_6$alkynyl;

$R_1$ is hydrogen, $C_3$–$C_6$alkenyl, $C_3$–$C_6$alkynyl or $C_1$–$C_6$alkyl optionally substituted with one $C(O)R_3$ group;

$R_3$ is OH or $OR_8$;

$R_8$ is $C_1$–$C_6$alkyl or an alkali metal, ammonium or organic ammonium cation;

Q is selected from

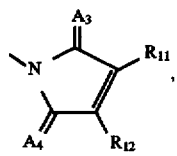 Q1

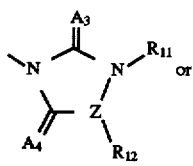 Q2

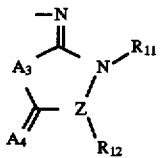 Q11

$R_{11}$ and $R_{12}$ are taken together with the atoms to which they are attached to form a ring in which $R_{11}R_{12}$ is a $C_2$–$C_5$alkylene group optionally interrupted by $S(O)_r$, and optionally substituted with one to three methyl groups or one or more halogen atoms, or $R_{11}R_{12}$ is represented by the structure: —$CR_{18}$=$CR_{19}$—$CR_{20}$=$CR_{21}$— where $R_{18}$, $R_{19}$, $R_{20}$ and $R_{21}$ are each independently hydrogen, halogen or methyl;

A, $A_1$ and $A_2$ are O;

$A_3$ and $A_4$ are each independently O or S;

Z is N or CH; and r is an integer of 0, 1 or 2.

More preferred formula I herbicidal agents of the present invention are those wherein X and Y are each independently hydrogen, F or Cl;

R is hydrogen, $C_1$–$C_4$alkyl, $C_1$–$C_4$alkoxymethyl, ($C_1$–$C_4$alkoxy)carbonylmethyl, allyl or propargyl;

$R_1$ is allyl, propargyl or $C_1$–$C_4$alkyl optionally subsituted with one $C(O)R_3$ group;

$R_3$ is OH or $OR_8$;

$R_8$ is $C_1$–$C_6$alkyl;

Q is selected from

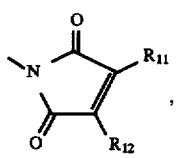

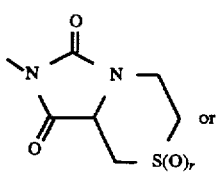 or

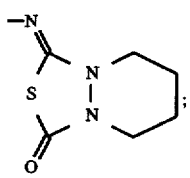

$R_{11}$ and $R_{12}$ are taken together with the atoms to which they are attached to form a ring in which $R_{11}R_{12}$ is a butylene group optionally substituted with one to three methyl groups;

A, $A_1$ and $A_2$ are O; and r is an integer of 0 or 1.

Most preferred formula I compounds of this invention which are especially useful for the control of undesirable plant species are those wherein X is F or Cl;

Y is Cl;

R is $C_1$–$C_4$alkyl, allyl or propargyl;

$R_1$ is $CH_2CO_2R_8$;

$R_8$ is $C_1$–$C_4$alkyl;

Q is

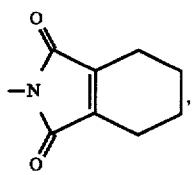

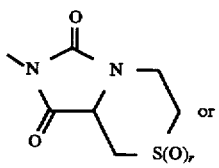 or

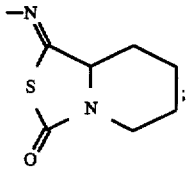

A, $A_1$ and $A_2$ are O; and r is an integer of 0 or 1.

1-(3-Heterocyclylphenyl)-s-triazine-2,4,6-oxotrione compounds of the present invention which are particularly effective herbicidal agents include:

isopropyl 3-{2-chloro-4-fluoro-5-[5,6,8,8a-tetrahydro-1,3-dioxo-1H-imidazo[5,1-c][1,4]thiazin-2(3H)-yl]phenyl}tetrahydro-5-methyl-2,4,6-trioxo-s-triazine-1(2H)-acetate;

isopropyl 3-{2-chloro-4-fluoro-5-[(tetrahydro-3-oxo-1H,3H-[1,3,4]thiadiazolo[3,4-a]pyridazin-1-ylidene)amino]phenyl}tetrahydro-5-methyl-2,4,6-trioxo-s-triazine-1(2H)-acetate;

isopropyl 3-[2-chloro-4-fluoro-5-(tetrahydro-1,3,7-trioxo-1H-imidazo[5,1-c][1,4]thiazin-2(3H)-yl)phenyl]tetrahydro-5-methyl-2,4,6-trioxo-s-triazine-1(2H)-acetate;

isopropyl 3-[2-chloro-4-fluoro-5-(3-fluorophthalimido)phenyl]tetrahydro-5-methyl-2,4,6-trioxo-s-triazine-1(2H)-acetate;

tert-butyl 3-[2-chloro-5-(1-cyclohexene-1,2-dicarboximido)-4-fluorophenyl]tetrahydro-5-methyl-2,4,6-trioxo-s-triazine-1(2H)-acetate;

isopropyl 3-[2-chloro-5-(1-cyclohexene-1,2-dicarboximido)-4-fluorophenyl]tetrahydro-5-methyl-2,4,6-trioxo-s-triazine-1(2H)-acetate; and methyl 3-[2-chloro-5-(1-cyclohexene-1,2-dicarboximido)-4-fluorophenyl]tetrahydo-5-methyl-2,4,6-trioxo-s-triazine-1(2H)-acetate, among others Exemplary of halogen hereinabove are flourine, chlorine, bromine and iodine. The terms $C_1$–$C_4$haloalkyl, $C_1$–$C_3$haloalkyl, and $C_1$–$C_4$haloalkoxy as used in the specification and claims designates a $C_1$–$C_4$alkyl group, a $C_1$–$C_3$alkyl group or a $C_1$–$C_4$alkoxy group substituted with one or more halogen atoms, respectively. In formula I above, alkali metals include: sodium, potassium and lithium. Alkaline earth metals of formula I include magnesium and calcium. Further, the term organic ammonium is defined as a group consisting of a positively charged nitrogen atom joined to from one to four aliphatic groups, each containing from one to sixteen carbon atoms.

It has now been found that the compounds of the present invention are especially useful for the selective control of undesirable plant species in the presence of important agronomic crops.

Formula I compounds wherein Q is Q1 may be prepared by reducing a 3-(3-nitrophenyl)-s-triazine-2,4,6-oxo or thiotrione of formula II by standard conditions such as catalytic hydrogenation or chemical reduction to form an amine of formula III, and reacting the formula III amine with an anhydride of formula IV, preferably at an elevated temperature in the presence of an acid such as acetic acid to form the formula I compound wherein $R_1$ is hydrogen, and optionally alkylating the formula I compound wherein $R_1$ is hydrogen with an alkylating agent of formula V and a base to form the formula I compound wherein $R_1$ is other than hydrogen. The reactions are shown in Flow Diagram I.

FLOW DIAGRAM I

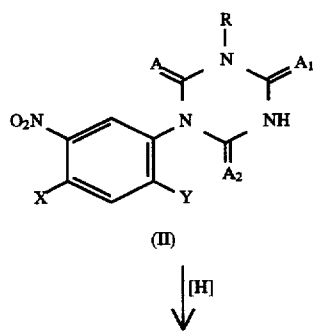

-continued
FLOW DIAGRAM I

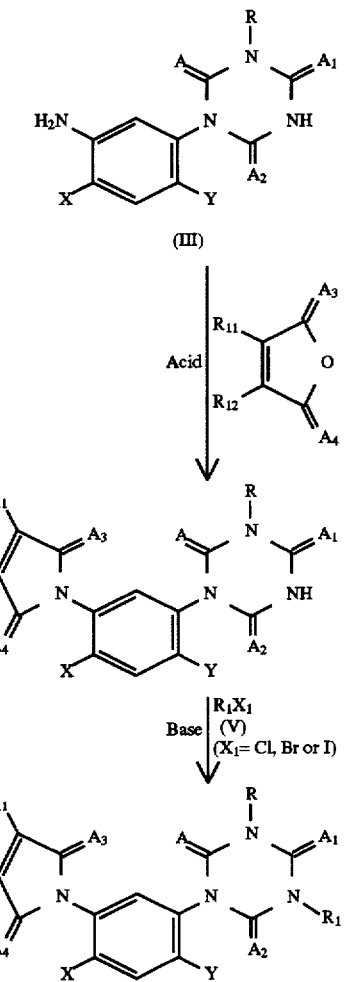

Alternatively, formula I compounds wherein Q is Q1 and $R_1$ is other than hydrogen and may be prepared by alkylating a 3-(3-nitrophenyl)-s-triazine-2,4,6-oxo or thiotrione of formula II with an alkylating agent of formula V and a base to form a 3-(3-nitrophenyl)-s-triazine-2,4,6-oxo or thiotrione of formula VI, reducing the formula VI compound by standard conditions to form an amine of formula VII, and reacting the formula VII amine with an anhydride of formula IV, preferably at an elevated temperature, in the presence of an acid such as acetic acid. The reaction scheme is shown in Flow Diagram II.

FLOW DIAGRAM II

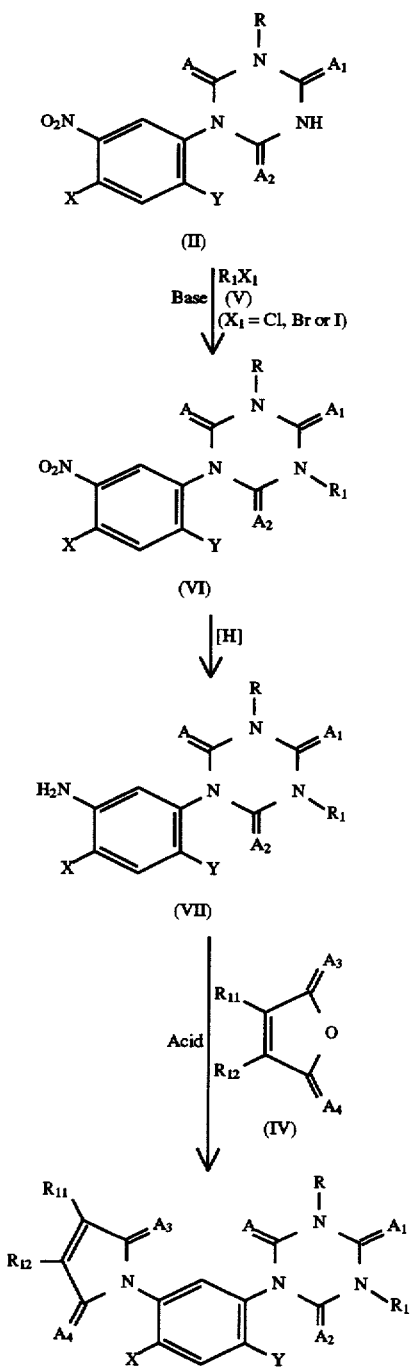

Formula I compounds wherein Q is Q2 and Z is CH may be prepared by reacting an amine of formula VII with phosgene or thiophosgene in the presence of an inert solvent to form an isocyanate or thioisocyanate of formula VIII, reacting the formula VIII isocyanate or thioisocyanate with an aminoester of formula IX in the presence of a base such as triethylamine to form an intermediate compound, and cyclizing the intermediate compound with an acid or base in the presence of an inert organic solvent such as ethanol. The reactions are shown in Flow Diagram III.

FLOW DIAGRAM III

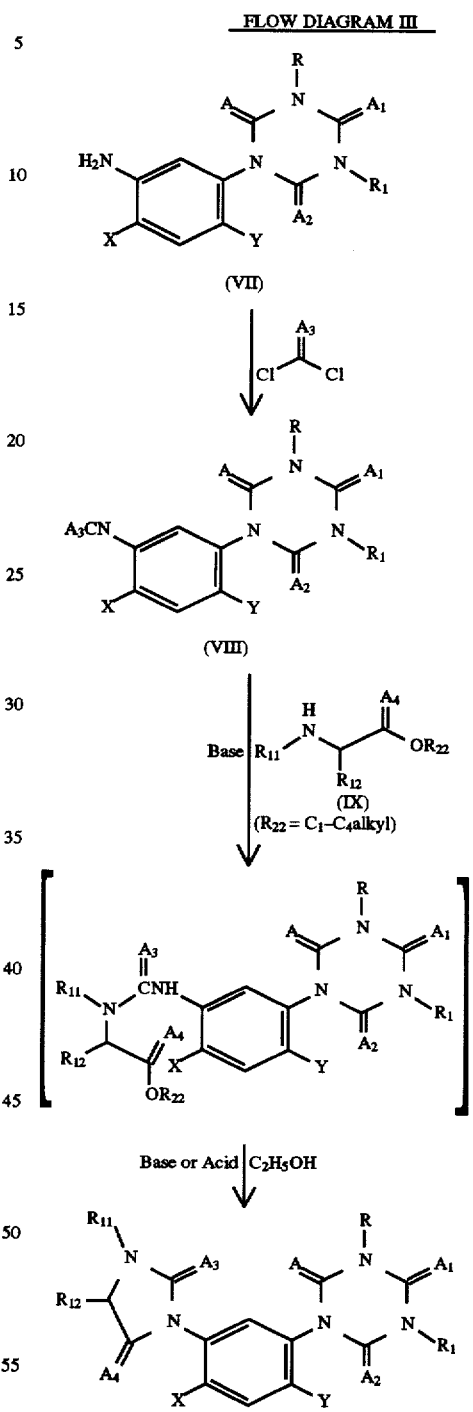

Compounds of formula I wherein Q is Q2 and Z is nitrogen may be prepared by reacting an isocyanate or thioisocyanate of formula VIII with a substituted hydrazine of formula X to form an intermediate compound, and cyclizing the intermediate compound with base. The reaction scheme is shown below in Flow Diagram IV.

FLOW DIAGRAM IV

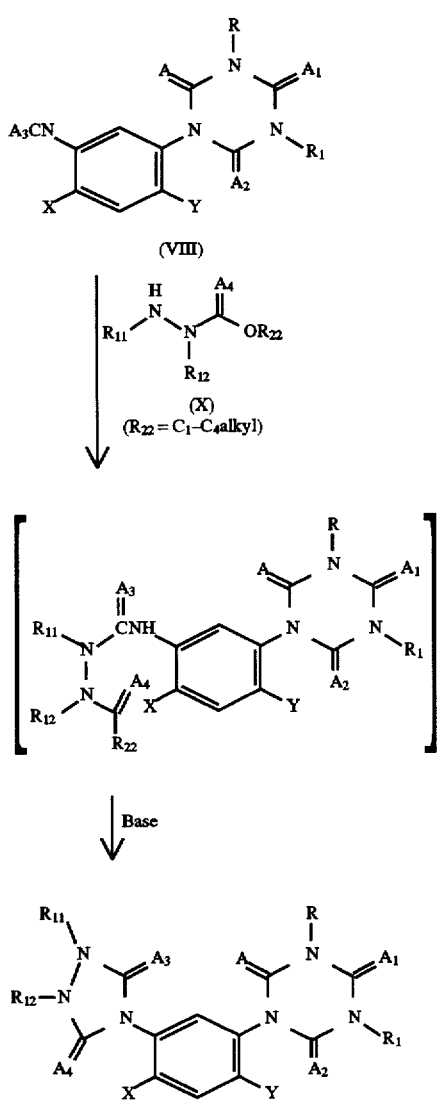

Formula I compounds wherein Q is Q3 may be prepared by reacting an amine of formula III with sodium nitrite, sodium azide, acetic acid, hydrochloric acid and sodium acetate or with sodium nitrite, hydrazine hydrate and acetic acid to form an azide of formula XI, and reacting the formula XI azide with an isocyanate of formula XII to form the desired formula I compound wherein $R_1$ is hydrogen, and optionally alkylating the formula I compound wherein $R_1$ is hydrogen with an alkylating agent of formula V and a base. The reactions are shown in Flow Diagram V.

FLOW DIAGRAM V

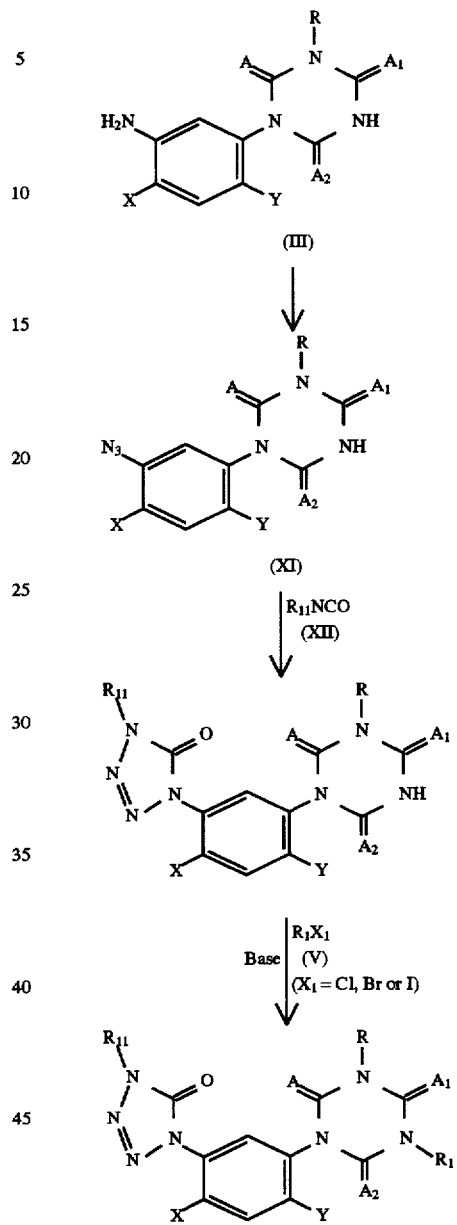

Compounds of formula I wherein Q is Q4 may be prepared by reacting a compound of formula I wherein Q is Q1 and $A_3$ and $A_4$ are oxygen with sodium borohydride to form a compound wherein L is OH, reacting the compound wherein L is OH with a base and a suitable alkylating agent to form a compound wherein L is $C_1-C_3$alkoxy or reacting the compound wherein L is OH with a halogenating agent such as phosphorus trichloride, thionyl chloride, phosphorus tribromide, triphenyl phosphine-bromine, phosphorus triiodide or triphenyl phosphine-iodine in an inert solvent such as chloroform to form a compound wherein L is halogen and further reacting the compound wherein L is halogen with a $C_1$-$C_3$alkyl sulfide to form a compound wherein L is $C_1$-$C_3$alkylthio. The above reaction schemes are shown below in Flow Diagram VI.

to form an amidrazone of formula XVI, and reacting the amidrazone with phosgene or a suitable phosgene equivalent optionally in the presence of triethylamine to form the desired compound. The reactions are shown in Flow Diagram VII.

FLOW DIAGRAM VI

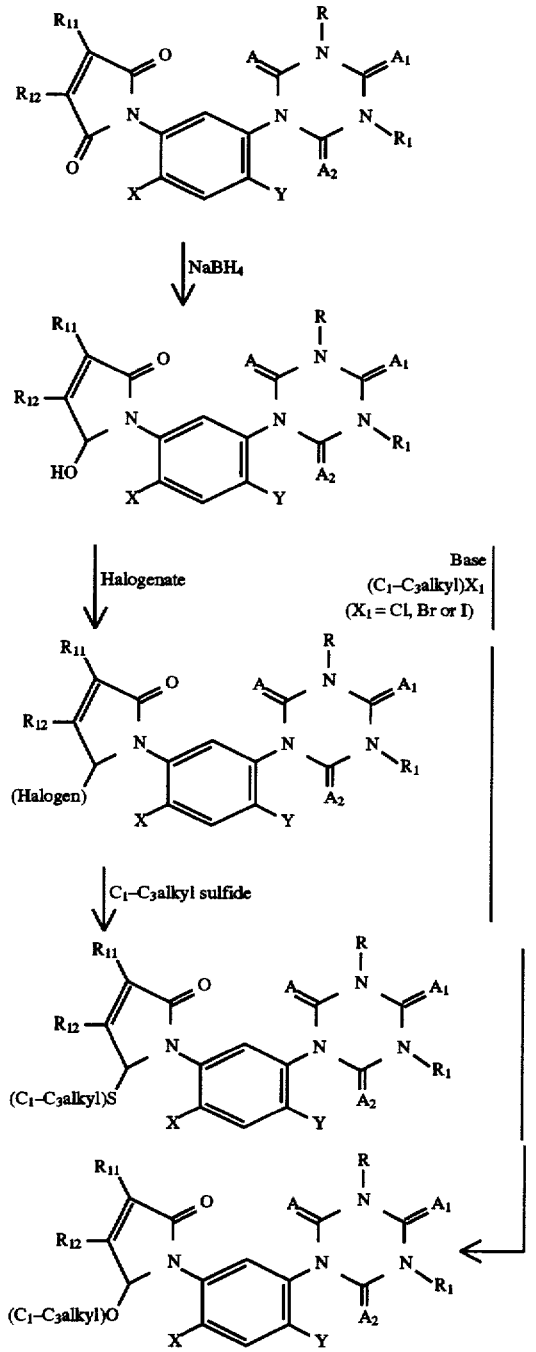

FLOW DIAGRAM VII

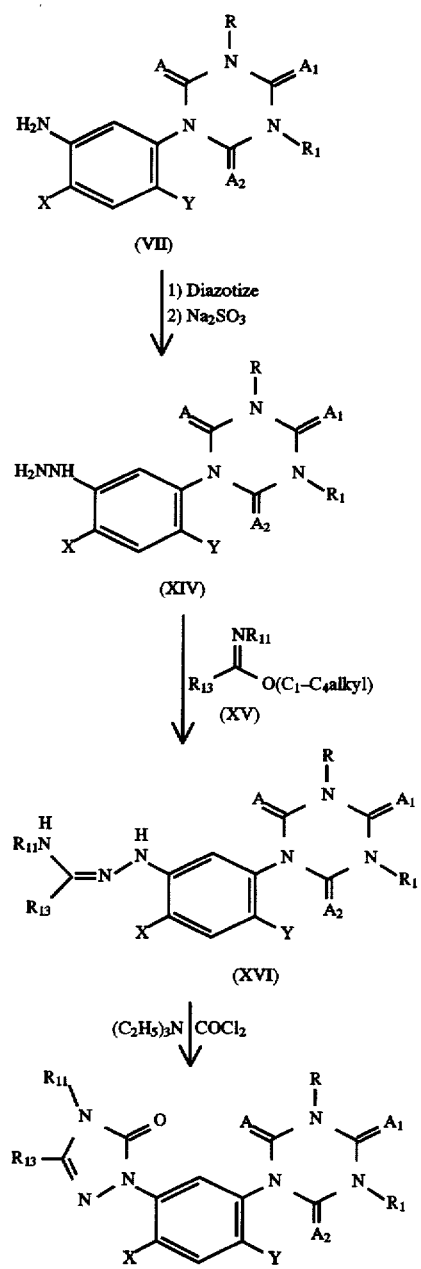

Formula I compounds wherein Q is Q5 may be prepared by diazotizing an amine of formula VII by standard methods to form an intermediate compound which is reduced with sodium sulfite to form a hydrazine of formula XIV. The hydrazine is then reacted with an imino ether of formula XV Compounds of formula I wherein Q is Q6 may be prepared by condensing an amine of formula VII with a β-aminoaldehyde of formula XVII in the presence of a base to form an intermediate compound, and reacting the intermediate compound with phosgene or a phosgene equivalent. The reactions are shown in Flow Diagram VIII.

FLOW DIAGRAM VIII

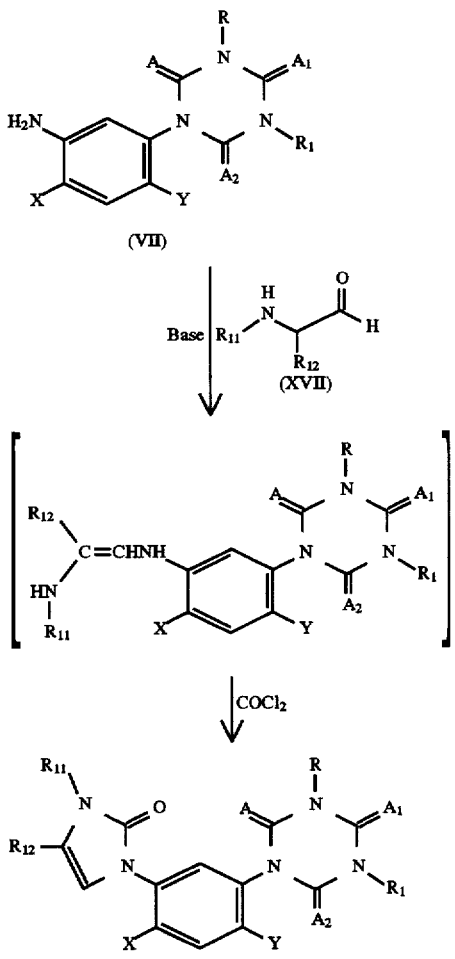

Formula I compounds wherein Q is Q7 may be prepared by reacting an isocyanate of formula VIII with a substituted alkyne of formula XVIII in the presence of a base, optionally at an elevated temperature. The reaction is shown in Flow Diagram IX.

FLOW DIAGRAM IX

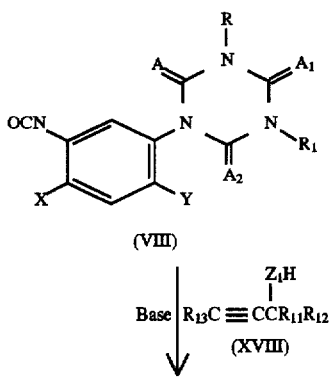

-continued
FLOW DIAGRAM IX

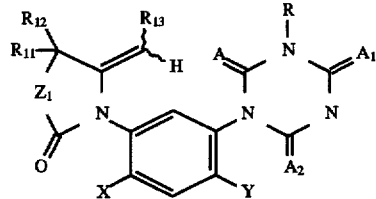

Formula I compounds wherein Q is Q8 and M is halogen may be prepared by reacting a hydrazine of formula XIV or its hydrochloride salt with a 2-alkoxycarbonylalkanone of formula XIX optionally in the presence of a base such as triethylamine or sodium acetate in an inert solvent such as ethanol or toluene to form a 2,3-dihydropyrazol-3-one of formula XX, and halogenating the formula XX compound with a halogenating agent such as phosphorus oxychloride or phosphorus oxybromide. The reactions are shown in Flow Diagram X.

FLOW DIAGRAM X

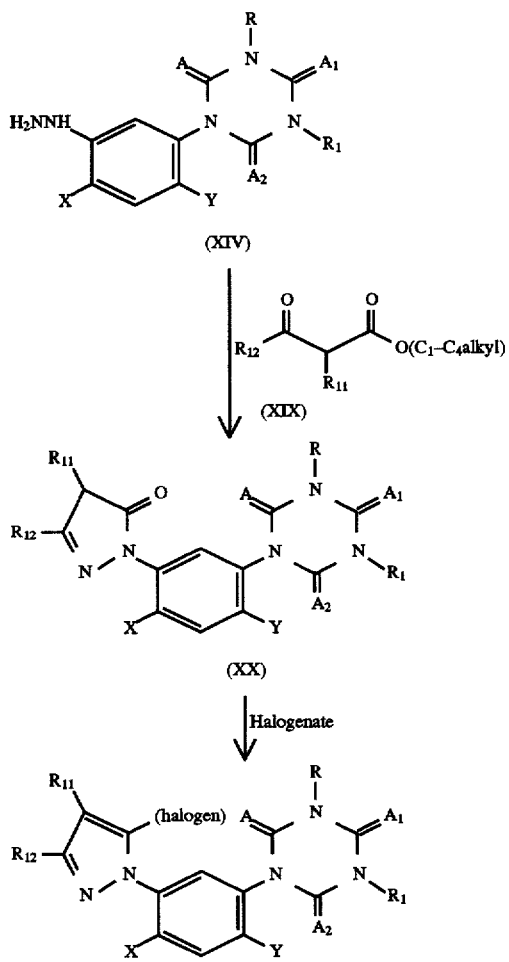

Formula I compounds wherein Q is Q8 and M is $C_1$-$C_3$alkyl may be prepared by reacting a hydrazine of formula XIV with a 1,3-diketone of formula XXI optionally in the presence of a base in an inert solvent. The reaction is shown below in Flow Diagram XI.

FLOW DIAGRAM XI

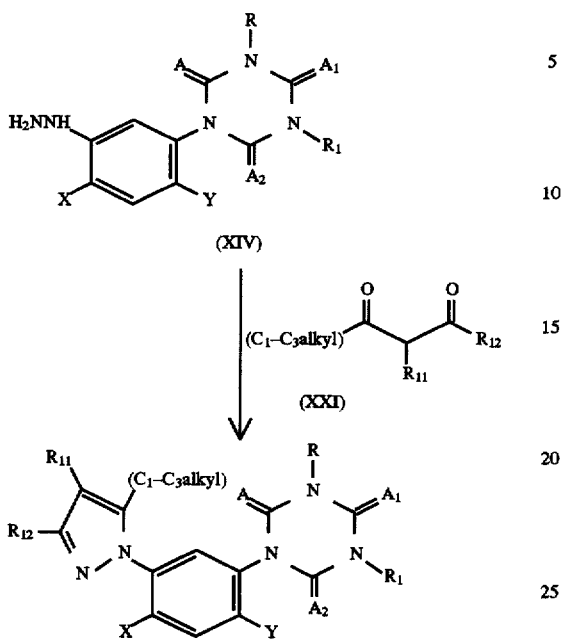

Compounds of formula I wherein Q is Q9 may be prepared by diazotizing an amine of formula VII to form an intermediate diazonium salt and reacting the intermediate salt in situ with a β-aminoacid of formula XXII in the presence of triethylamine. The reaction scheme is shown below in Flow Diagram XII.

FLOW DIAGRAM XII

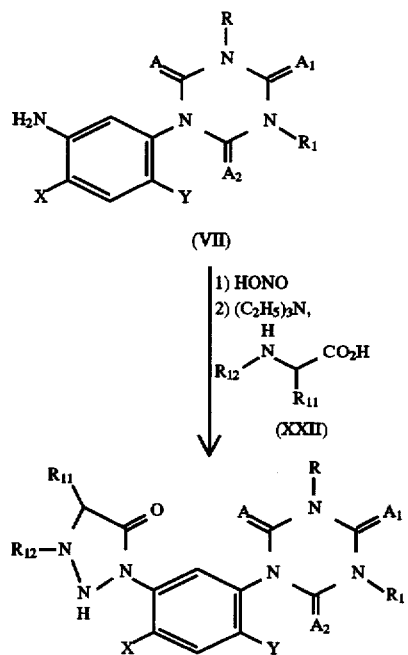

Compounds of formula I wherein Q is Q10 may be prepared by reacting a hydrazine of formula XIV with an acyl halide of formula XXIII in the presence of a base such as triethylamine or pyridine to form an aryl hydrazide of formula XXIV, and reacting the aryl hydrazide with trichloromethyl chloroformate, phosgene or a suitable phosgene equivalent optionally in the presence of triethylamine. The reaction scheme is shown in Flow Diagram XIII.

FLOW DIAGRAM XIII

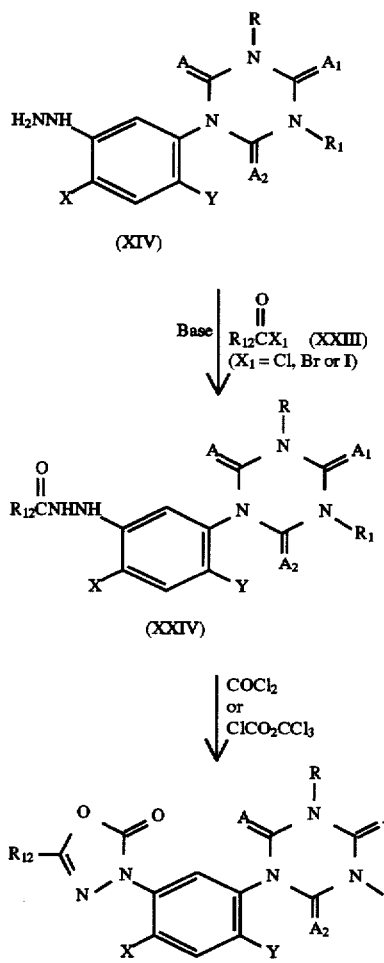

Formula I compounds wherein Q is Q11, $A_3$ is sulfur, $A_4$ is oxygen and Z is CH may be prepared by reacting an isothiocyanate of formula VIII with an amine of formula XXV to form a thiourea of formula XXVI and reacting the thiourea with an α-halocarbonyl halide of formula XXVII in the presence of a base. The reactions are shown in Flow Diagram XIV.

FLOW DIAGRAM XIV

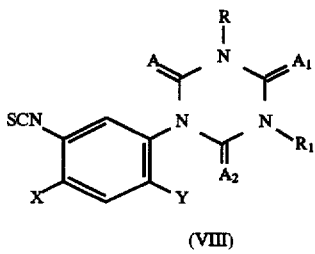

21
-continued
FLOW DIAGRAM XIV

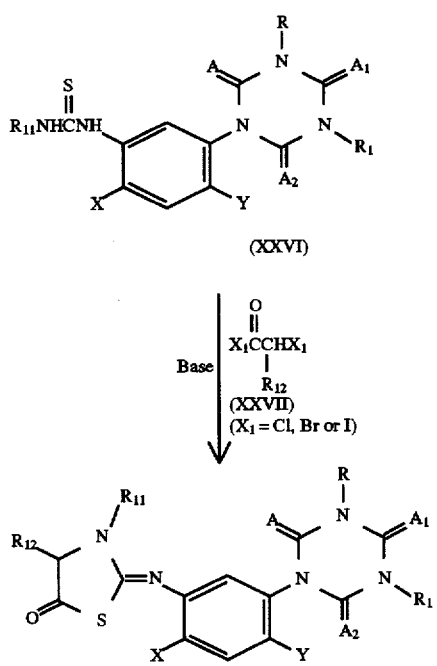

(XXVI)

Formula I compounds wherein Q is Q11, $A_3$ is sulfur, $A_4$ is oxygen and Z is nitrogen may be prepared by reacting an isothiocyanate of formula VIII with a substituted hydrazine of formula XXVIII to form an intermediate compound of formula XXIX and reacting the intermediate compound with phosgene or a suitable phosgene equivalent in the presence of a base such as triethylamine. The reaction sequence is shown in Flow Diagram XV.

FLOW DIAGRAM XV

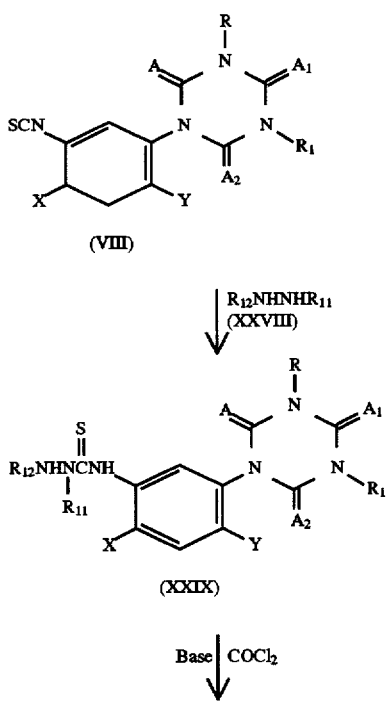

22
-continued
FLOW DIAGRAM XV

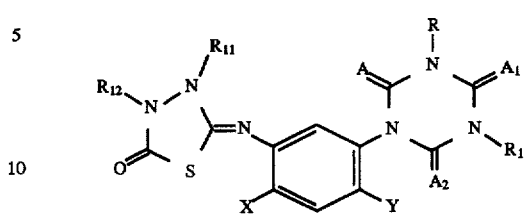

Compounds of formula I wherein Q is Q11, $A_3$ and $A_4$ are oxygen and Z is CH may be prepared by reacting an isocyanate of formula VIII with an amine of formula XXV to form a urea of formula XXX, dehydrating the urea to form a carbodiimide of formula XXXI, reacting the carbodiimide with an α-halocarbonyl halide of formula XXVII to form a haloamidine of formula XXXII, hydrolyzing the haloamidine with aqueous acid to form an acylurea, heating the acylurea in situ to form an O-acylurea of formula XXXIII, and reacting the O-acylurea with a base such as triethylamine. The reactions are shown below in Flow Diagram XVI.

FLOW DIAGRAM XVI

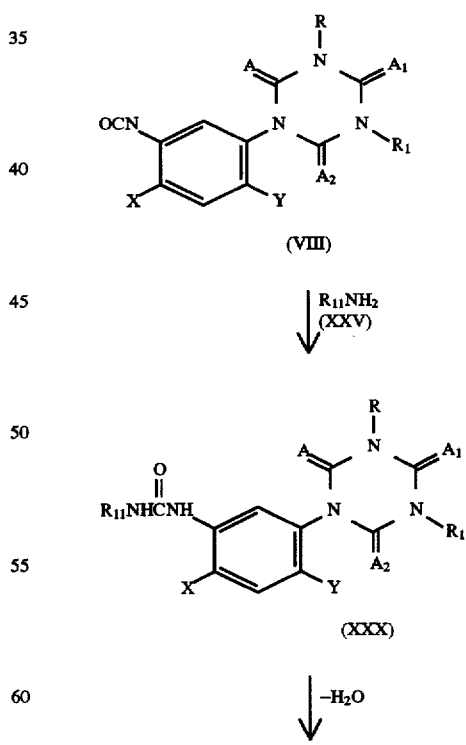

-continued
FLOW DIAGRAM XVI

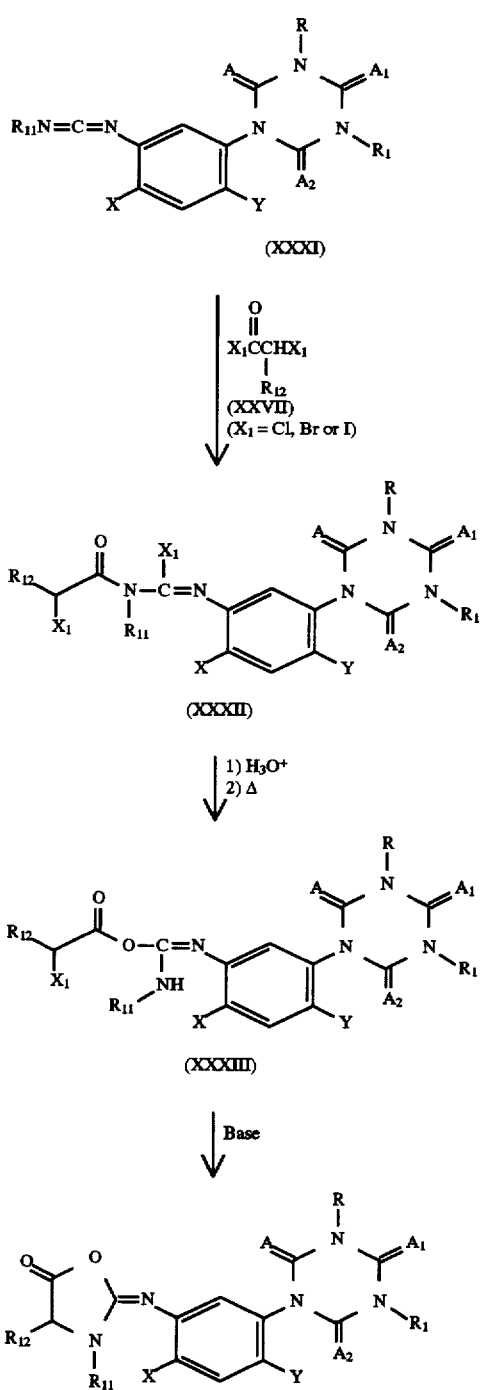

Formula I compounds wherein Q is Q12 may be prepared by reacting an amine of formula VII with an anhydride of formula IV to form an acid-amide of formula XXXIV, and dehydrating the acid-amide with a dehydrating agent such as 1,3-dicyclohexylcarbodiimide. The reaction scheme is shown below in Flow Diagram XVII.

FLOW DIAGRAM XVII

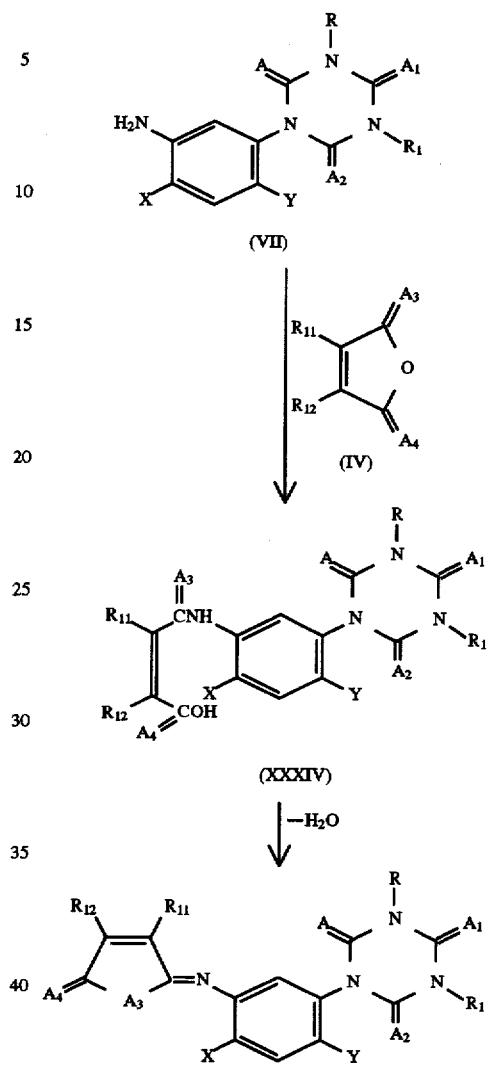

Compounds of formula I wherein Q is Q13 may be prepared by reacting a thiourea of formula XXVI with iodomethane to form an isothiourea of formula XXXV and reacting the isothiourea with a chlorooxime of formula XXXVI. The reaction scheme is shown in Flow Diagram XVIII.

FLOW DIAGRAM XVIII

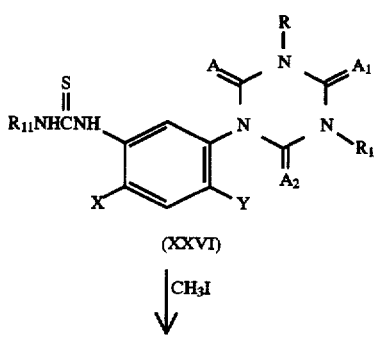

FLOW DIAGRAM XVIII -continued

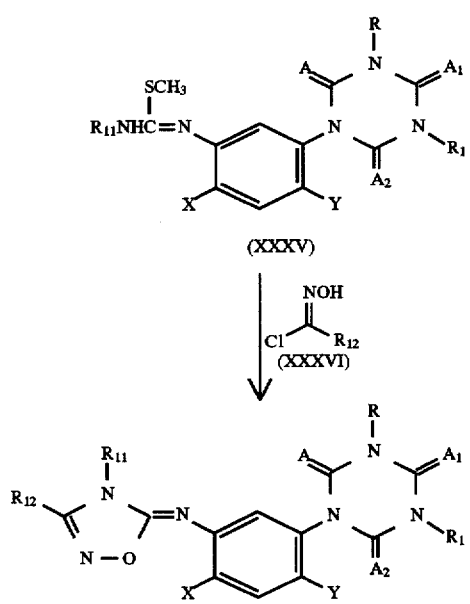

Formula I compounds wherein Q is Q14 may be prepared by reacting an amine of formula VII with a chloroformate of formula XXXVII to form a carbamate of formula XXXVIII, and reacting the carbamate with a haloketone of formula XXXIX in the presence of a base. The reaction scheme is shown below in Flow Diagram XIX.

FLOW DIAGRAM XIX

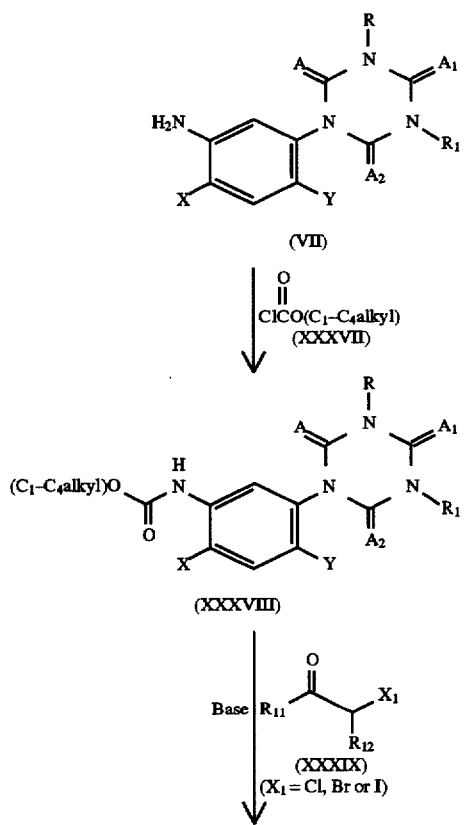

FLOW DIAGRAM XIX -continued

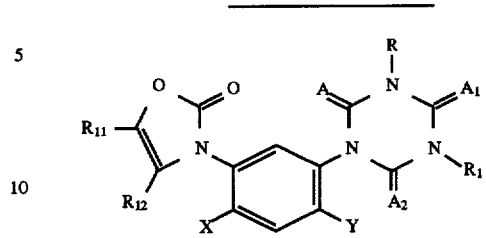

Compounds of formula I wherein Q is Q15 may be prepared by reacting an amine of formula VII with ethyl chloroformate to form a carbamate of formula XL, and reacting the carbamate with a hydroxy ester of formula XLI at an elevated temperature with removal of ethanol. The reactions are shown in Flow Diagram XX.

FLOW DIAGRAM XX

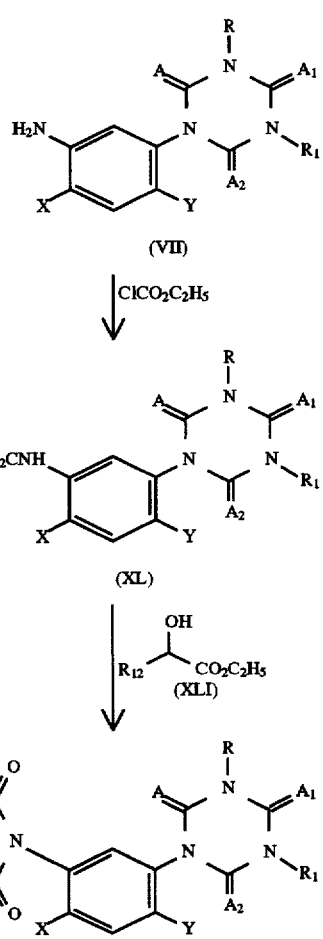

Alternatively, compounds of formula I wherein Q is Q15 may be prepared by reacting an isocyanate of formula VIII with a hydroxy ester of formula XLII to form an intermediate compound of formula XLIII, and reacting the intermediate compound with a base such as sodium acetate in an inert solvent such as toluene. The reaction scheme is shown below in Flow Diagram XXI.

FLOW DIAGRAM XXI

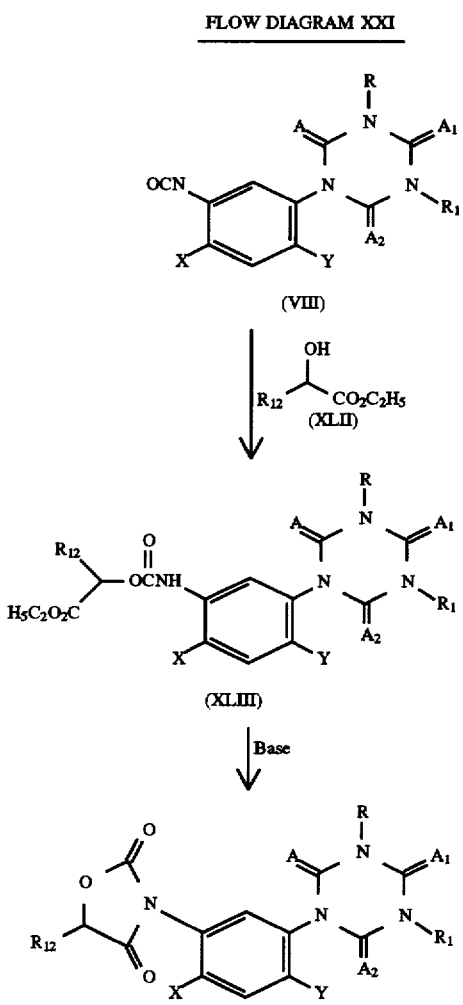

Formula I compounds wherein Q is Q16 may be prepared by reacting an isocyanate of formula VIII with an α-amino-α,β-unsaturated ester of formula XLIV to form a urea of formula XLV, and reacting the urea with a base such as sodium acetate in an inert solvent such as toluene at an elevated temperature. The reactions are shown in Flow Diagram XXII.

FLOW DIAGRAM XXII

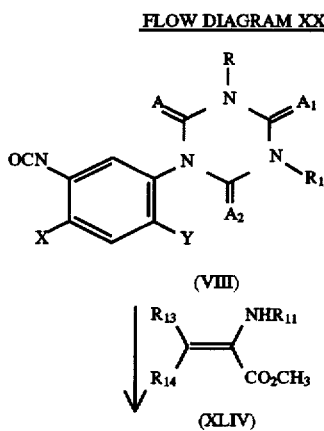

FLOW DIAGRAM XXII -continued

Alternatively, formula I compounds wherein Q is Q16 may be prepared by reacting an isocyanate of formula VIII with an amino acid of formula XLVI to form a urea of formula XLVII, reacting the urea with aqueous acid to form a hydantoin of formula XLVIII, and reacting the hydantoin with an acetal of formula XLIX. The reaction scheme is shown below in Flow Diagram XXIII.

FLOW DIAGRAM XXIII

-continued
FLOW DIAGRAM XXIII

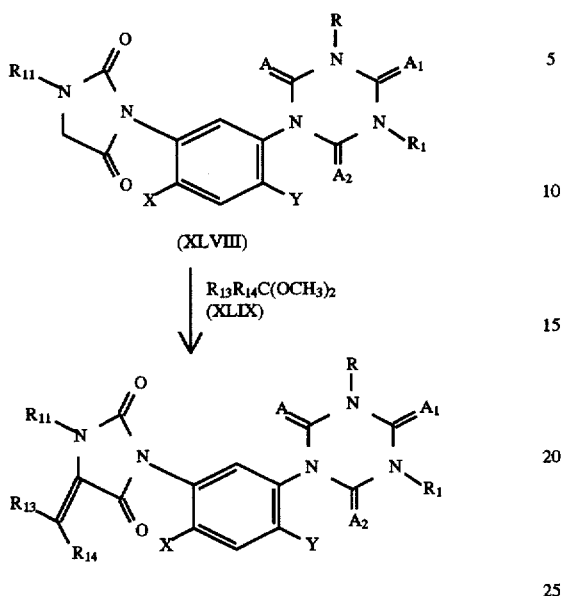
(XLVIII)

Compounds of formula I wherein Q is Q17 may be prepared by reacting an isocyanate of formula VIII with a hydroxy alkenoate of formula L in the presence of a base such as triethylamine. The reaction is shown in Flow Diagram XXIV.

FLOW DIAGRAM XXIV

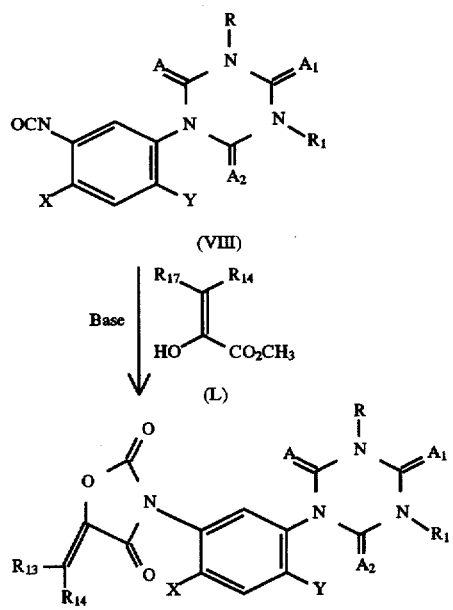

Compounds of formula I wherein Q is Q18 may be prepared by reacting an amine of formula VII with an anhydride of formula LI in the presence of an acid such as acetic acid preferably at an elevated temperature. The reaction is shown below in Flow Diagram XXV.

FLOW DIAGRAM XXV

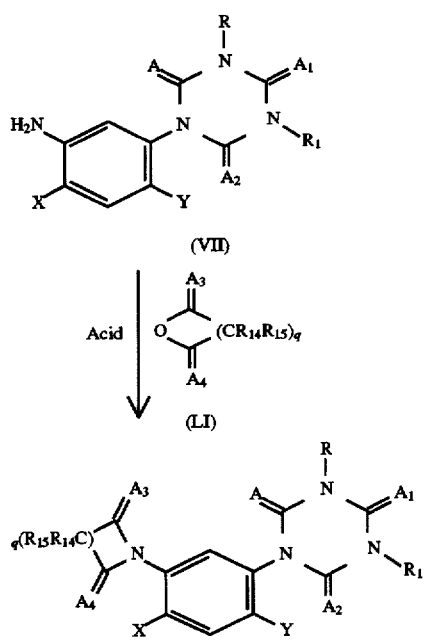

Formula I compounds wherein Q is Q19 may be prepared by reacting a formula I compound wherein Q is Q1, $A_3$ and $A_4$ are oxygen and $R_1$ is hydrogen with a Grignard Reagent of formula LII in a solvent such as diethyl ether or tetrahydrofuran at an elevated temperature to form an intermediate compound of formula LIII, and reacting the intermediate compound with potassium bisulfate at an elevated temperature to form the desired formula I compound wherein $R_1$ is hydrogen, and optionally alkylating the formula I compound wherein $R_1$ is hydrogen with an alkylating agent of formula V in the presence of a base. The reactions are shown in Flow Diagram XXVI.

FLOW DIAGRAM XXVI

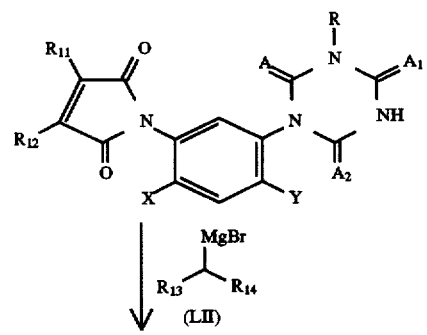

-continued
FLOW DIAGRAM XXVI

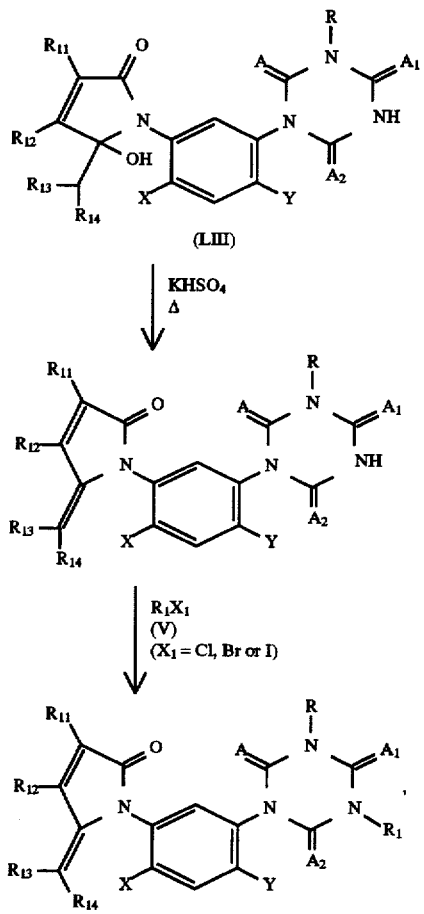

(LIII)

Formula I compounds wherein Q is Q20 may be prepared by reacting an amine of formula VII with an anhydride of formula LIV in acetic anhydride with a catalytic amount of sodium acetate at an elevated temperature, in acetic acid at an elevated temperature or in xylene with a catalytic amount of p-toluene sulfonic acid at an elevated temperature. The reaction is shown below in Flow Diagram XXVII.

FLOW DIAGRAM XXVII

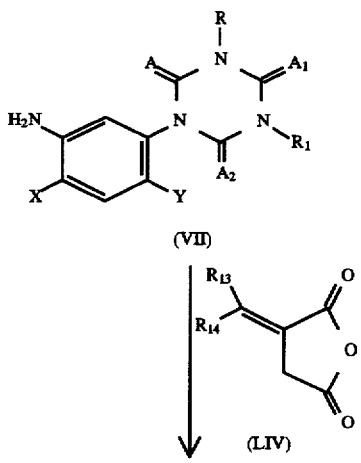

-continued
FLOW DIAGRAM XXVII

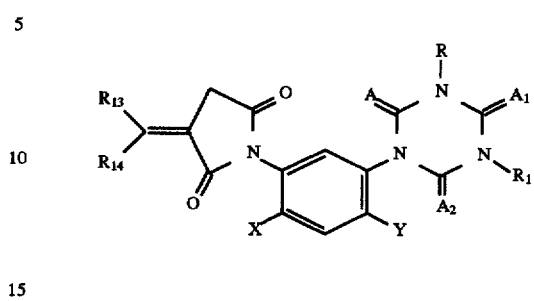

Alternatively, formula I compounds wherein Q is Q20 may be prepared by reacting an amine of formula VII with a diacid of formula LV in xylene at reflux. The reaction is shown in Flow Diagram XXVIII.

FLOW DIAGRAM XXVIII

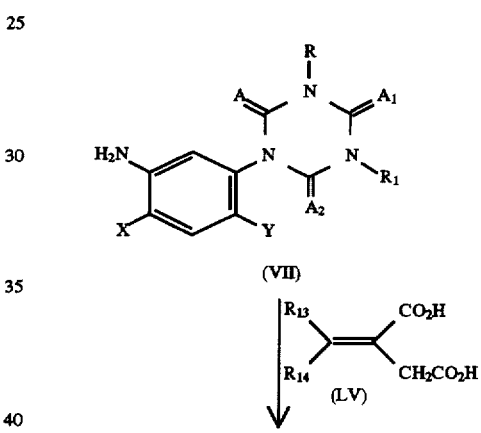

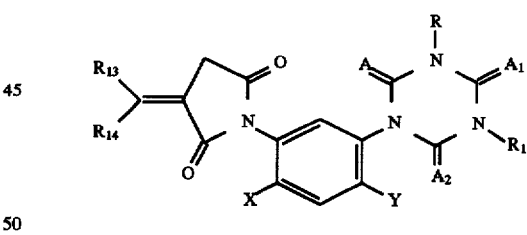

Compounds of formula I wherein Q is Q21 may be prepared by reacting an amine of formula VII with ethyl malonyldiurethane and sodium nitrite in acetic acid with a catalytic amount of concentrated hydrochloric acid to form a hydrazone of formula LVI, cyclizing the hydrazone with base to form a triazinedione of formula LVII, and decarboxylating the triazinedione with mercaptoacetic acid at an elevated temperature and optionally alkylating the formula I compound wherein Q is Q21 and $R_{11}$ is hydrogen with an alkyl halide and a base such as sodium hydride. The reactions are shown in Flow Diagram XXIX.

FLOW DIAGRAM XXIX

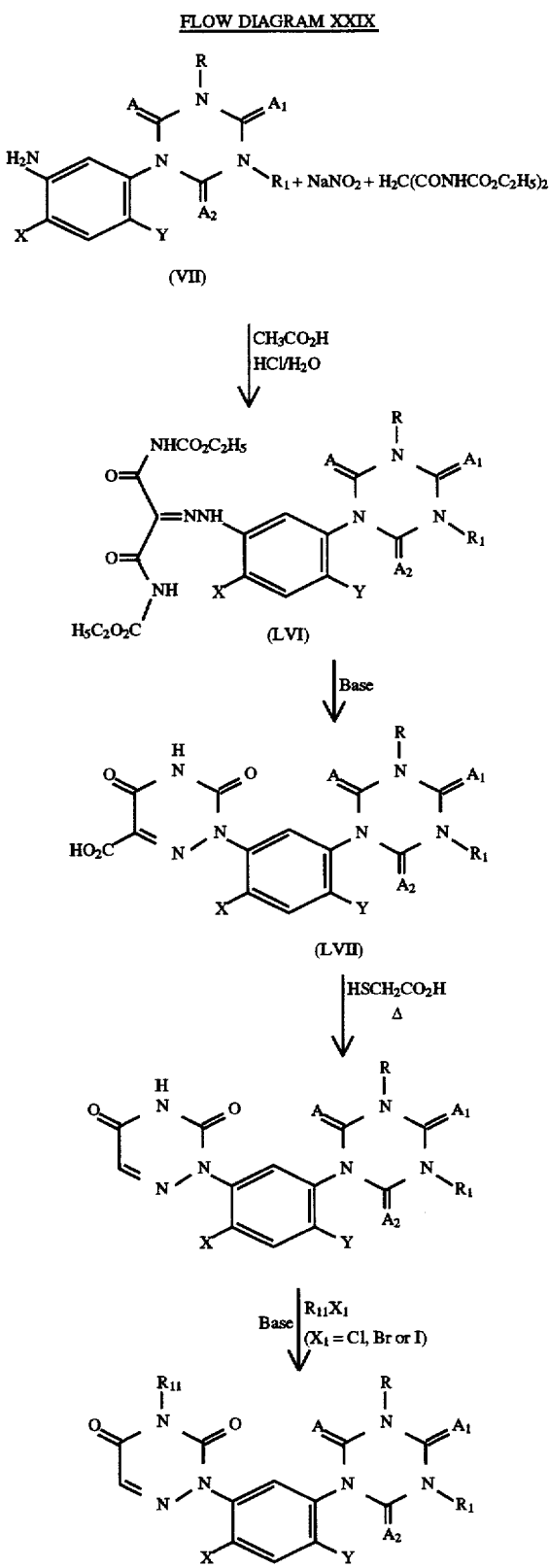

Alternatively, compounds of formula I wherein Q is Q21 and $R_{11}$ is hydrogen may be prepared by reacting a hydrazine of formula XIV with acetone in a sulfuric acid solution to form a hydrazone of formula LVIII, reacting the hydrazone with potassium cyanate in an acetic acid solution to form a triazolidine of formula LIX, and reacting the triazolidine with glyoxylic acid and sulfuric acid.

FLOW DIAGRAM XXXI

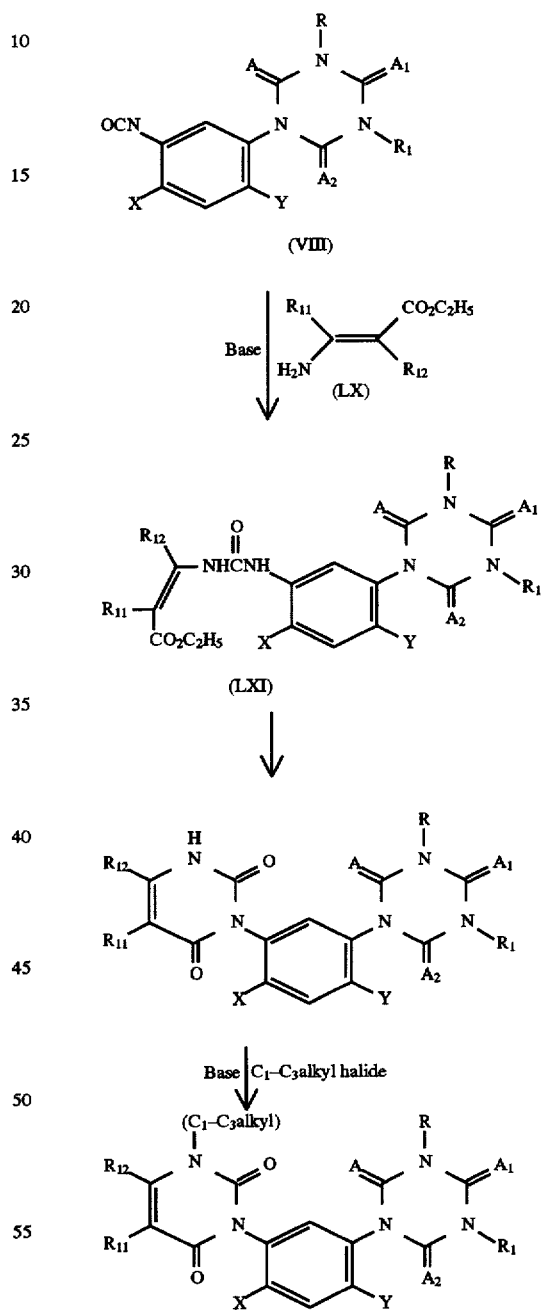

Formula I compounds wherein Q is Q23 may be prepared by reacting an amine of formula LXII with an α,β-unsaturated ester of formula LXIII to form an amino ester of formula LXIV, and reacting the amino ester with an isocyanate of formula VIII followed by heating under acidic conditions. The reaction sequence is shown below in Flow Diagram XXXII.

FLOW DIAGRAM XXXII

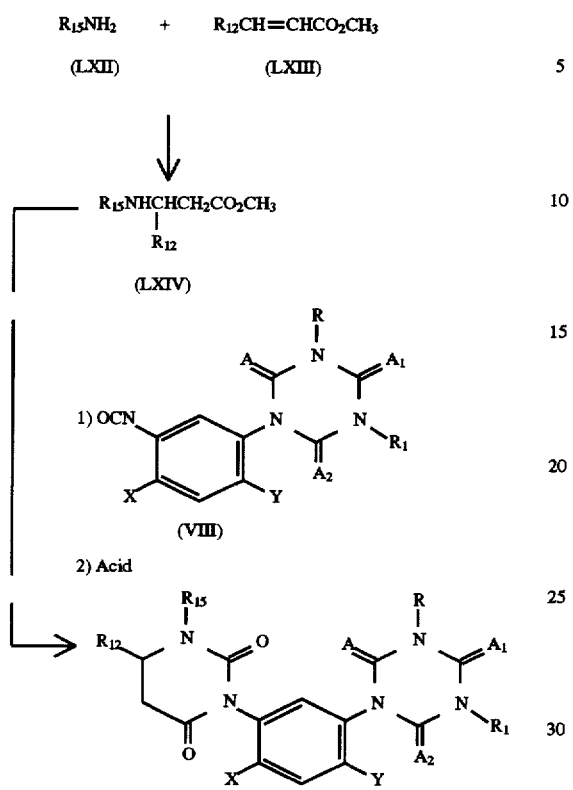

Compounds of formula I wherein Q is Q24 may be prepared by reacting a hydrazine of formula XIV with a formylpropionate of formula LXV followed by cyclization under acidic conditions to form a dihydropyridazinone of formula LXVI, and dehydrogenating the dihydropyridazinone with chloranil or 2,3-dichloro-5,6-dicyanobenzoquinone (DDQ) in an inert solvent such as dioxane or toluene at an elevated temperature. The reactions are shown in Flow Diagram XXXIII.

FLOW DIAGRAM XXXIII

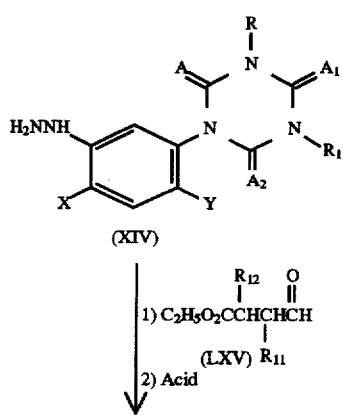

-continued
FLOW DIAGRAM XXXIII

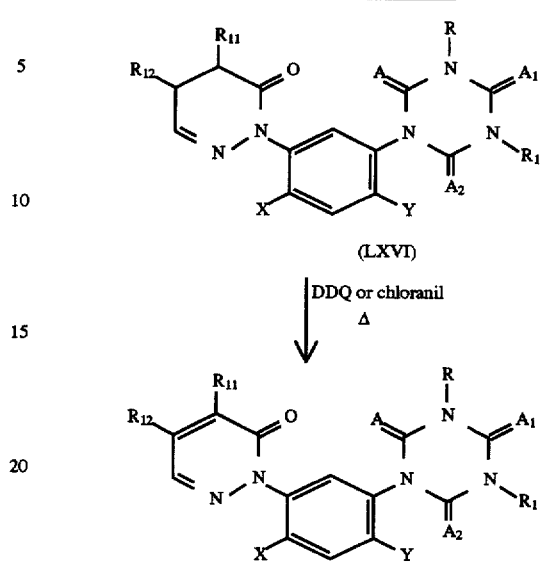

Compounds of formula I wherein Q is Q25 may be prepared by reacting an isocyanate of formula VIII with an acetonide of formula LXVII at an elevated temperature. The reaction is shown in Flow Diagram XXXIV.

FLOW DIAGRAM XXXIV

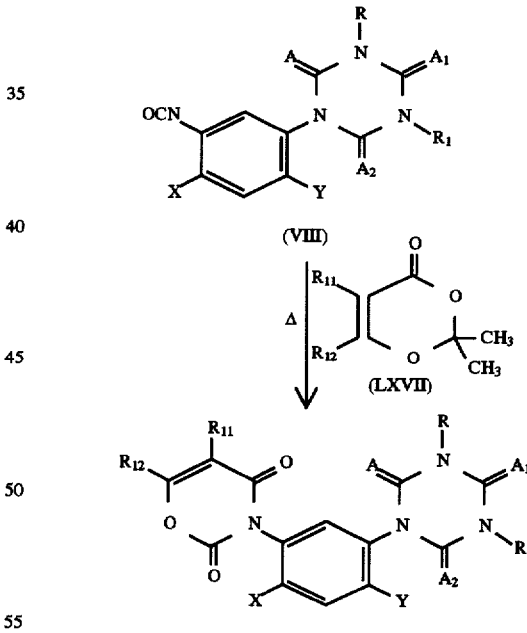

Formula I compounds wherein Q is Q26 may be prepared by reacting a 3-(substituted phenyl)-s-triazine-2,4,6-oxo or thiotrione of formula LXVIII with acetyl chloride in the presence of aluminum chloride to form a ketone of formula LXIX, reacting the ketone with an ester of formula LXX to form a diketone compound of formula LXXI, and reacting the diketone compound with a hydrazine of formula LXXII to form the formula I compound wherein Q is Q26 and $R_{16}$ is hydrogen, and optionally halogenating the formula I compound wherein Q is Q26 and $R_{16}$ is hydrogen. The reactions are shown below in Flow Diagram XXXV.

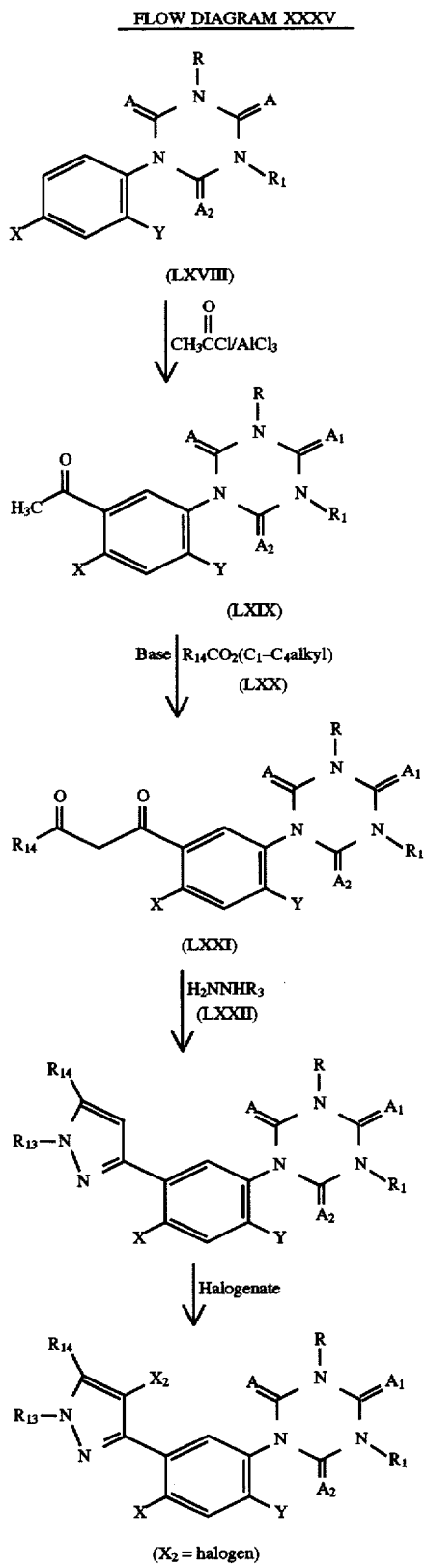

Compounds of formula I wherein Q is Q27 may be prepared by reacting a ketone of formula LXIX with a carbonate or thiocarbonate of formula LXXIII in the presence of a base to form an ester or thioxoester of formula LXXIV, reacting the ester or thioxoester with a hydrazine of formula LXXII to form an intermediate compound of formula LXXV, and alkylating the intermediate compound with an alkylating agent of formula LXXVI in the presence of a base to form the formula I compound wherein Q is Q27 and $R_{16}$ is hydrogen, and optionally halogenating the formula I compound wherein Q is Q27 and $R_{16}$ is hydrogen. The reaction scheme is shown in Flow Diagram XXXVI.

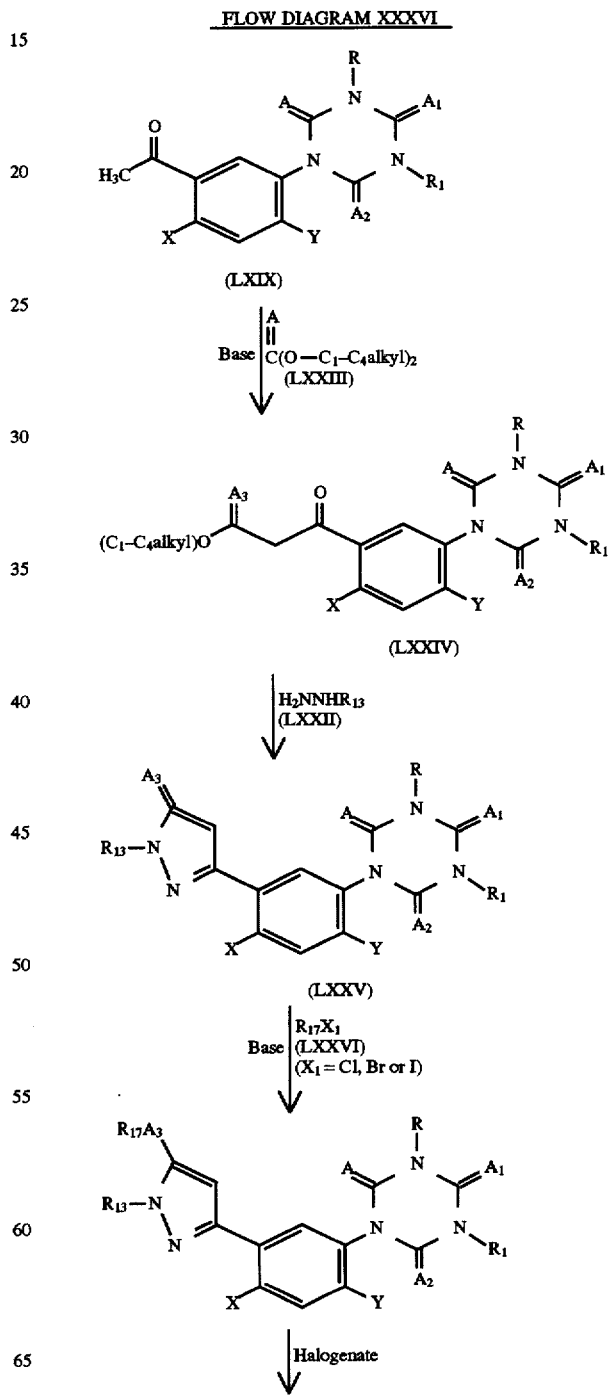

-continued
FLOW DIAGRAM XXXVI

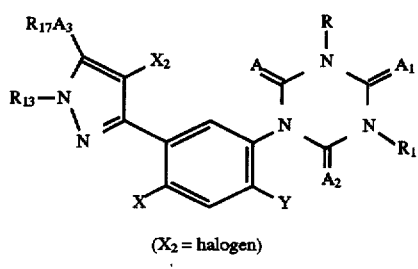

($X_2$ = halogen)

Formula I compounds wherein Q is Q28 may be prepared by reacting an aniline of formula LXXVII with an isocyanate or isothiocyanate of formula LXXVIII to form a urea or thiourea of formula LXXIX, cyclizing the urea or thiourea with an isocyanate or thioisocyanate of formula LXXX to form a 3-(substituted phenyl)-s-triazine-2,4,6-oxo or thiotrione of formula LXXXI, reacting the 3-(substituted phenyl)-s-triazine-2,4,6-oxo or thiotrione sequentially with base, thionyl chloride and a hydrazine of formula LXXII to form an intermediate compound of formula LXXXII, and reacting the intermediate compound with phosgene or a phosgene equivalent to form the formula I compound wherein Q is Q28 and $R_1$ is hydrogen, and optionally alkylating the formula I compound wherein Q is Q28 and $R_1$ is hydrogen with an alkylating agent of formula V in the presence of a base. The reactions are shown in Flow Diagram XXXVII.

FLOW DIAGRAM XXXVII

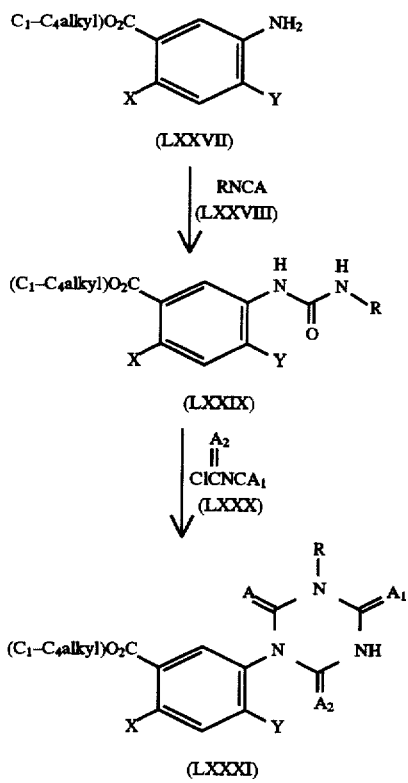

-continued
FLOW DIAGRAM XXXVII

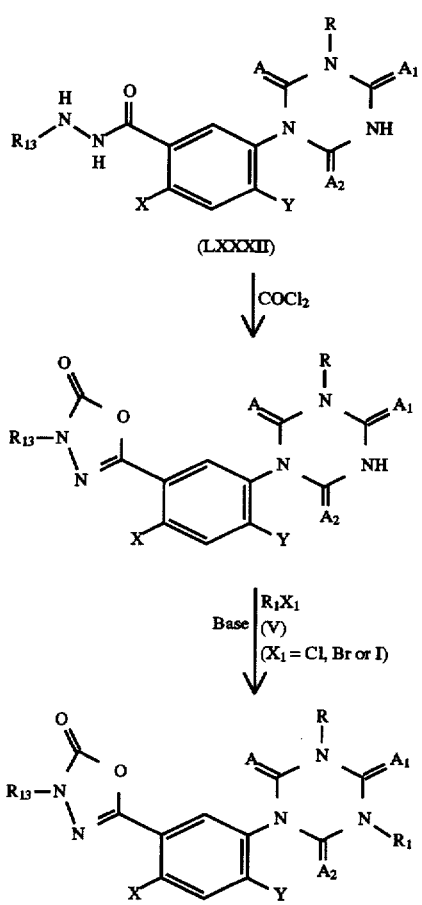

Compounds of formula I wherein Q is Q29 may be prepared by reacting a ketone of formula LXIX with an amidine of formula LXXXIII to form a formula I compound wherein Q is Q29 and $R_{16}$ is hydrogen, and optionally halogenating the formula I compound wherein Q is Q29 and $R_{16}$ is hydrogen. The reaction scheme is shown in Flow Diagram XXXVIII.

FLOW DIAGRAM XXXVIII

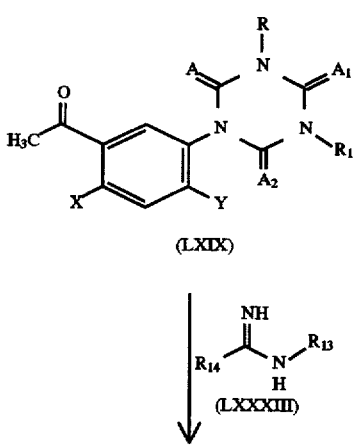

-continued
FLOW DIAGRAM XXXVIII

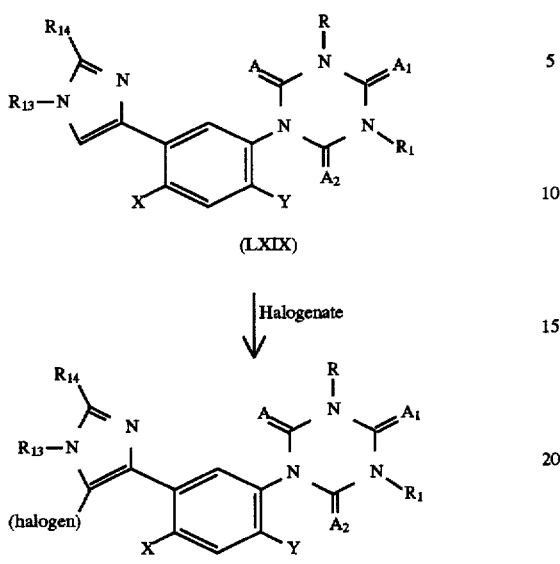

Formula I compounds wherein Q is Q30 and $R_1$ is hydrogen may be prepared by reacting an amine of formula LXXXIV with an isocyanate or thioisocyanate of formula LXXVIII to form a urea or thiourea of formula LXXXV, cyclizing the urea or thiourea with an isocyanate or isothiocyanate of formula LXXX to form a 3-(substituted phenyl)-s-triazine-2,4,6-oxo or thiotrione of formula LXXXVI, reacting the 3-(substituted phenyl)-s-triazine-2,4,6-oxo or thiotrione sequentially with ammonium hydroxide and a chlorinating agent to form a chlorooxime of formula LXXXVII, and reacting the chlorooxime with an alkyne of formula LXXXVIII to obtain a formula I compound wherein Q is Q30, $R_1$ is hydrogen and $Z_2$ is $C_1$–$C_4$alkoxy, and optionally reacting that compound sequentially with acid or base, thionyl chloride and an amine of formula LXXXIX to obtain a formula I compound wherein Q is Q30, $R_1$ is hydrogen and $Z_2$ is $NR_9R_{10}$. The reactions are shown in Flow Diagram XXXIX.

FLOW DIAGRAM XXXIX

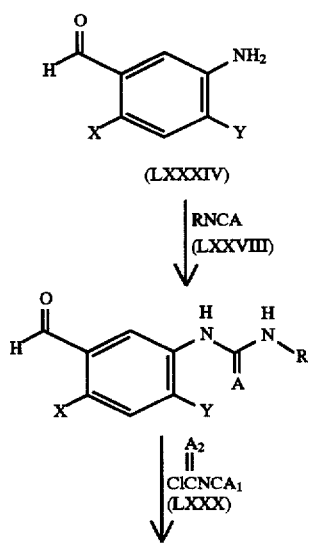

-continued
FLOW DIAGRAM XXXIX

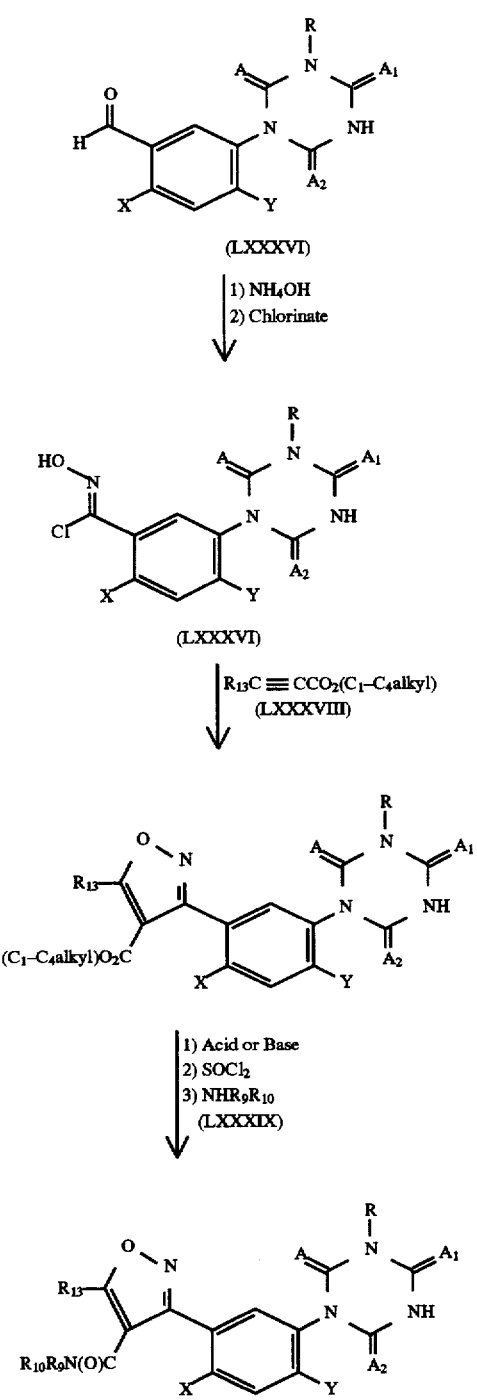

Compounds of formula I wherein Q is Q30 and $R_1$ is other than hydrogen may be prepared by alkylating a formula I compound wherein Q is Q30 and $R_1$ is hydrogen with an alkylating agent of formula V in the presence of a base. The reaction is shown in Flow Diagram XL.

FLOW DIAGRAM XL

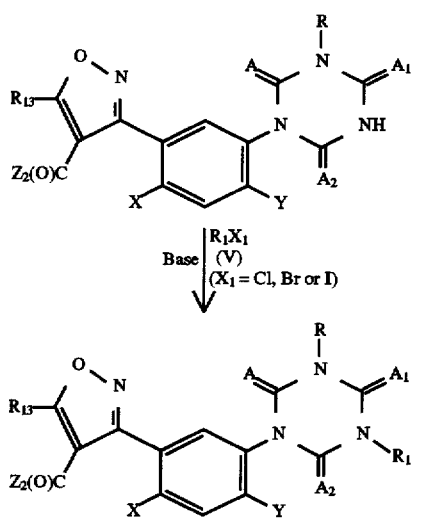

Formula I compounds wherein Q is Q31 may be prepared by reacting a 3-(substituted phenyl)-s-triazine-2,4,6-oxo or thiotrione of formula LXVIII with an ester of formula XC in the presence of aluminum chloride to form an intermediate compound of formula XCI, and reacting the intermediate compound with a substituted amine of formula XCII. The reaction scheme is shown in Flow Diagram XLI.

FLOW DIAGRAM XLI

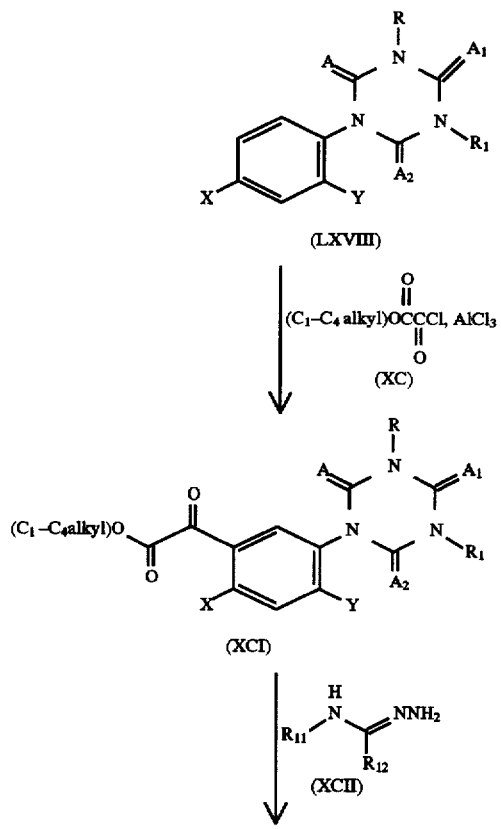

FLOW DIAGRAM XLI —continued

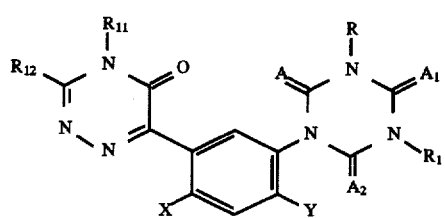

Compounds of formula I wherein Q is Q32 may be prepared by reacting an isocyanate or thioisocyanate of formula VIII with an aminoester or aminothionoester of formula XCIII in an inert solvent preferably at an elevated temperature. The reaction is shown in Flow Diagram XLII.

FLOW DIAGRAM XLII

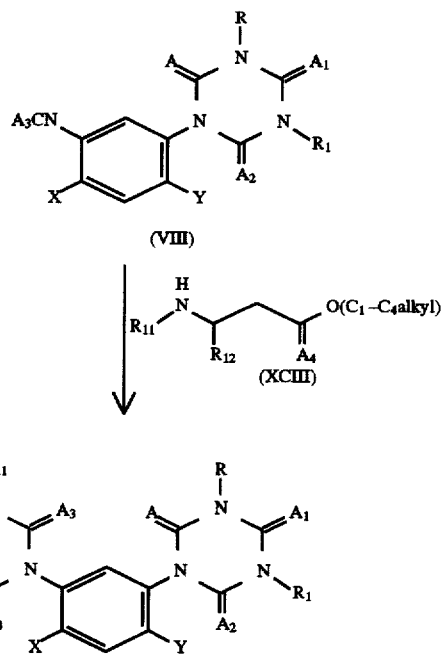

Compounds of formula I wherein $R_3$ is $NR_9R_{10}$ may be prepared using standard procedures such as hydrolyzing the appropriate ester of formula XCIV in the presence of trifluoroacetic acid, reacting the resultant acid with thionyl chloride to give the acid chloride of formula XCV, and reacting the formula XCV acid chloride with an amine of formula LXXXIX optionally in the presence of base to give the desired product. The reactions are shown in Flow Diagram XLIII.

FLOW DIAGRAM XLIII

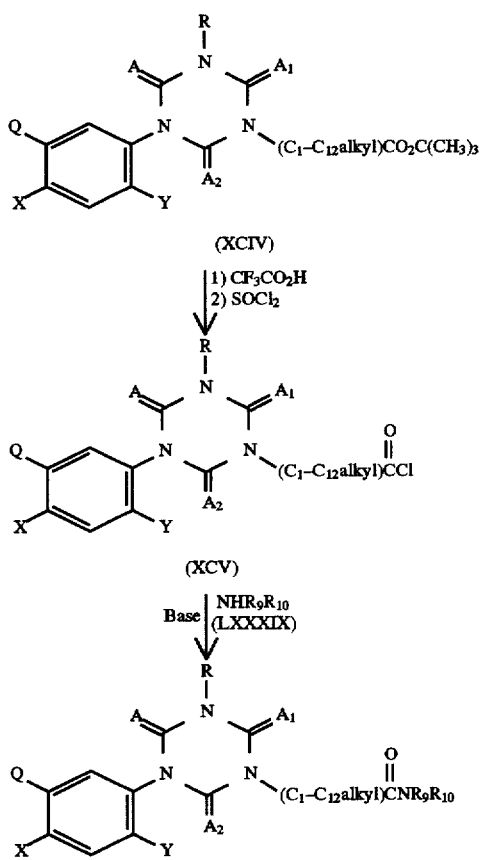

Using the formula XCV acid chloride, formula I compounds wherein $R_1$ is $C_1$–$C_{12}$alkyl substituted with one $C(O)C_1$–$C_4$alkyl group may be prepared as shown below in Flow Diagram XLIV.

FLOW DIAGRAM XLIV

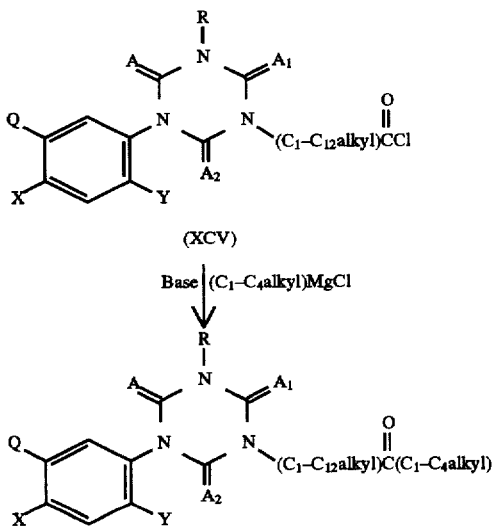

Formula I compounds wherein $R_3$ is $SR_8$ may be prepared by reacting the formula XCV acid chloride with a thiol of formula XCVI. The reaction is shown below in Flow Diagram XLV.

FLOW DIAGRAM XLV

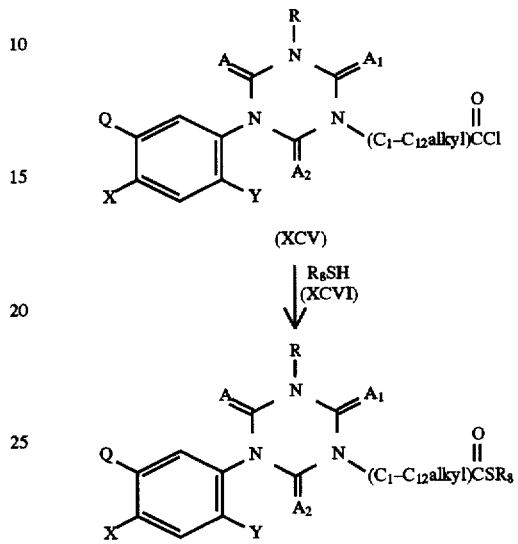

Formula I compounds wherein $R_1$ is $C_1$–$C_{12}$alkyl substituted with one $CH_2OR_4$ group may be prepared by reducing a compound of formula XCVII to form the formula I compound wherein $R_4$ is hydrogen, and optionally reacting the formula I compound wherein $R_4$ is hydrogen with a $C_1$–$C_4$alkyl halide in the presence of a base. The reactions are shown below in Flow Diagram XLVI.

FLOW DIAGRAM XLVI

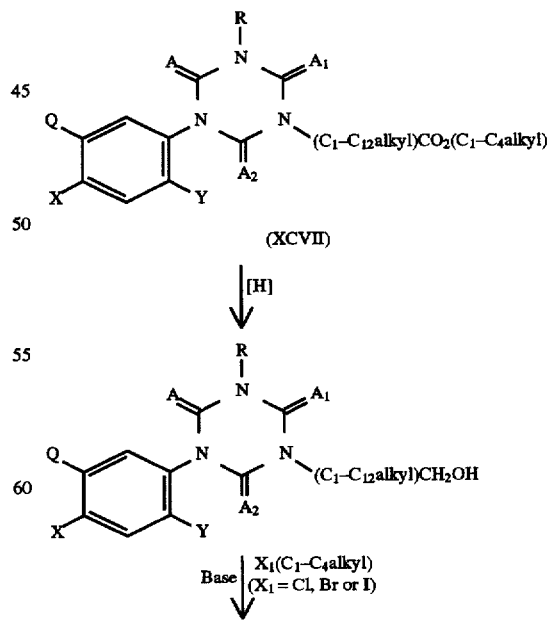

-continued
FLOW DIAGRAM XLVI

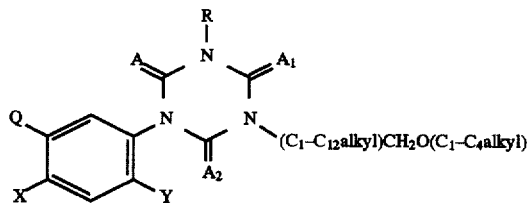

Similarly, compounds of formula I wherein $R_1$ is $C_1$–$C_{12}$alkyl substituted with one $CH_2OC(O)R_5$ group may be prepared by reacting the formula I compound wherein $R_1$ is $C_1$–$C_{12}$alkyl substituted with one $CH_2OH$ group with an acid halide of formula XCVIII in the presence of a base. The reaction is shown in Flow Diagram XLVII.

FLOW DIAGRAM XLVII

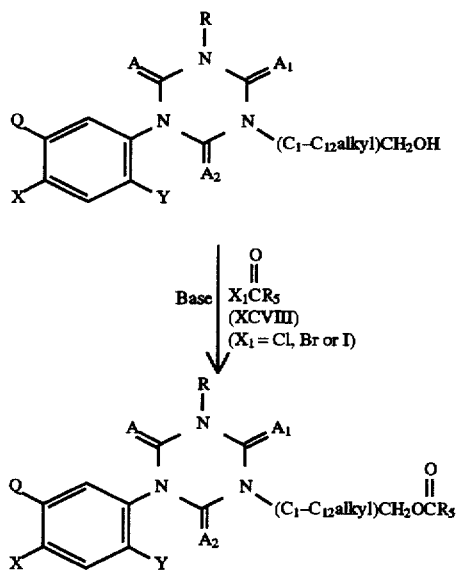

Formula I compounds wherein $R_1$ is $C_1$–$C_{12}$alkyl substituted with one CHO or $CH(OR_6)_2$ group may be prepared by reducing the formula XCVII compound to form an aldehyde of formula XCIX, and reacting the aldehyde with an alcohol of formula C in the presence of an acid. The reactions are shown in Flow Diagram XLVIII.

FLOW DIAGRAM XLVIII

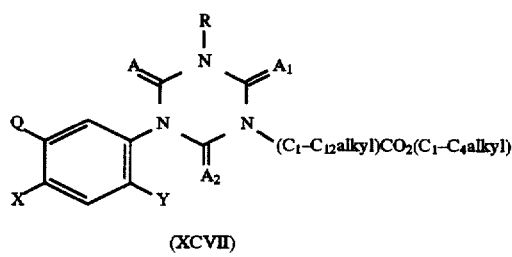

(XCVII)

↓ [H]

-continued
FLOW DIAGRAM XLVIII

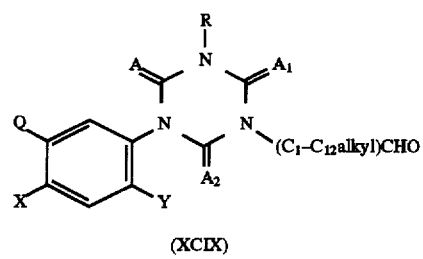

(XCIX)

Acid ↓ $R_6OH$ (C)

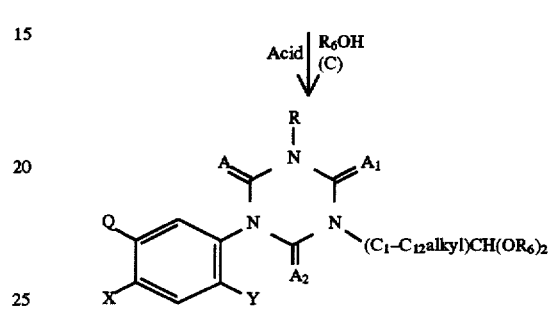

Compounds of formula I wherein $R_1$ is $C_1$–$C_{12}$alkyl substituted with one $HC=NOR_9$ group may be prepared by reacting the formula XCIX aldehyde with an amine of formula CI. The reaction is shown in Flow Diagram XLIX.

FLOW DIAGRAM XLIX

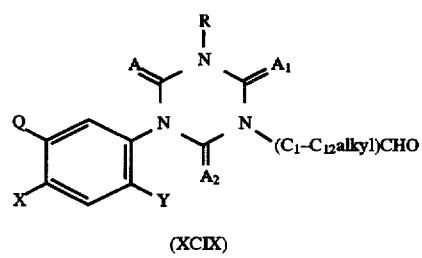

(XCIX)

↓ $H_2NOR_9$ (CI)

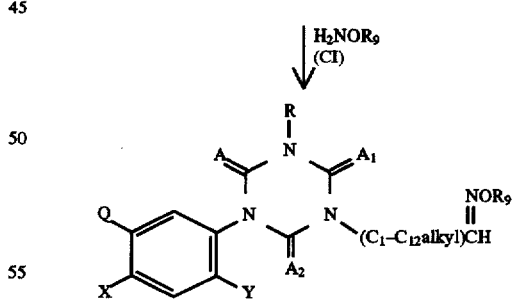

Similarly, compounds of formula I wherein $R_1$ is $C_1$–$C_{12}$alkyl substituted with $HC=NCOR_9$ or $HC=NNHCONH_2$ may be prepared by reacting the formula XCIX aldehyde with an amine of formula CII or a hydrazine of formula CIII. The reactions are shown in Flow Diagram L.

FLOW DIAGRAM L

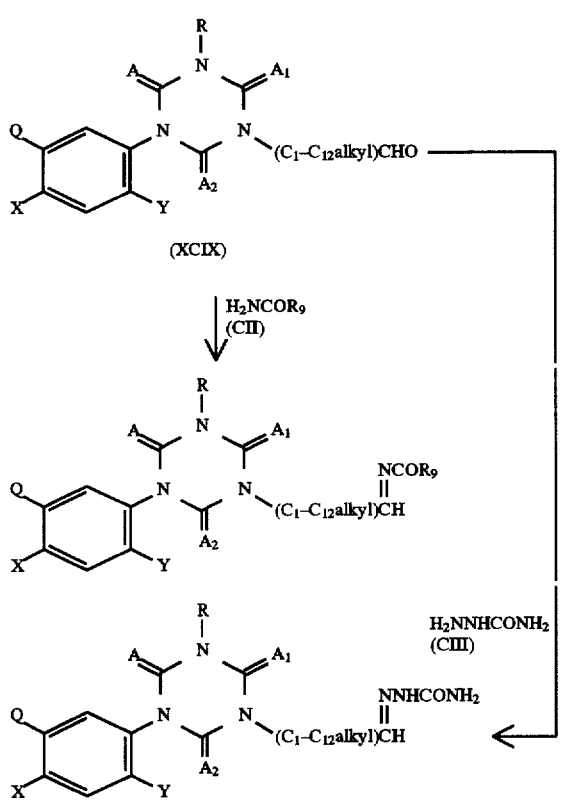

Formula I compounds wherein $R_1$ is $C_1$–$C_{12}$alkyl substituted with cyano may be prepared by dehydrating an amide of formula CIV using standard conditions. The reaction is shown in Flow Diagram LI.

FLOW DIAGRAM LI

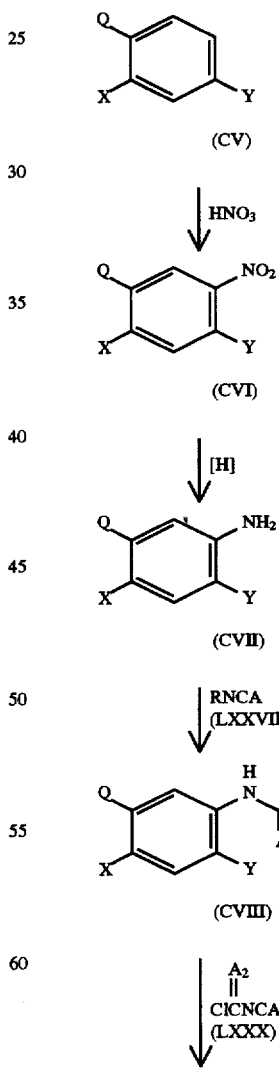

Formula I compounds wherein $R_8$ is an alkali metal, alkaline earth metal, manganese, copper, zinc, cobalt, silver, nickel, ammonium or organic ammonium cation, and/or R is an alkali metal, may be prepared from formula I compounds wherein $R_3$ is OH and/or R is hydrogen by conventional processes known to those skilled in the art.

Compounds of formula I may also be prepared by nitrating a heterocyclylphenyl compound of formula CV with nitric acid to form a 3-nitro-1-heterocyclylphenyl compound of formula CVI, reducing the 3-nitro-1-heterocyclylphenyl compound using standard conditions to form a 3-amino-1-heterocyclylphenyl compound of formula CVII, reacting the 3-amino-1-heterocyclylphenyl compound with an isocyanate or isothiocyanate of formula LXXVIII to form a urea or thiourea of formula CVIII, and cyclizing the urea or thiourea with an isocyanate or isothiocyanate of formula LXXX to obtain a formula I compound wherein $R_1$ is hydrogen, and optionally alkylating the formula I compound wherein $R_1$ is hydrogen with an alkylating agent of formula V in the presence of a base. The reactions are shown in Flow Diagram LII.

FLOW DIAGRAM LII

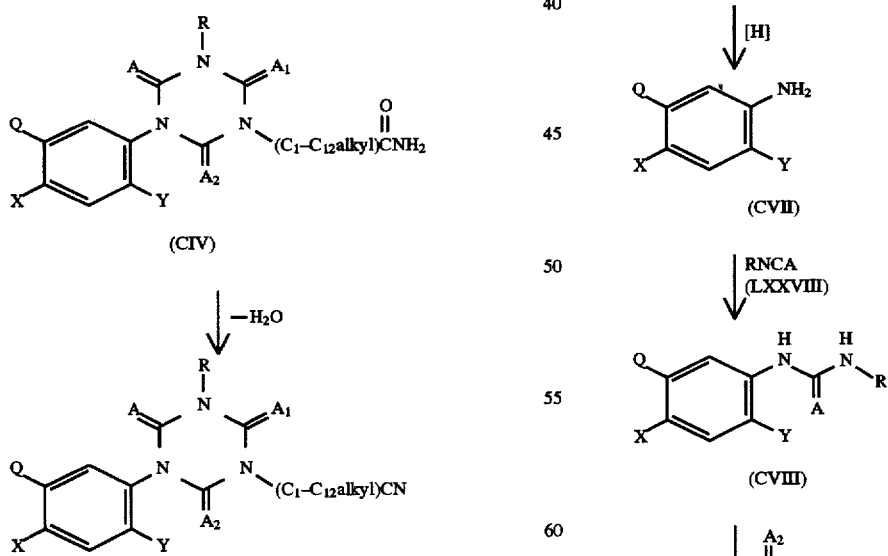

-continued
FLOW DIAGRAM LII

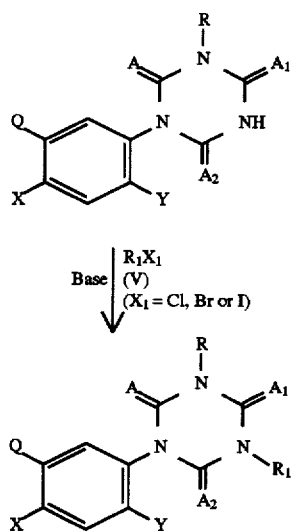

Starting formula II compounds wherein A, A₁ and A₂ are oxygen may be prepared by reacting an amide of formula CIX with sodium hypochlorite and sodium hydroxide to form an isocyanate of formula CX, reacting the isocyanate with an amine of formula CXI to form a urea of formula CXII, cyclizing the urea with N-(chlorocarbonyl) isocyanate to form a trione of formula CXIII, and nitrating the trione with nitric acid. The reaction sequence is shown in Flow Diagram LIII.

FLOW DIAGRAM LIII

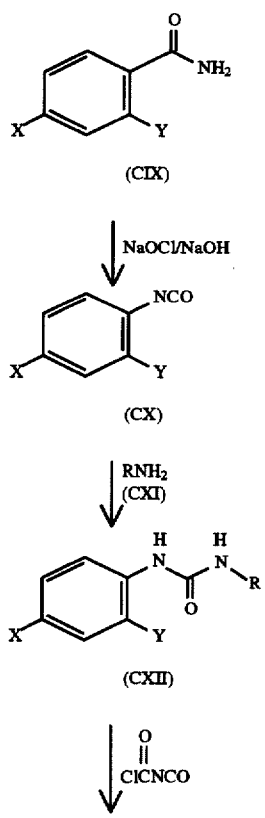

-continued
FLOW DIAGRAM LIII

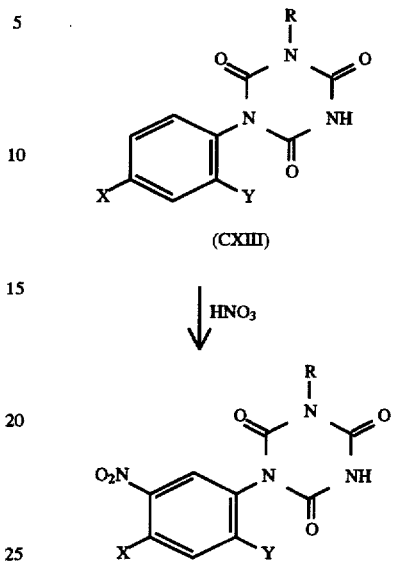

Formula II compounds wherein A and A₂ are oxygen and A₁ is sulfur may be prepared by nitrating a urea of formula CXII to form an intermediate compound of formula CXIV, reacting the formula CXIV compound with an isothiocyanate of formula CXV to form an intermediate compound of formula CXVI, and cyclizing the formula CXVI compound with base. The reaction scheme is shown in Flow Diagram LIV.

FLOW DIAGRAM LIV

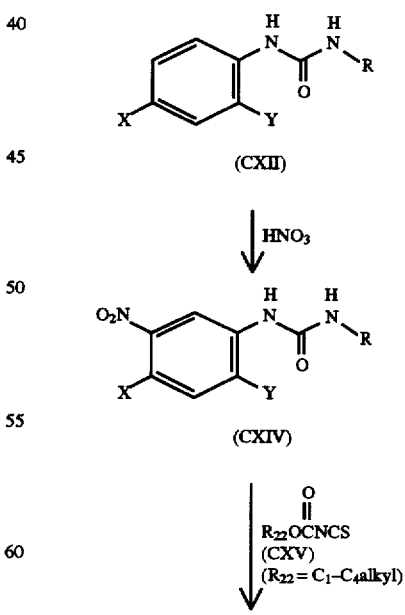

FLOW DIAGRAM LIV -continued

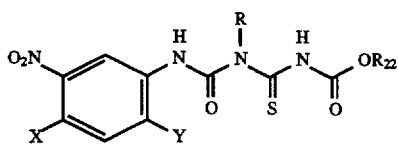

(CXVI)

↓ Base

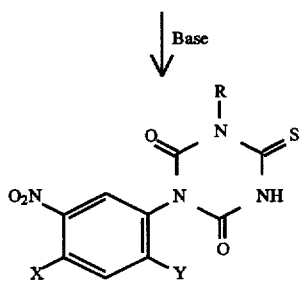

Compounds of formula II wherein A is oxygen or sulfur, $A_1$ is sulfur and $A_2$ is oxygen may be prepared by reacting an isocyanate of formula CX with aqueous base to form an amine of formula CXVII, reacting the amine with an isocyanate or isothiocyanate of formula LXXVIII to form a urea of formula CXVIII, nitrating the urea to obtain an intermediate compound of formula CXIX, reacting the formula CXIX compound with an isothiocyanate of formula CXV to form an intermediate compound of formula CXX, and cyclizing the formula CXX compound with base. The reactions are shown in Flow Diagram LV.

FLOW DIAGRAM LV

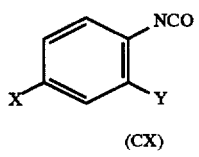

(CX)

↓ Base/H$_2$O

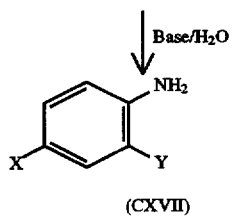

(CXVII)

↓ RNCA
(LXXVIII)

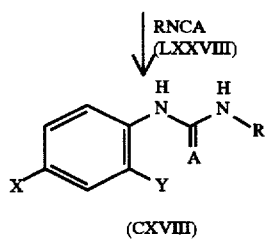

(CXVIII)

↓ HNO$_3$

FLOW DIAGRAM LV -continued

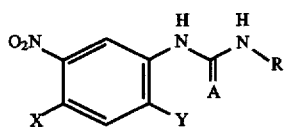

(CXIX)

↓ R$_{22}$OCNCS
(CXV)
(R$_{22}$ = C$_1$–C$_4$alkyl)

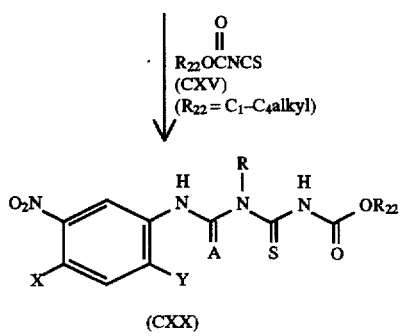

(CXX)

↓ Base

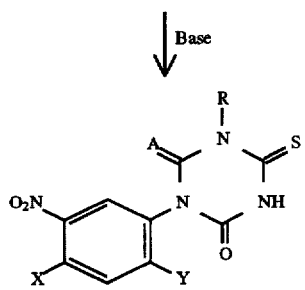

Formula II compounds wherein A is sulfur and $A_1$ and $A_2$ are oxygen may be prepared by nitrating an amine of formula CXVII to obtain a 3-nitroaniline of formula CXXI, reacting to the 3-nitroaniline with an isothiocyanate of formula CXXII to form a thiourea of formula CXXIII, and cyclizing the thiourea with N-(chlorocarbonyl) isocyanate. The reaction scheme is shown in Flow Diagram LVI.

FLOW DIAGRAM LVI

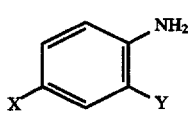

(CXVII)

↓ HNO$_3$

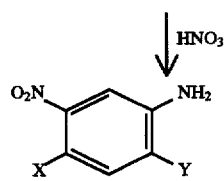

(CXXI)

↓ RNCS
(CXXII)

-continued
FLOW DIAGRAM LVI

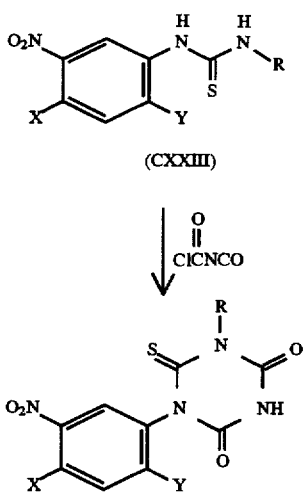

(CXXIII)

Compounds of formula VI Wherein A and $A_1$ are sulfur and $A_2$ is oxygen or sulfur may be prepared by reacting a thiourea of formula CXXIII with an isothiocyanate of formula CXXIV to form an intermediate compound of formula CXXV, and cyclizing the intermediate compound with phosgene or thiophosgene. The reactions are shown below in Flow Diagram LVII.

FLOW DIAGRAM LVII

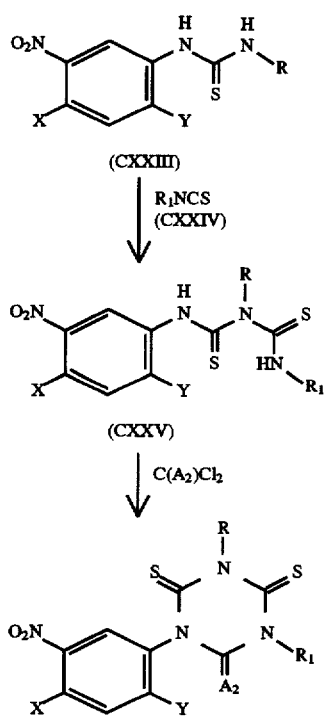

Compounds of formula VI wherein A and $A_1$ are each independently oxygen or sulfur and $A_2$ is sulfur may be prepared by reacting an amine of formula CXXI with an isothiocyanate of formula CXXIV to form a thiourea of formula CXXVI, reacting the thiourea with an isocyanate or isothiocyanate of formula CXXVII to form an intermediate compound of formula CXXVIII, and cyclizing the intermediate compound with phosgene or thiophosgene. The reactions are shown in Flow Diagram LVIII.

FLOW DIAGRAM LVIII

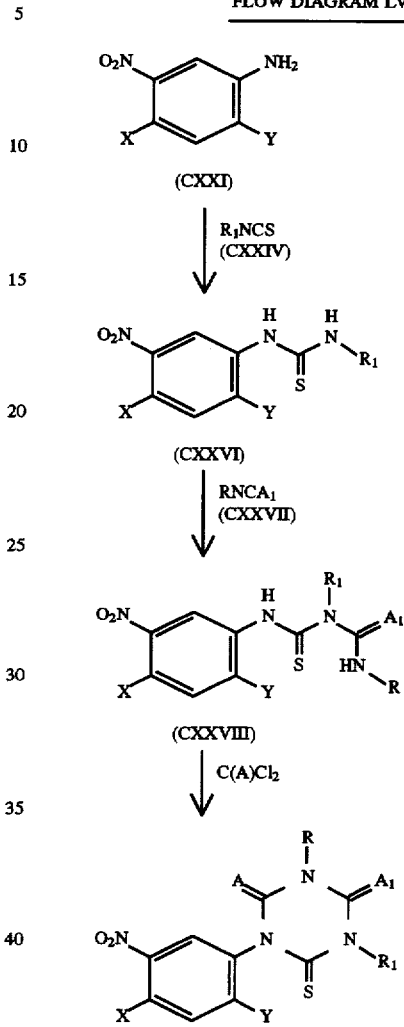

Starting formula CV compounds wherein Q is Q1 may be prepared by reacting an aniline of formula CXXIX with an anhydride of formula IV in the presence of an acid such as acetic acid. The reaction is shown in Flow Diagram LIX.

FLOW DIAGRAM LIX

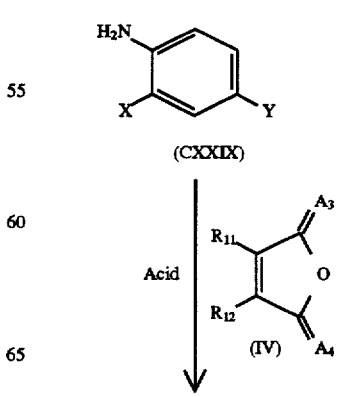

-continued
FLOW DIAGRAM LIX

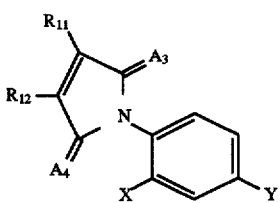

Compounds of formula CV wherein Q is Q2 and Z is CH may be prepared by reacting an isocyanate of formula CXXX with an aminoester of formula IX in the presence of a base, and optionally thionating the resultant compound with a thionating agent such as Lawesson's reagent or $P_4S_{10}$. The reactions are shown in Flow diagram LX.

FLOW DIAGRAM LX

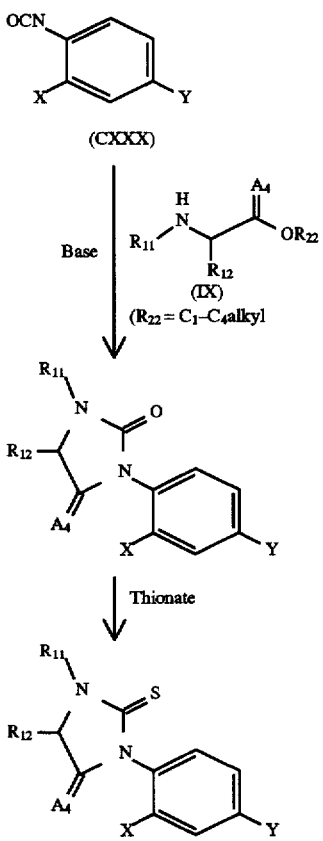

Starting formula CV compounds wherein Q is Q2 and Z is nitrogen may be prepared by reacting an isocyanate of formula CXXX with a substituted hydrazine of formula XXVIII to form an intermediate compound of formula CXXXI, and reacting the intermediate compound with phosgene or thiophosgene to form a formula CV compound wherein Q is Q2, Z is nitrogen and $A_3$ is oxygen, and optionally thionating the formula CV compound wherein Q is Q2, Z is nitrogen and $A_3$ is oxygen. The reaction scheme is shown in Flow Diagram LXI.

FLOW DIAGRAM LXI

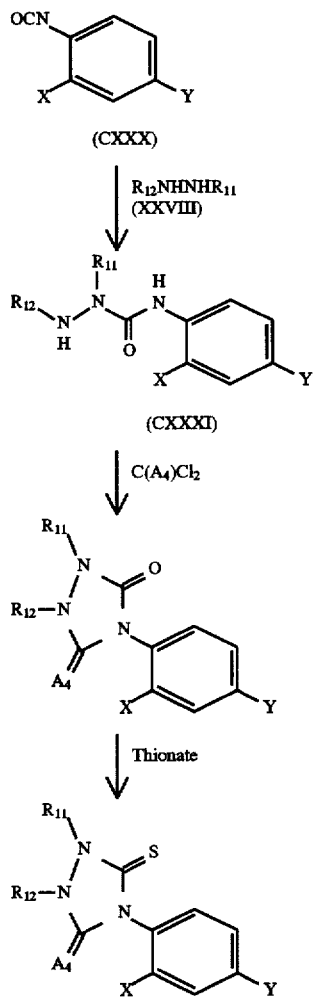

Compounds of formula CV wherein Q is Q11, $A_3$ is sulfur, $A_4$ is oxygen and Z is CH may be prepared by reacting an isothiocyanate of formula CXXXII with an amine of formula XXV to form a thiourea of formula CXXXIII, and reacting the thiourea with an α-halocarbonyl halide of formula XXVII in the presence of a base. The reactions are shown in Flow Diagram LXII.

FLOW DIAGRAM LXII

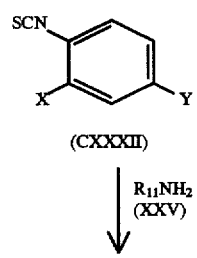

-continued
FLOW DIAGRAM LXII

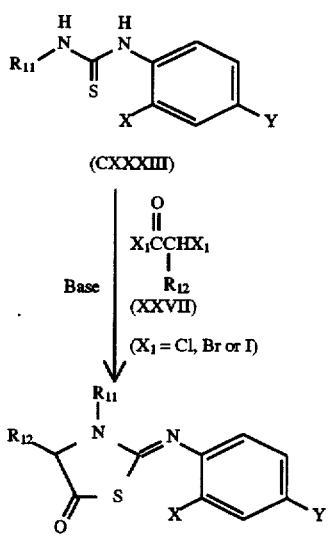

(CXXXIII)

↓ Base, $X_1CCHX_1$ with $R_{12}$ (XXVII) ($X_1$ = Cl, Br or I)

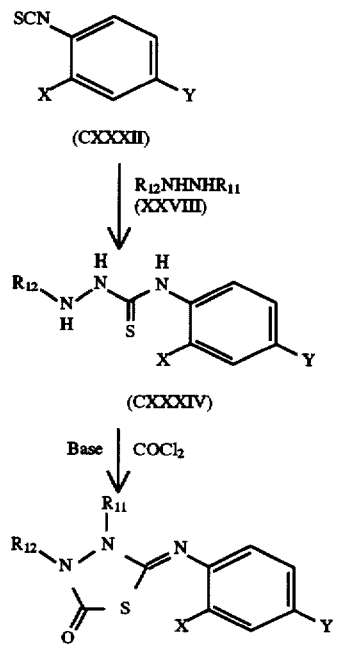

Starting compounds of formula CV wherein Q is Q11, $A_3$ is sulfur, $A_4$ is oxygen and Z is nitrogen may be prepared by reacting an isothiocyanate of formula CXXXII with a substituted hydrazine of formula XXVIII to form an intermediate compound of formula CXXXIV, and reacting the intermediate compound with phosgene or a suitable phosgene equivalent in the presence of a base such as triethylamine. The reaction sequence is shown in Flow Diagram LXIII.

FLOW DIAGRAM LXIII

Compounds of formula CV wherein Q is Q11, $A_3$ and $A_4$ are oxygen and Z is CH may be prepared by reacting an isocyanate of formula CXXX with an amine of formula XXV to form a urea of formula CXXXV, dehydrating the urea to form a carbodiimide of formula CXXXVI, reacting the carbodiimide with an α-halocarbonyl halide of formula XXVII to form a haloamidine of formula CXXXVII, hydrolyzing the haloamidine with aqueous acid to form an acylurea, heating the acylurea in situ to form an O-acylurea of formula CXXXVIII, and reacting the O-acylurea with a base such as triethylamine. The reactions are shown in Flow Diagram LXIV.

FLOW DIAGRAM LXIV

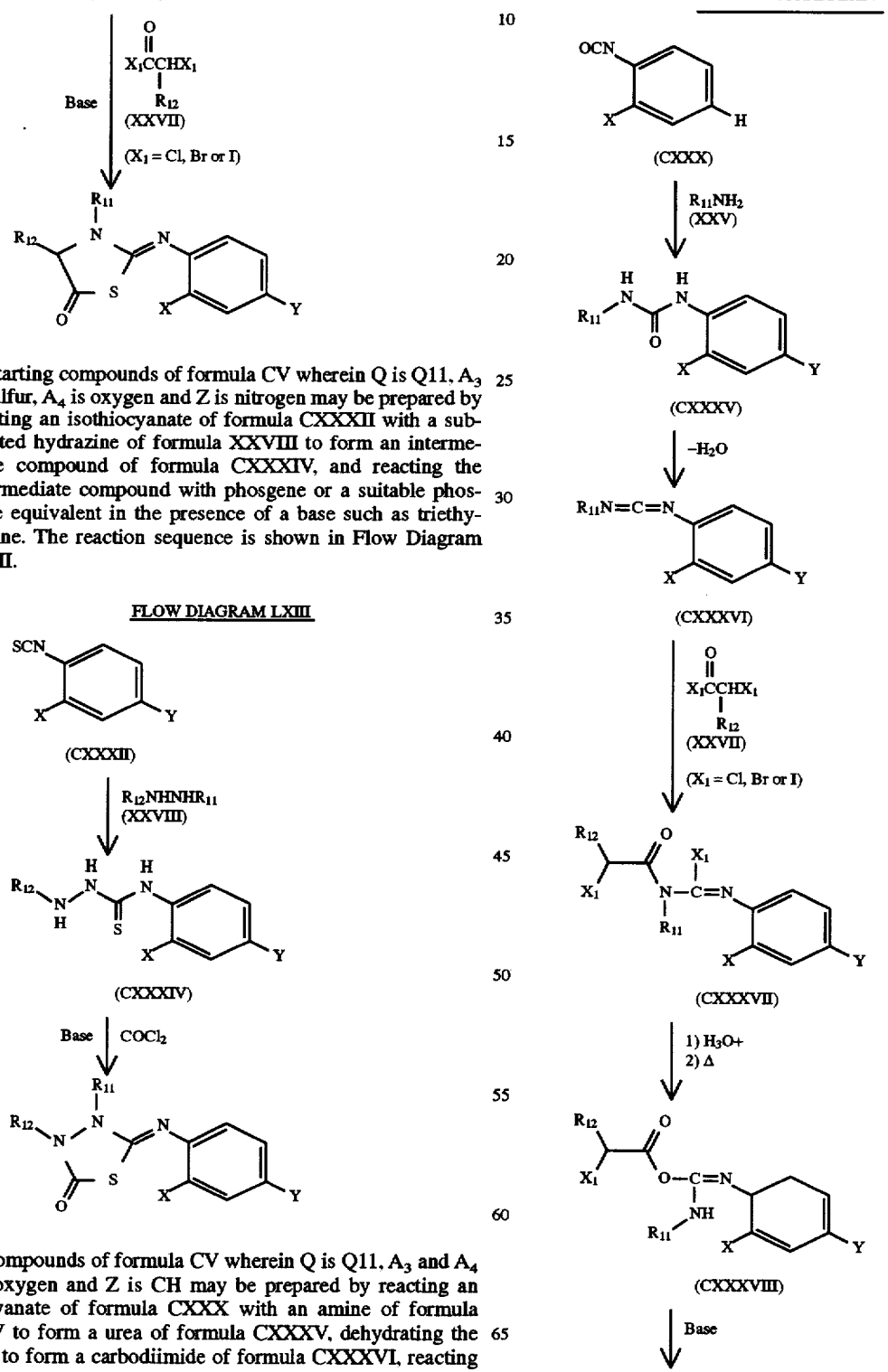

-continued
FLOW DIAGRAM LXIV

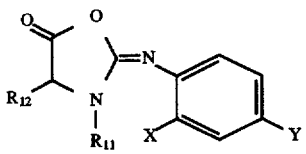

This invention also relates to intermediate compounds which are useful in the preparation of the formula I compounds. The intermediate compounds have the structural formula CXXXIX

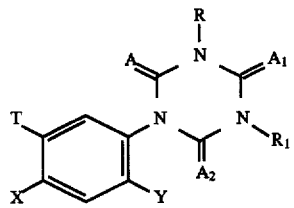   (CXXXIX)

wherein

T is $NH_2$, —NCO, —NCS, —$N_3$, —$NHNH_2$, —NHC(S)$NHR_{11}$, —C(O)$NHNHR_{13}$, —C(O)H, —C(O)$CH_3$, —C(O)$CO_2(C_1-C_4$alkyl), —C(O)$CH_2$C(O)$R_{11}$, —C(O)$CH_2$C($A_3$)O($C_1-C_4$alkyl), —$CO_2(C_1-C_4$alkyl), —N=C=$NR_{11}$, —NHC(O)$NHR_{11}$, —NHC(S)$NR_{11}HNR_{12}$, —N=C(SCH$_3$)$NHR_{11}$, —$NHCO_2$($C_1-C_4$alkyl), —C(Cl)=NOH,

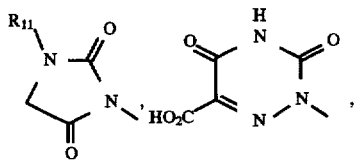

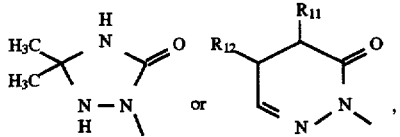

X and Y are each independently hydrogen, halogen, nitro, cyano, $C_1-C_4$alkyl, $C_1-C_4$haloalkyl, $C_1-C_4$alkoxy, $C_1-C_4$haloalkoxy or S(O)$_m R_2$;

m is an integer of 0, 1 or 2;

$R_2$ is $C_1-C_4$alkyl or $C_1-C_4$haloalkyl;

R is hydrogen, $C_1-C_6$alkyl, $C_2-C_{12}$alkoxyalkyl, $C_3-C_{12}$alkylcarbonylalkyl, $C_3-C_{12}$haloalkylcarbonylalkyl, $C_3-C_{12}$alkoxycarbonylalkyl, $C_3-C_{12}$haloalkoxycarbonylalkyl, $C_3-C_6$alkenyl, $C_3-C_6$alkynyl, phenyl optionally substituted with one to three halogen, $C_1-C_4$alkyl, $C_1-C_4$alkoxy or $C_1-C_4$haloalkoxy groups, or benzyl optionally substituted with one to three halogen, $C_1-C_4$alkyl, $C_1-C_4$alkoxy or $C_1-C_4$haloalkoxy groups;

$R_1$ is hydrogen, $C_3-C_6$alkenyl, $C_3-C_6$alkynyl, cyano, $C_1-C_{12}$alkyl optionally substituted with one or more halogen atoms, or one cyano, C(O)$R_3$, OC(O)$R_5$, $CH_2OC(O)R_5$, $OR_4$, $CH_2OR_4$ or $CR_6(OR_7)_2$ group, or one phenyl group optionally substituted with one to three halogen, $C_1-C_4$alkyl, $C_1-C_4$alkoxy or $C_1-C_4$haloalkoxy groups, or phenyl optionally substituted with one to three halogen, $C_1-C_4$alkyl, $C_1-C_4$alkoxy or $C_1-C_4$haloalkoxy groups;

$R_3$ is $OR_8$, $SR_8$ or $NR_9R_{10}$;

$R_4$, $R_5$ and $R_6$ are each independently hydrogen, $C_1-C_4$alkyl or $C_1-C_4$haloalkyl;

$R_7$ is $C_1-C_4$alkyl;

$R_8$ is $C_1-C_6$alkyl optionally substituted with $C_1-C_4$alkoxy, $C_1-C_4$alkylthio, halogen, hydroxy, $C_3-C_6$cycloalkyl, furyl or phenyl optionally substituted with one or more halogen, cyano, nitro, $C_1-C_4$alkyl, $C_1-C_4$haloalkyl, $C_1-C_4$alkoxy or $C_1-C_4$haloalkoxy groups, $C_3-C_6$alkenyl optionally substituted with $C_1-C_4$alkoxy, halogen, $C_3-C_6$cycloalkyl or phenyl optionally substituted with one or more halogen, cyano, nitro, $C_1-C_4$alkyl, $C_1-C_{14}$haloalkyl, $C_1-C_4$alkoxy or $C_1-C_4$haloalkoxy groups, $C_3-C_6$alkynyl optionally substituted with $C_1-C_4$alkoxy or halogen, or $C_3-C_6$cycloalkyl;

$R_9$ and $R_{10}$ are each independently hydrogen, $C_1-C_6$alkyl, benzyl optionally substituted with one or more halogen, cyano, nitro, $C_1-C_4$alkyl, $C_1-C_4$haloalkyl, $C_1-C_4$alkoxy or $C_1-C_4$haloalkoxy groups, or phenyl optionally substituted with one or more halogen, cyano, nitro, $C_1-C_4$alkyl, $C_1-C_4$haloalkyl $C_1-C_4$alkoxy or $C_1-C_4$haloalkoxy groups;

$R_{11}$ and $R_{12}$ are each independently hydrogen, $C_1-C_6$alkyl optionally substituted with one or more halogen atoms, or $C_3-C_6$cycloalkyl optionally substituted with one or more halogen atoms, and when $R_{11}$ and $R_{12}$ are taken together with the atoms to which they are attached, they represent a four- to seven-membered saturated or unsaturated ring optionally interrupted by O, S(O)$_r$ or N, and optionally substituted with one to three methyl groups or one or more halogen atoms;

$R_{13}$ is hydrogen, $C_1-C_3$alkyl or $C_1-C_3$haloalkyl;

A, $A_1$, $A_2$, and $A_3$ are each independently O or S; and r is an integer of 0, 1 or 2.

Preferred formula CXXXIX intermediate compounds are those wherein

T is $NH_2$, —NCO, —NCS, —$N_3$, —$NHNH_2$, —NHC(S)$NHR_{11}$, —NHC(O)$NHR_{11}$, —NHC(S)$NR_{11}NHR_{12}$ or —N=C=$NR_{11}$;

X is hydrogen or halogen;

Y is hydrogen, halogen, nitro or cyano;

R is hydrogen, $C_1-C_4$alkyl, $C_1-C_4$alkoxymethyl, ($C_1-C_4$alkoxy)carbonylmethyl, $C_3-C_6$alkenyl or $C_3-C_6$alkynyl;

$R_1$ is hydrogen, $C_3-C_6$alkenyl, $C_3-C_6$alkynyl or $C_1-C_6$alkyl optionally substituted with one $CO_2R_8$ group;

$R_8$ is $C_1-C_6$alkyl;

$R_{11}$ and $R_{12}$ are each independently hydrogen or $C_1-C_4$alkyl, and when $R_{11}$ and $R_{12}$ are taken together with the atoms to which they are attached, they form a ring in which $R_{11}R_{12}$ is a $C_2-C_5$alkylene group optionally interrupted by S(O)$_r$ and optionally substituted with one to three methyl groups or one or more halogen atoms;

A, $A_1$ and $A_2$ are O; and r is an integer of 0, 1 or 2.

More preferred formula CXXXIX intermediate compounds of this invention are those wherein T is $NH_2$, —NCO, —NCS, —NHC(S)$NHR_{11}$ or —NHC(O)$NHR_{11}$;

X and Y are each independently hydrogen, F or Cl;

R is hydrogen, $C_1$–$C_4$alkyl, $C_1$–$C_4$alkoxymethyl, ($C_1$–$C_4$alkoxy)carbonylmethyl, allyl or propargyl;

$R_1$ is hydrogen, allyl, propargyl or $C_1$–$C_4$alkyl optionally substituted with one $CO_2R_8$ group;

$R_8$ is $C_1$–$C_4$alkyl;

$R_{11}$ is hydrogen or $C_1$–$C_4$alkyl; and

A, $A_1$ and $A_2$ are O.

This invention also relates to intermediate compounds having the structural formula CXL.

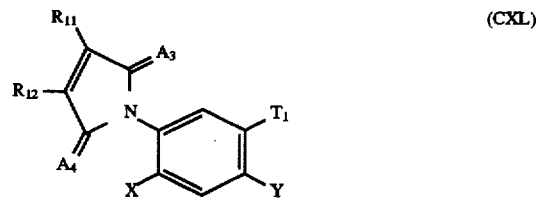

(CXL)

wherein $T_1$ is $NO_2$, $NH_2$ or —NHC(A)NHR;

A, $A_3$ and $A_4$ are each independently O or S;

X and Y are each independently hydrogen, halogen, nitro, cyano, $C_1$–$C_4$alkyl, $C_1$–$C_4$haloalkyl, $C_1$–$C_4$alkoxy, $C_1$–$C_4$haloalkoxy or $S(O)_mR_2$;

m is an integer of 0, 1 or 2;

$R_2$ is $C_1$–$C_4$alkyl or $C_1$–$C_4$haloalkyl;

R is hydrogen, $C_1$–$C_6$alkyl, $C_2$–$C_{12}$alkoxyalkyl, $C_3$–$C_{12}$alkylcarbonylalkyl, $C_3$–$C_{12}$haloalkylcarbonylalkyl, $C_3$–$C_{12}$alkoxycarbonylalkyl, $C_3$–$C_{12}$haloalkoxycarbonylalkyl, $C_3$–$C_6$alkenyl, $C_3$–$C_6$alkynyl, phenyl optionally substituted with one to three halogen, $C_1$–$C_4$alkyl, $C_1$–$C_4$alkoxy or $C_1$–$C_4$haloalkoxy groups, or benzyl optionally substituted with one to three halogen, $C_1$–$C_4$alkyl, $C_1$–$C_4$alkoxy or $C_1$–$C_4$haloalkoxy groups;

$R_{11}$ and $R_{12}$ are each independently hydrogen, $C_1$–$C_6$alkyl optionally substituted with one or more halogen atoms, or $C_3$–$C_6$cycloalkyl optionally substituted with one or more halogen atoms, and when $R_{11}$ and $R_{12}$ are taken together with the atoms to which they are attached, they represent a four- to seven-membered saturated or unsaturated ring optionally interrupted by O, $S(O)_r$ or N, and optionally substituted with one to three methyl groups or one or more halogen atoms; and r is an integer of 0, 1 or 2.

Preferred formula CXL intermediate compounds are those wherein $T_1$ is $NO_2$, $NH_2$ or —NHC(O)NHR;

$A_3$ and $A_4$ are O;

X and Y are each independently hydrogen or halogen;

R is $C_1$–$C_6$alkyl, $C_3$–$C_6$alkenyl or $C_3$–$C_6$alkynyl;

$R_{11}$ and $R_{12}$ are taken together with the atoms to which they are attached to form a ring in which $R_{11}R_{12}$ is a $C_2$–$C_5$alkylene group optionally interrupted by $S(O)_r$, and optionally substituted with one to three methyl groups or one or more halogen atoms, or $R_{11}R_{12}$ is represented by the structure: —$CR_{18}$=$CR_{19}$—$CR_{20}$=$CR_{21}$— where $R_{18}$, $R_{19}$, $R_{20}$ and $R_{21}$ are each independently hydrogen, halogen or methyl; and r is an integer of 0, 1 or 2.

More preferred intermediate compounds of formula CXL are those wherein $T_1$ is $NO_2$, $NH_2$ or —NHC(O)NHR;

$A_3$ and $A_4$ are O;

X is F or Cl;

Y is Cl;

R is $C_1$–$C_4$alkyl, allyl or propargyl; and $R_{11}$ and $R_{12}$ are taken together with the atoms to which they are attached to form a ring in which $R_{11}R_{12}$ is a butylene group optionally substituted with one to three methyl groups.

The formula I compounds of the present invention are effective herbicidal agents useful for the control of a wide variety of undesirable plant species. Those compounds are effective for controlling weeds native to both dry land and wet land areas. The compounds are also useful as aquatic herbicides and are effective in controlling the above-said plants when applied to the foliage thereof or to soil or water containing seeds or other propagating organs thereof such as stolons, tubers or rhizomes, at rates of from about 0.016 to 4.0 kg/ha and preferably from about 0.032 to 2.0 kg/ha.

The formula I compounds of this invention are best suited for use as broad spectrum herbicides, especially when applied postemergence to the locus in which weed control is desired. However, certain compounds of this invention are selective. In fact, some of the compounds of this invention are selective in crops such as soybeans, rice and corn.

While the formula I compounds of this invention are effective for controlling undesirable plant species when employed alone, they may also be used in combination with other biological chemicals, including other herbicides.

The formula I compounds of this invention may be applied to crops in the form of a solid or liquid herbicidal composition, comprising a herbicidally effective amount of the compound dispersed or dissolved in an agronomically acceptable, inert solid or liquid carrier. The compositions may be applied as preemergence or postemergence treatments.

The formula I compounds may be formulated as emulsifiable concentrates, wettable powders, granular formulations, flowable concentrates and the like.

In order to facilitate a further understand-ing of the invention, the following examples are pre-sented primarily for the purpose of illustrating more specific details thereof. The invention should not be deemed limited by the examples as the full scope of the invention is defined in the claims. The term NMR designates nuclear magnetic resonance spectroscopy.

EXAMPLE 1

Preparation of 1-(2-Chloro-4-fluorophenyl)-3-methylurea

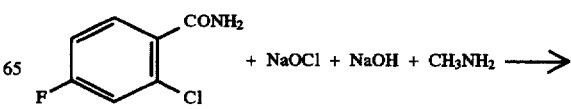

-continued

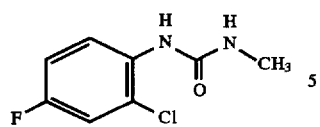

A mixture of 50% sodium hydroxide solution (28 g, 0.35 mol) and 5% sodium hypochlorite solution (226 mL) is added to a mixture of 2'-chloro-4'-fluorobenzamide (50 g, 0.288 mol) in methanol at 0° C. After the addition is complete, 55 mL of a 40% methylamine solution is added at 0° C. The resultant reaction mixture is heated to and stirred at 55° C. for 6 hours, cooled to room temperature and filtered to obtain a solid. The solid is washed sequentially with water and hexanes and air-dried to give the title product as a white solid (30 g, mp 174°–178° C.).

Using essentially the same procedure, but substituting 2',4'-dichlorobenzamide for 2'-chloro-4'-fluorobenzamide, 1-(2,4-dichlorophenyl)-3-methylurea is obtained as a beige solid.

EXAMPLE 2

Preparation of 1-(2,4-Difluorophenyl-3-methylurea

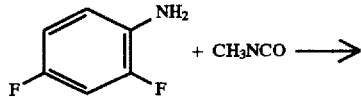

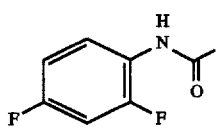

Methyl isocyanate (9.6 g, 10 mL, 0.174 mol) is added to a solution of 2,4-difluoroaniline (15 g, 0.116 mol) in toluene. The reaction mixture is stirred for 1 hour and filtered to obtain a solid. The solid is washed with hexanes and air-dried to give the title product as an off-white solid, mp 182°–183° C.

Using essentially the same procedure, but using the appropriately substituted aniline, the following compounds are obtained:

| U | X | Y | mp°C. |
|---|---|---|---|
| NO$_2$ | H | F | 229–232 |
| H | F | Cl | |

EXAMPLE 3

Preparation of 1-(2-Chloro-4-fluorophenyl)-3-methyl-s-triazine-2,4,6(1H,3H,5H)-trione

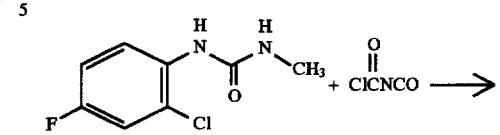

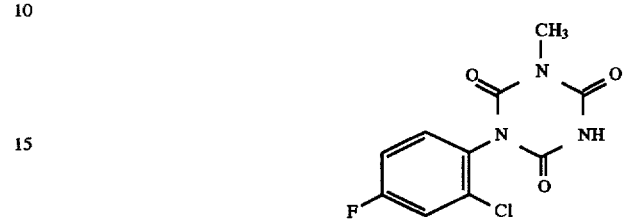

N-(Chlorocarbonyl) isocyanate (18.97 g, 0.180 mol) is added to a mixture of 1-(2-chloro-4-fluorophenyl)-3-methylurea (29.2 g, 0.144 mol) in toluene. The reaction mixture is stirred for 90 minutes and filtered to give the title product as a white solid (32.1 g, mp 225°–228° C.). Using essentially the same procedure, but using the appropriately substituted urea, the following compounds are obtained:

| U | X | Y | mp°C. |
|---|---|---|---|
| H | F | F | 242–245 |
| H | Cl | Cl | 200–204 |
| NO$_2$ | H | F | 180–183 |

EXAMPLE 4

Preparation of 1-(2-Chloro-4-fluoro-5-nitrophenyl)-3-methyl-s-triazine-2,4,6(1H,3H,5H)-trione

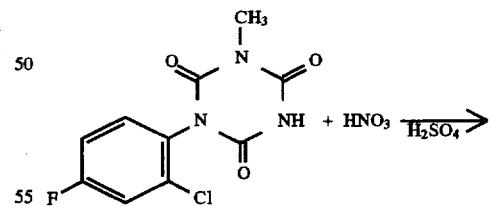

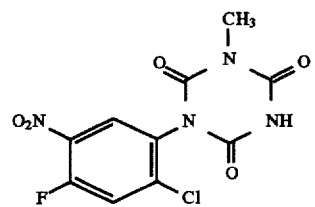

Nitric acid (70% real, 8.3 mL, 0.131 mol) is added to a solution of 1-(2-chloro-4-fluorophenyl)-3-methyl-s-triazine- 2,4,6(1H,3H,5H)-trione (32.4 g, 0.119 mol) in concentrated sulfuric acid while maintaining the reaction mixture temperature below 10° C. After the addition is complete, the reaction mixture is stirred at room temperature for 30 minutes, cooled to 10° C. and diluted with ice-water. The resultant aqueous mixture is filtered to obtain a solid which is washed with water and air-dried to give the title product as a white solid (28.5 g, mp 135°–139° C.).

Using essentially the same procedure, but using the appropriately substituted 1-phenyl-3-methyl-s-triazine-2,4,6 (1H,3H,5H)-trione, the following compounds are obtained:

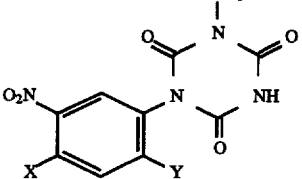

| X | Y | mp°C. |
|---|---|---|
| F | F | 100–120 |
| Cl | Cl | 220–222 |

EXAMPLE 5

Preparation of 1-(5-Amino-2-chloro-4-fluorophenyl)-3-methyl-s-triazine-2,4,6(1H,3H,5H)-trione

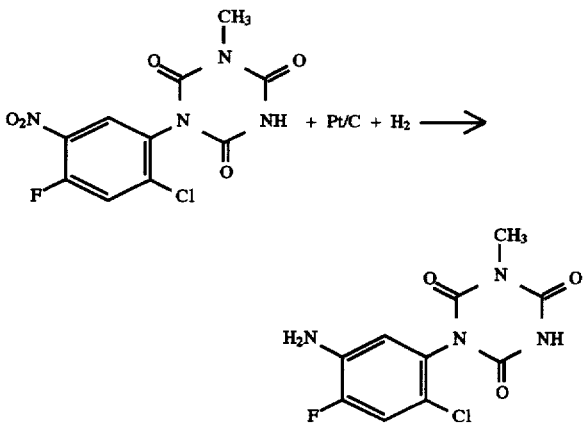

A mixture of 1-(2-chloro-4-fluoro-5-nitrophenyl)-3-methyl-s-triazine-2,4,6(1H,3H,5H)-trione (28.5 g, 0.09 mol) and 5% platinum on activated carbon (1 g) in ethyl acetate is hydrogenated at 55 psi until hydrogen uptake is complete. The reaction mixture is then filtered and concentrated in vacuo to give the title product as a white solid, mp 244°–245° C.

Using essentially the same procedure, but using the appropriately substituted 1-nitrophenyl-3-methyl-s-triazine-2,4,6(1H,3H,5H)-trione, the following compounds are obtained:

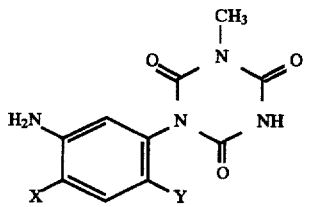

| X | Y | mp°C. |
|---|---|---|
| F | F | 194–196 |
| Cl | Cl | 145–151 |
| H | F | |

EXAMPLE 6

Preparation of 1-[4-Chloro-2-fluoro-5-(hexahydro-3-methyl-2,4,6-trioxo-s-triazin-1-yl)phenyl]-1-cyclohexene-1,2-dicarboximide

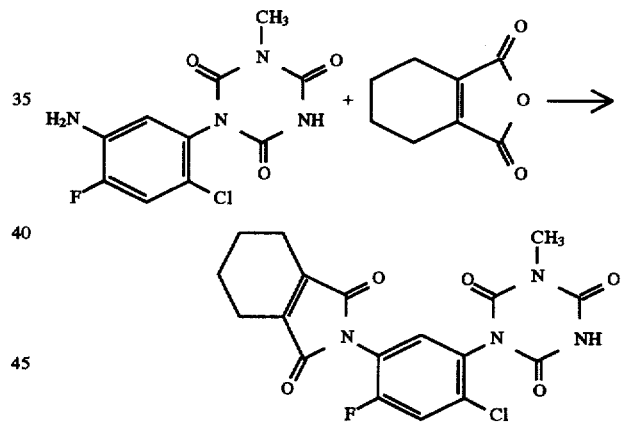

A mixture of 1-(5-amino-2-chloro-4-fluorophenyl)-3-methyl-s-triazine-2,4,6(1H,3H,5H)-trione (23.4 g, 0.0816 mol) and 3,4,5,6-tetrahydrophthalic anhydride (13.04 g, 0.0857 mol) in glacial acetic acid is stirred at 100° C. for 8 hours, cooled to 25° and poured into water. The resultant aqueous mixture is filtered to obtain a solid which is washed with water and dried in a vacuum oven to give the title product as a beige solid (22.5 g, mp 154°–165° C.).

Using essentially the same procedure, but using the appropriately substituted 1-(aminophenyl)-3-methyl-s-triazine-2,4,6(1H,3H,5H)-trione, the following compounds are obtained:

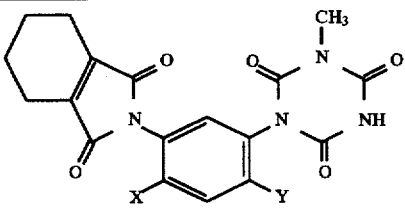

| X  | Y  | mp°C.   |
|----|----|---------|
| F  | F  | 135–150 |
| Cl | Cl | 125–135 |
| H  | F  |         |

EXAMPLE 7

Preparation of Tert-butyl 3-[2-chloro-5-(1-cyclohexene-1,2-dicarboximido)-4-fluorophenyl]tetrahydro-5-methyl-2,4,6-trioxo-s-triazine-1(2H)-acetate

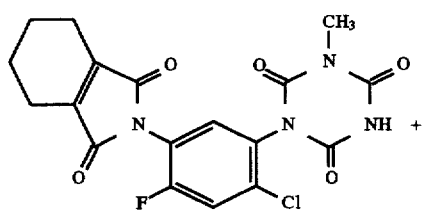

BrCH$_2$CO$_2$C(CH$_3$)$_3$ + K$_2$CO$_3$ ⟶

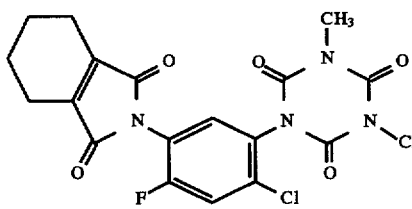

A mixture of 1-[4-chloro-2-fluoro-5-(hexahydro-3-methyl-2,4,6-trioxo-s-triazin-1-yl)phenyl]-1-cyclohexene-1,2-dicarboximide (8 g, 0.0199 mol) and potassium carbonate (4.13 g, 0.0299 mol) in N,N-dimethylformamide is treated with tert-butyl bromoacetate (5.82 g, 0.0299 mol), stirred at room temperature for 18 hours and poured into water. The resultant aqueous mixture is filtered to obtain a solid which is Washed with water and air-dried to give the title product as a white solid (6.13 g, mp 105°–115° C.).

Using essentially the same-procedure, but using the appropriately substituted 1-[5-(hexahydro-3-methyl-2,4,6-trioxo-s-triazin-1-yl)phenyl]-1-cyclohexene-1,2-dicarboximide and the appropriate alkylating agent, the following compounds are obtained:

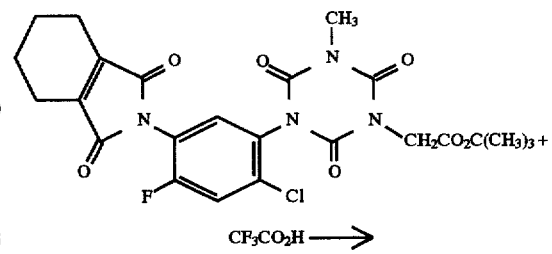

| X  | Y  | R$_1$              | mp°C.   |
|----|----|--------------------|---------|
| F  | F  | CH$_2$CO$_2$CH$_3$ | 100–115 |
| F  | Cl | CH$_2$CO$_2$CH$_3$ | 95–110  |
| Cl | Cl | CH$_2$CO$_2$C(CH$_3$)$_3$ | 95–100 |
| Cl | Cl | CH$_2$CO$_2$CH$_3$ | 120–125 |
| H  | F  | CH$_2$CO$_2$CH$_3$ | 110–120 |
| F  | Cl | CH$_2$CH=CH$_2$    | 91–106  |
| F  | Cl | CH$_2$C≡CH         | 105–122 |

EXAMPLE 8

Preparation of 3-[2-Chloro-5-(1-cyclohexene-1,2-dicarboximido)-4-fluorophenyl]tetrahydro-5-methyl-2,4,6-trioxo-s-triazine-1(2H)-acetic acid

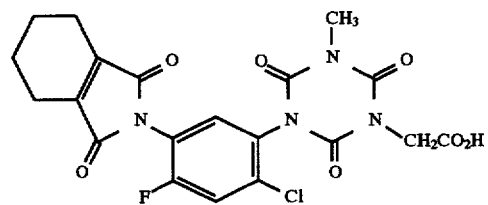

CF$_3$CO$_2$H ⟶

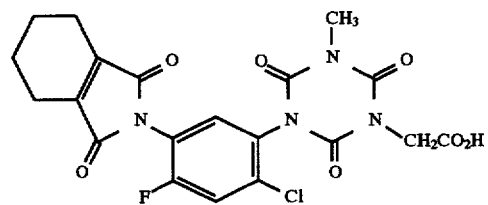

A solution of tert-butyl 3-[2-chloro-5-(1-cyclohexene-1,2-dicarboximido)-4-fluorophenyl]tetrahydro-5-methyl-2,4,6-trioxo-s-triazine-1(2H)-acetate (5.92 g, 0.011 mol) in trifluoroacetic acid is reluxed for 2 hours, cooled to room temperature and concentrated in vacuo to obtain an amber gum. The gum is dissolved in ether and the resultant solution is concentrated in vacuo to give the title product as a yellow solid (3.62 g, mp 75°–80° C.).

EXAMPLE 9

Preparation of Isopropyl 3-[2-chloro-5-(1-cyclohexene-1,2-dicarboximido)-4-fluorophenyl]tetrahydro-5-methyl-2,4,6-trioxo-s-triazine-1(2H)-acetate

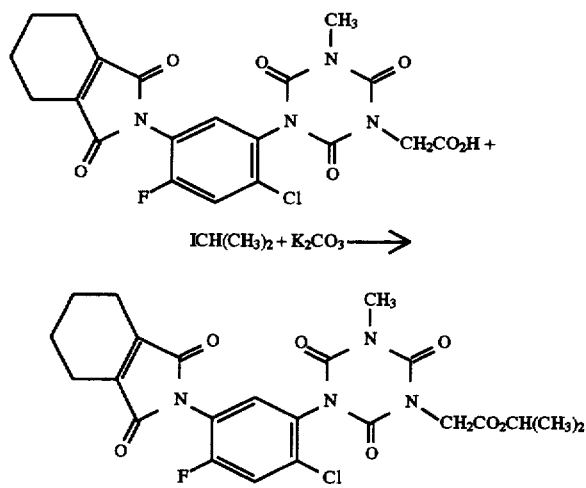

A solution of 3-[2-chloro-5-(1-cyclohexene-1,2-dicarboximido)-4-fluorophenyl]tetrahydro-5-methyl-2,4,6-trioxo-s-triazine-1(2H)-acetic acid (1.5 g, 3.13 mmol) in N,N-dimethylformamide is treated with 2-iodopropane (0.849 g, 5 mmol) and potassium carbonate (0.69 g; 5 mmol), stirred overnight at room temperature and poured into water. The resultant aqueous mixture is filtered to obtain a solid which is air-dried to give the title product as a beige solid (0.6 g, mp 100°–130° C.).

EXAMPLE 10

Preparation of N-[(4-Fluoro-3-nitrophenyl)carbamoyl]glycine, ethyl ester

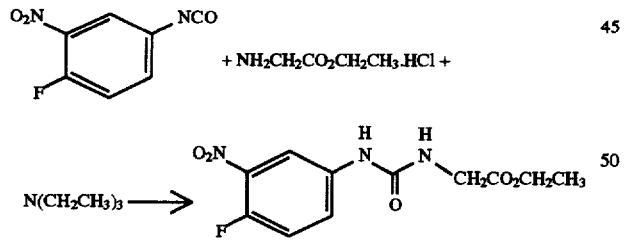

A solution of 4-fluoro-3-nitrophenyl isocyanate (10 g, 0.055 mol) in anhydrous tetrahydrofuran is cooled to 0° C., treated with glycine ethyl ester hydrochloride (7.7 g, 0.052 mol), treated with triethylamine (5.56 g, 0.055 mol) while maintaining the temperature below 10° C., stirred at room temperature for 1 hour and poured into water. The aqueous mixture is extracted with ether. The combined organic extracts are washed sequentially with 1N hydrochloric acid and brine, dried over anhydrous. magnesium sulfate, and concentrated in vacuo to obtain a solid which is air-dried to give the title product as a yellow solid (8.8 g, mp 115°–120° C.).

EXAMPLE 11

Preparation of N-[(3-Amino-4-fluorophenyl)carbamoyl]glycine, ethyl ester

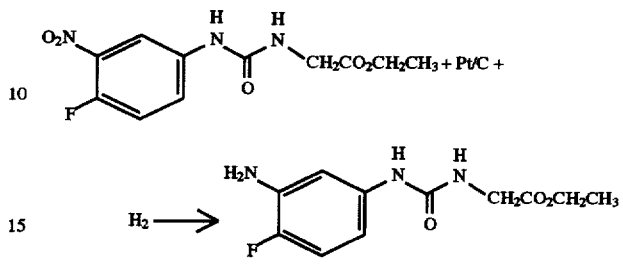

A mixture of N-[(4-fluoro-3-nitrophenyl)carbamoyl]glycine, ethyl ester (8 g, 0.029 mol) and 5% platinum on activated carbon (0.5 g) in ethyl acetate is hydrogenated at 50 psi until hydrogen uptake is complete. The reaction mixture is then filtered and cooled in an ice-bath until a solid forms. The solid is collected by filtration and air-dried to give the title product as a white solid (4.5 g, mp 152°–153° C.).

EXAMPLE 12

Preparation of {N-[3-(1-Cyclohexene-1,2-dicarboximido)-4-fluorophenyl]carbamoyl}glycine, ethyl ester

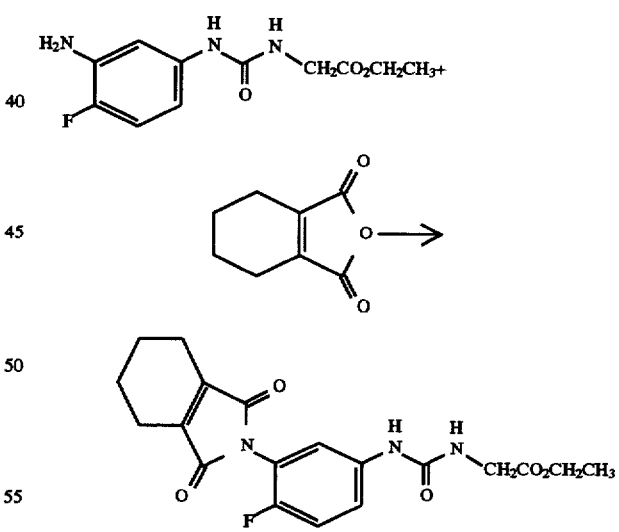

A solution of N-[(3-amino-4-fluorophenyl)carbamoyl]glycine, ethyl ester (4 g, 0.0157 mol) in acetic acid is treated with 3,4,5,6-tetrahydrophthalic anhydride (2.43 g, 0.016 mol), heated at 100° C. for 8 hours, cooled to room temperature and poured into water. The resultant aqueous mixture is filtered to obtain a solid which is recrystallized from an ethyl acetate/hexanes solution to give the title product as a yellow solid, mp 72°–82° C.

EXAMPLE 13

Preparation of Ethyl 3-[3-(1-cyclohexene-1,2-dicarboximido)-4-fluorophenyl]tetrahydro-2,4,6-trioxo-s-triazine-1(2H)-acetate

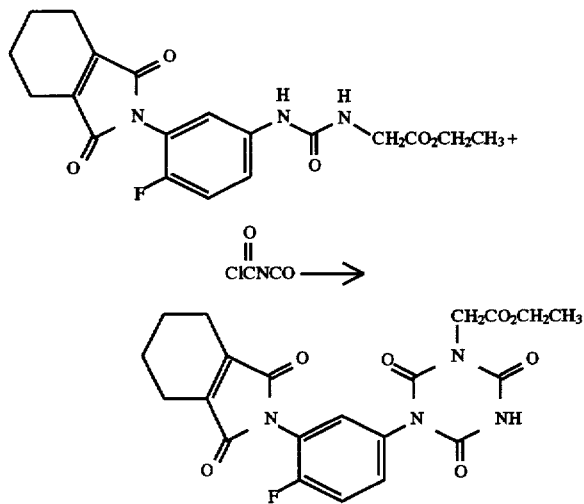

A solution of {N-[3-(1-cylohexene-1,2-dicarboximido)-4-fluorophenyl]carbamoyl}glycine, ethyl ester (2.45 g, 6.3 mmol) in toluene is treated with N-(chlorocarbonyl) isocyanate (0.77 g, 7.3 mmol), stirred at 60° C. for 12 hours and concentrated in vacuo to obtain a solid. The solid is dried in a vacuum oven at 85° C. for 24 hours to give the title product as a yellow solid (2.13 g, mp 135°–150° C.).

EXAMPLE 14

Preparation of 5-[3-(1-Cyclohexene-1,2-dicarboximido)-4-fluorophenyl]dihydro-2,4,6-trioxo-s-triazine-1,3(2H,4H)-diacetic acid, 1-tert-butyl, ethyl ester

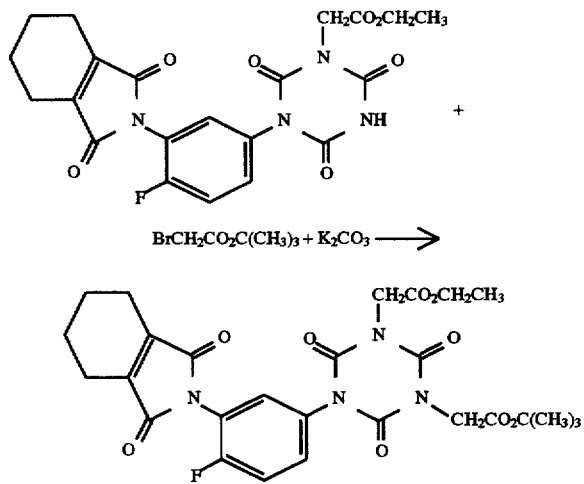

Tert-butyl bromoacetate (0.689 g, 3.5 mmol) and potassium carbonate (0.484 g, 3.5 mmol) are separately added to a solution of ethyl 3-[3-(1-cyclohexene-1,2-dicarboximido)-4-fluorophenyl]tetrahydro-2,4,6-trioxo-s-triazine-1(2H)-acetate (1.35 g, 2.9 mmol) in N,N-dimethylformamide. The resultant reaction mixture is stirred at room temperature for 18-hours, poured into water and extracted with ether. The organic extracts are combined, washed with brine, dried over anhydrous magnesium sulfate and concentrated in vacuo to give the title product as an amber solid (0.8 g, mp 95°–105° C.).

EXAMPLE 15

Preparation of Isopropyl 3-(2-chloro-4-fluorophenyl)tetrahydro-5-methyl-2,4,6-trioxo-s-triazine-1(2H)-acetate

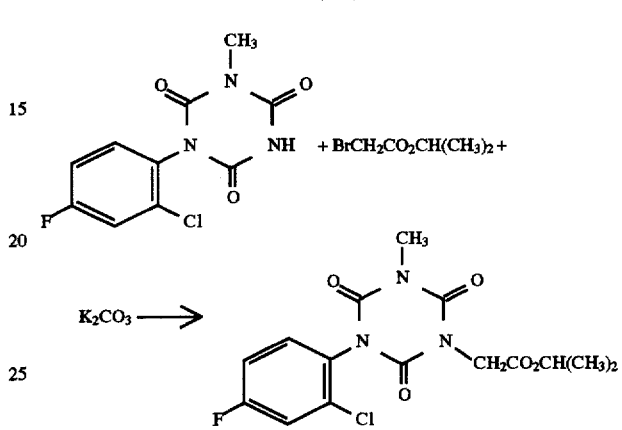

A mixture of 1-(2-chloro-4-fluorophenyl)-3-methyl-s-triazine-2,4,6(1H,3H,5H)-trione (40.9 g, 0.150 mol), potassium carbonate (31.1 g, 0.225 mol) and isopropyl bromoacetate (29.1 mL, 0.225 mol) in N,N-dimethylformamide is stirred at room temperature for 2 hours, poured into water and extracted with ethyl acetate. The organic extract is washed sequentially with water and brine, dried over anhydrous magnesium sulfate and concentrated in vacuo to obtain an oil. Flash column chromatography of the oil using silica gel and 0% to 10% ether in methylene chloride solutions gives the title product as a white solid (51.5 g, mp 127°–128° C.).

EXAMPLE 16

Preparation of 3-(2-Chloro-4-fluoro-5-nitrophenyl)tetrahydro-5-methyl-2,4,6-trioxo-s-triazine-1(2H)-acetic acid

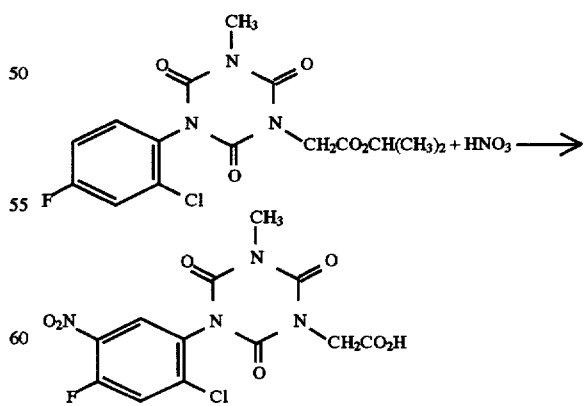

A solution of isopropyl 3-(2-chloro-4-fluorophenyl)tetrahydro-5-methyl-2,4,6-trioxo-s-triazine-1(2H)-acetate (48.7 g, 0.0508 mol) in concentrated sulfuric acid is cooled to 0° C., treated with 90% nitric acid (2.6 mL), stirred at room temperature overnight, treated with 90% nitric acid (1.0 mL), stirred for 4 hours, treated with 90% nitric acid (2.0 mL), stirred at room temperature overnight, treated with 90% nitric acid (1.0 mL), stirred for 1 hour and poured onto ice. The resultant aqueous solution is filtered to obtain a solid. A solution of the solid in ether is dried over anhydrous magnesium sulfate and concentrated in vacuo to give the title product as a yellow foam which is identified by NMR spectral analyses.

EXAMPLE 17

Preparation of Isopropyl 3-(2-chloro-4-fluoro-5-nitrophenyl)tetrahydro-5-methyl-2,4,6-trioxo-s-triazine-1(2H)-acetate

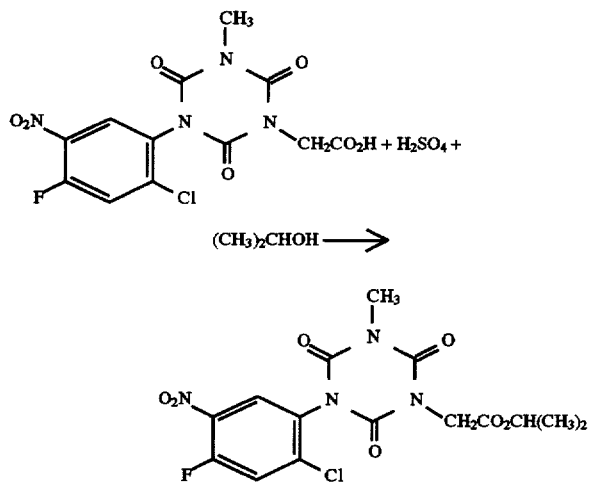

A solution of 3-(2-chloro-4-fluoro-5-nitrophenyl) tetrahydro-5-methyl-2,4,6-trioxo-s-triazine-1(2H)-acetic acid (43.6 g, 0.105 mol) and concentrated sulfuric acid (25 mL) in 2-propanol (300 mL) is refluxed for 12 hours, cooled to room temperature and filtered to obtain a solid. The solid is dried to give the title product as an off-white solid which is identified by NMR spectral analyses. The filtrate is partially concentrated in vacuo and poured over ice. The resultant aqueous mixture is extracted with ethyl acetate and the organic extract is dried over anhydrous magnesium sulfate and concentrated in vacuo to obtain an orange oil. Flash column chromatography of the oil using silica gel and 2.5% to 5% ether in methylene chloride solutions gives additional title product as a yellow foam.

EXAMPLE 18

Preparation of Isopropyl 3-(5-amino-2-chloro-4-fluorophenyl)tetrahydro-5-methyl-2,4,6-trioxo-s-triazine-1(2H)-acetate

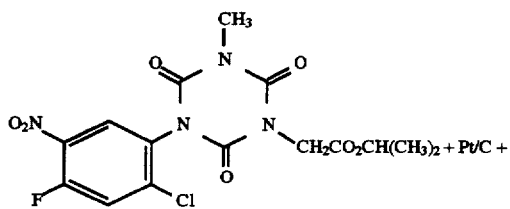

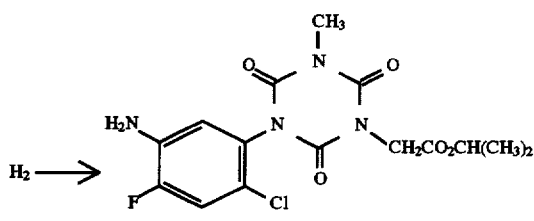

A mixture of isopropyl 3-(2-chloro-4-fluoro-5-nitrophenyl)tetrahydro-5-methyl-2,4,6-trioxo-s-triazine-1 (2H)-acetate (34.8 g, 0.0835 mol) and 5% platinum on carbon (3.48 g) in ethyl acetate is hydrogenated until about 90 psi of hydrogen is taken up. The reaction mixture is then filtered and concentrated in vacuo to obtain a foam. Column chromatography of the foam using silica gel and 10% to 20% ether in methylene chloride solutions gives a yellow foam which contains two compounds. A mixture of the foam and 5% platinum on carbon (3.5 g) in ethyl acetate is hydrogenated until 5 psi of hydrogen is taken up. The reaction mixture is then filtered and concentrated in vacuo to give the title product as a yellow foam which is identified by NMR spectral analyses.

EXAMPLE 19

Preparation of Isopropyl 3-(2-chloro-4-fluoro-5-isocyanatophenyl)tetrahydro-5-methyl-2,4,6-trioxo-s-triazine-1(2H)-acetate

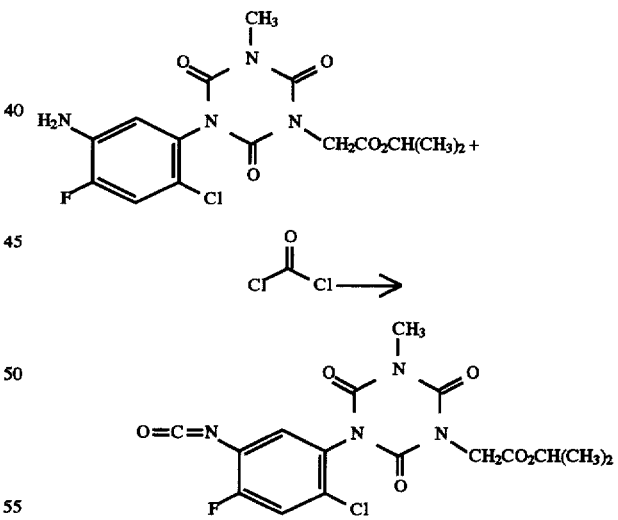

A mixture of isopropyl 3-(5-amino-2-chloro-4-fluorophenyl)tetrahydro-5-methyl-2,4,6-trioxo-s-triazine-1 (2H)-acetate (4.0 g, 0.0103 mol) in toluene is treated with a 1.93M solution of phosgene in toluene (19 mL), refluxed for 3 hours, cooled, partially concentrated in vacuo, diluted with toluene, partially concentrated in vacuo, diluted with toluene and concentrated in vacuo to give the title product as a yellow foam which is identified by $^1$H NMR spectral analysis.

EXAMPLE 20

Preparation of Ethyl 3-thiomorpholinecarboxylate

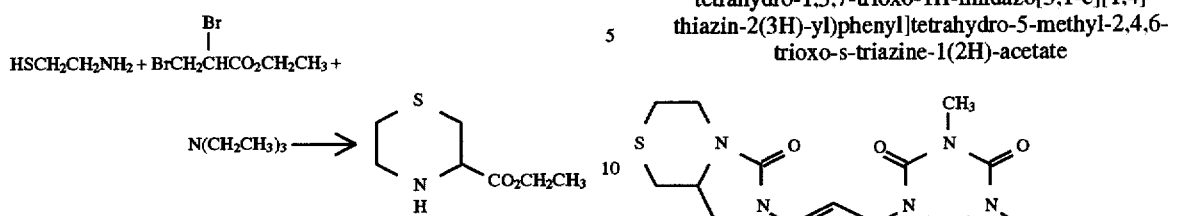

A warm solution of 2-aminoethanethiol (10.0 g, 0.130 mol) and triethylamine (36 mL, 0.260 mol) in chloroform is added over 5 minutes to a solution of ethyl 2,3-dibromopropionate (33.9 g, 0.130 mol) in a chloroform/toluene (1:1.6) solution. The reaction mixture is stirred at room temperature for 2.5 hours, filtered and concentrated in vacuo to obtain an orange liquid. The liquid is vacuum distilled to give the title product as a colorless liquid, bp 121°–124° C. at 3 mm Hg.

EXAMPLE 21

Preparation of Isopropyl 3-{2-chloro-4-fluoro-5-[5,6,8,8a-tetrahydro-1,3-dioxo-1H-imidazo[5,1c][1,4]thiazin-2(3H)-yl]phenyl}tetrahydro-5-methyl-2,4,6-trioxo-s-triazine-1(2H)-acetate

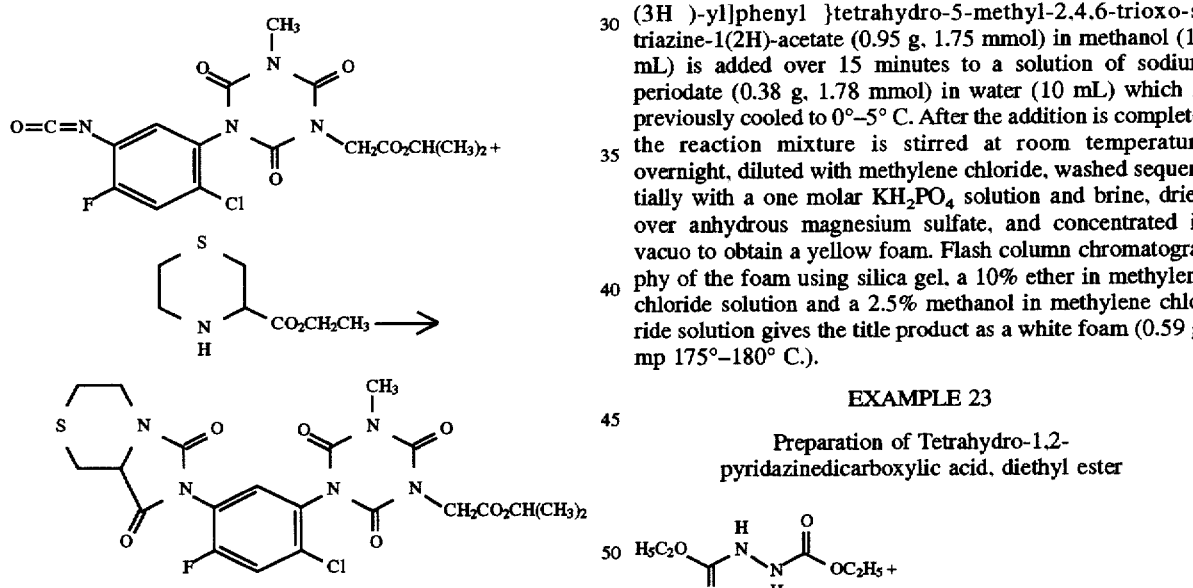

A solution of isopropyl 3-(2-chloro-4-fluoro-5-isocyanotophenyl)tetrahydro-5-methyl-2,4,6-trioxo-s-triazine-1(2H)-acetate (3.11 g, 7.5 mmol) and ethyl 3-thiomorpholinecarboxylate (1.44 g, 8.2 mmol) in toluene is stirred at room temperature for 1 hour, treated with several drops of ethyl 3-thiomorpholinecarboxylate, stirred at room temperature overnight and filtered to obtain a yellow solid. The resultant filtrate is dried and concentrated in vacuo to obtain an orange foam. The solid and foam are combined and chromatographed using silica gel and a 10% ether in methylene chloride solution to obtain an orange foam containing two compounds. Flash column chromatography of the foam using silica gel and a 15% ethyl acetate in methylene chloride solution gives the title product as an off-white foam, mp 147°–155° C.

EXAMPLE 22

Preparation of Isopropyl 3-[2-chloro-4-fluoro-5-tetrahydro-1,3,7-trioxo-1H-imidazo[5,1-c][1,4]thiazin-2(3H)-yl)phenyl]tetrahydro-5-methyl-2,4,6-trioxo-s-triazine-1(2H)-acetate

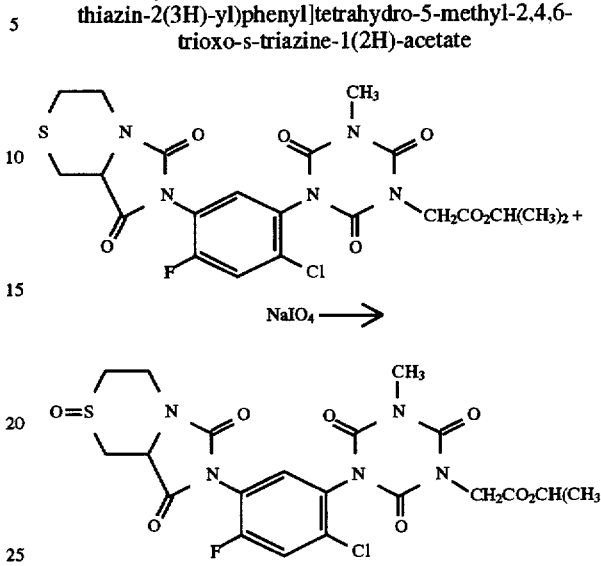

A mixture of isopropyl 3-{2-chloro-4-fluoro-5-[5,6,8,8a-tetrahydro-1,3-dioxo-1H-imidazo[5,1-c][1,4]thiazin-2(3H)-yl]phenyl}tetrahydro-5-methyl-2,4,6-trioxo-s-triazine-1(2H)-acetate (0.95 g, 1.75 mmol) in methanol (10 mL) is added over 15 minutes to a solution of sodium periodate (0.38 g, 1.78 mmol) in water (10 mL) which is previously cooled to 0°–5° C. After the addition is complete, the reaction mixture is stirred at room temperature overnight, diluted with methylene chloride, washed sequentially with a one molar $KH_2PO_4$ solution and brine, dried over anhydrous magnesium sulfate, and concentrated in vacuo to obtain a yellow foam. Flash column chromatography of the foam using silica gel, a 10% ether in methylene chloride solution and a 2.5% methanol in methylene chloride solution gives the title product as a white foam (0.59 g, mp 175°–180° C.).

EXAMPLE 23

Preparation of Tetrahydro-1,2-pyridazinedicarboxylic acid, diethyl ester

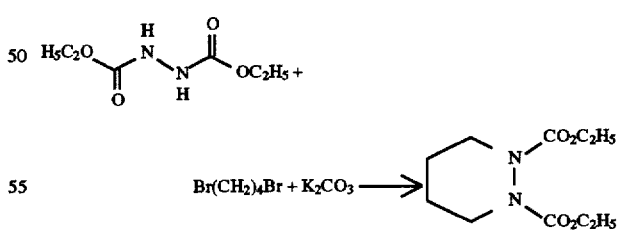

1,4-Dibromobutane (81.4 mL, 0.682 mol) is added over 1 hour to a mixture of 1,2-dicarbethoxyhydrazine (100 g, 0.568 mol) and potassium carbonate (158 g, 1.14 mol) in acetonitrile (600 mL). The resultant reaction mixture is refluxed for 6 hours, cooled to room temperature, and filtered. The filtrate is concentrated in vacuo to obtain a yellow liquid which is distilled under reduced pressure to give the title product as a colorless liquid (90.8 g, bp 115°–120° C. at 0.9 mm Hg).

EXAMPLE 24

Preparation of Hexahydropyridazine, Hydrochloride

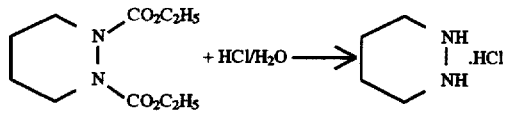

A solution of tetrahydro-1,2-pyridazinedicarboxylic acid, diethyl ester (45.0 g, 0.195 mol) in concentrated hydrochloric acid (190 mL) is refluxed overnight, and concentrated in vacuo to obtain a white solid. A mixture of the solid in acetonitrile is stirred for one hour and filtered to obtain a solid which is dried to give the title product as a white solid (19.5 g, mp 163° C.).

EXAMPLE 25

Preparation of Isopropyl 3-(2-chloro-4-fluoro-5-isothiocyanatophenyl)tetrahydro-5-methyl-2,4,6-trioxo-s-triazine-1(2H)-acetate

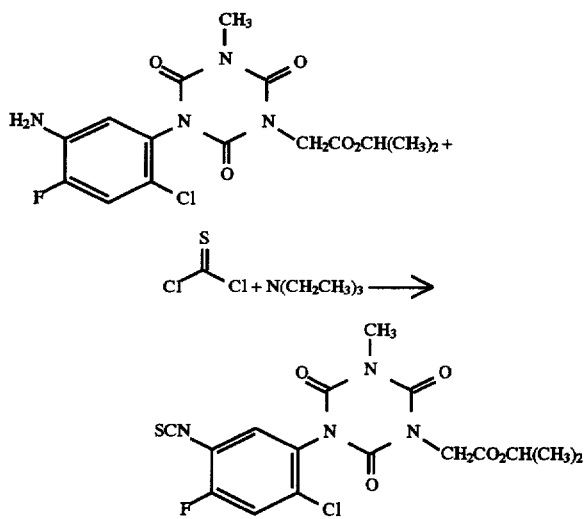

Thiophosgene (0.50 mL, 6.5 mmol) is added over 45 minutes to a solution of isopropyl 3-(5-amino-2-chloro-4-fluorophenyl)tetrahydro-5-methyl-2,4,6-trioxo-s-triazine-1(2H)-acetate (2.5 g, 6.5 mmol), and triethylamine (1.8 mL, 13.0 mmol) in tetrahydrofuran. The reaction mixture is stirred at room temperature for 4 hours, diluted with tetrahydrofuran, and filtered. The filtrate is concentrated in vacuo to give the title product as an orange oil which is identified by NMR spectral analyses.

EXAMPLE 26

Preparation of Isopropyl 3-{2-chloro-4-fluoro-5-[(tetrahydropyridazin-1(2H)-yl)thiocarboxamido]phenyl}tetrahydro-5-methyl-2,4,6-trioxo-s-triazine-1(2H)-acetate

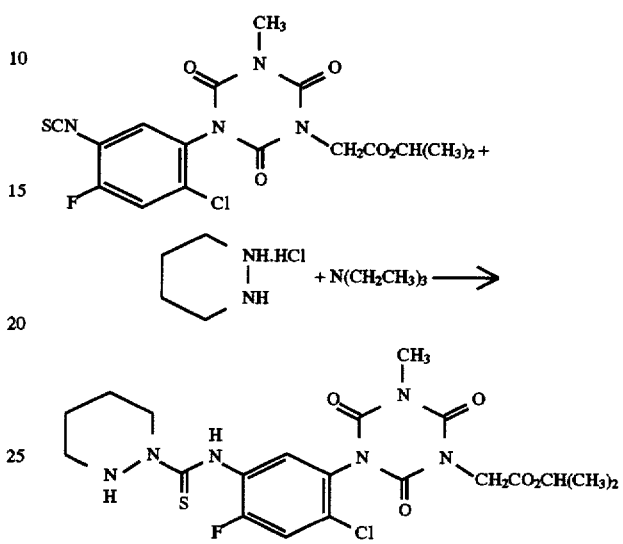

Triethylamine (2.5 mL, 18.2 mmol) is added dropwise to a mixture of isopropyl 3-(2-chloro-4-fluoro-5-isothiocyanatophenyl)tetrahydro-5-methyl-2,4,6-trioxo-s-triazine-1(2H)-acetate (2.79 g, 6.5 mmol), and hexahydropyridazine, hydrochloride (1.45 g, 9.1 mmol) in methanol while maintaining the reaction mixture temperature at 20°-25° C. After the addition is complete, the reaction mixture is stirred at room temperature overnight, partially concentrated in vacuo, and diluted with ethyl acetate. The organic phase is separated, washed sequentially with water and brine, dried over anhydrous magnesium sulfate, and concentrated in vacuo to obtain an orange foam. Flash column chromatography of the foam using silica gel and 2.5% to 10% ether in methylene chloride solutions gives the title product as a yellow foam (2.15 g, mp 105°–110° C.).

EXAMPLE 27

Preparation of Isopropyl 3-{2-chloro-4-fluoro-5-[(tetrahydro-3-oxo-1H,3H-[1,3,4]thiadiazolo[3,4-a]pyridazin-1-ylidene)amino]phenyl}tetrahydro-5-methyl-2,4,6-trioxo-s-triazine-1(2H)-acetate

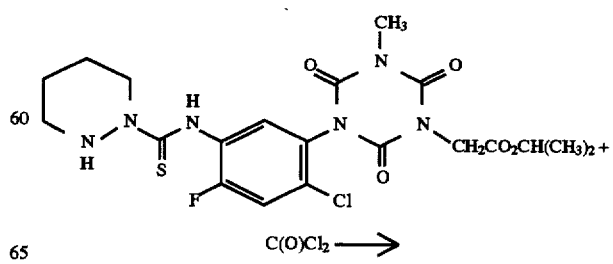

-continued

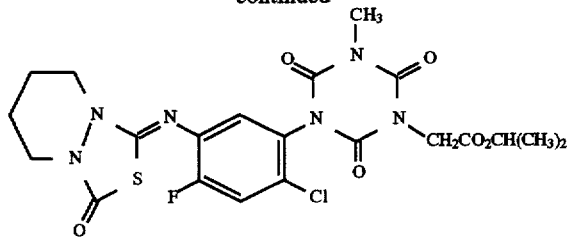

A solution of isopropyl 3-{2-chloro-4-fluoro-5-[(tetrahydropyridazin-1(2H)-yl)thiocarboxamido]phenyl} tetrahydro-5-methyl-2,4,6-trioxo-s-triazine-1(2H)-acetate (1.50 g, 2.9 mmol) in 1,2-dichloroethane is added over 30 minutes to a 20% phosgene in toluene solution (2.91 mL, 5.6 mmol) which is previously cooled to 0°–5° C. After the addition is complete, the reaction mixture is stirred at room temperature for 2 hours, washed sequentially with water and brine, dried over anhydrous magnesium sulfate, and concentrated in vacuo to obtain a yellow foam. Flash column chromatography of the foam using silica gel and 2.5% to 10% ether in methylene chloride solutions gives the title product as a white foam (1.18 g, mp 97°–107° C.).

EXAMPLE 28

Preparation of 4'-Chloro-2'-fluoroacetanilide

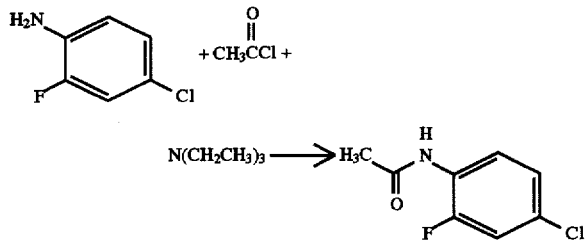

Acetyl chloride (24.2 mL, 0.34 mol) is added slowly to a solution of 4-chloro-2-fluoroaniline (49.4 g, 0.34 mol), and triethylamine (47 mL, 0.34 mol) in tetrahydrofuran while maintaining the reaction mixture temperature below 20° C. After the addition is complete, the reaction mixture is stirred overnight at room temperature, and poured into ethyl acetate. The organic solution is washed sequentially with water and brine, dried over anhydrous magnesium sulfate, and concentrated in vacuo to obtain an off-white solid. A mixture of the solid in ethanol is stirred for several minutes, and filtered to give the title product as a white solid.

EXAMPLE 29

Preparation of 4'-Chloro-2'-fluoro-5'-nitroacetanilide

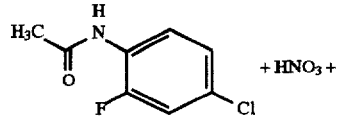 + HNO₃ +

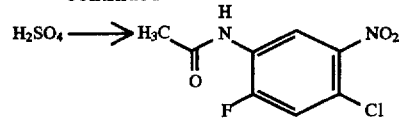

A mixture of 4'-chloro-2'-fluoroacetanilide (51 g, 0.272 mol) in concentrated sulfuric acid (100 mL) is cooled to 0° C., treated with nitric acid (90% real, 14 mL, 0.300 mol) over 45 minutes, stirred for 10 minutes, and poured onto ice. The resultant aqueous mixture is filtered to obtain a tan solid which is washed with water, dried overnight, and recrystallized from a chloroform/hexanes (17:1) solution to give the title product as a yellow solid.

EXAMPLE 30

Preparation of 5'-Amino-4'-chloro-2'-fluoroacetanilide

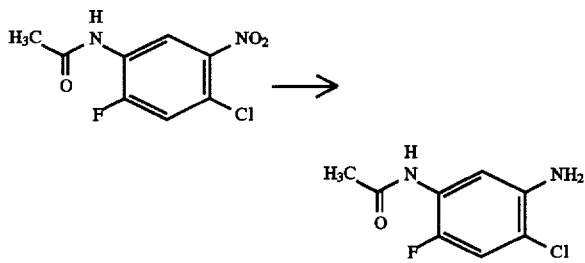

A mixture of 4'-chloro-2'-fluoro-5'-nitroacetanilide (35.2 g, 151 mmol), and 5% platinum on carbon (7.0 g, 20 wt/wt %) in an ethanol/tetrahydrofuran (2:1) solution is hydrogenated until 28 psi of hydrogen is taken up. The reaction mixture is then filtered, and concentrated in vacuo to give the title product as a tan solid which is identified by ¹H NMR spectral analysis.

EXAMPLE 31

Preparation of 1-(5-Acetamido-2-chloro-4-fluorophenyl)-3-(2-propynyl)urea

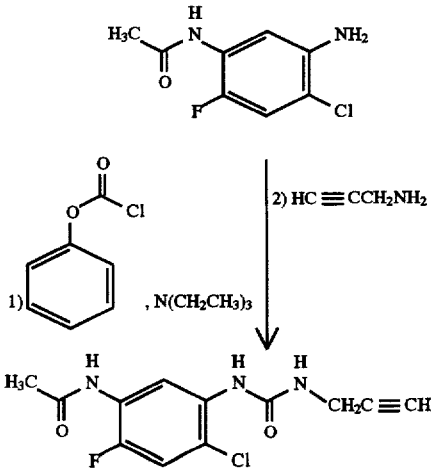

A solution of 5'-amino-4'-chloro-2'-fluoroacetanilide (11.25 g, 55.6 mmol), and triethylamine (7.70 mL, 55.6 mmol) in tetrahydrofuran is added dropwise to a stirred solution of phenylchloroformate (8.70 mL, 69.4 mmol) in tetrahydrofuran while maintaining the reaction mixture temperature at 25°–30° C. After the addition is complete, the reaction mixture is stirred at room temperature for 75 minutes, and poured into ethyl acetate. The organic mixture is washed sequentially with water, saturated sodium hydrogen carbonate solution and brine, dried over anhydrous magnesium sulfate, and concentrated in vacuo to obtain a tan solid. A solution of the solid in tetrahydrofuran is treated with propargylamine (9.52 mL, 139 mmol), refluxed for 1 hour, and poured into water. The aqueous mixture is filtered to obtain a solid which is washed sequentially with water, 0.5N hydrochloric acid and water, and dried overnight to give the title product as a beige solid.

EXAMPLE 32

Preparation of 4'-Chloro-2'-fluoro-5'-[hexahydro-2,4,6-trioxo-3-(2-propynyl)-s-triazin-1-yl]acetanilide

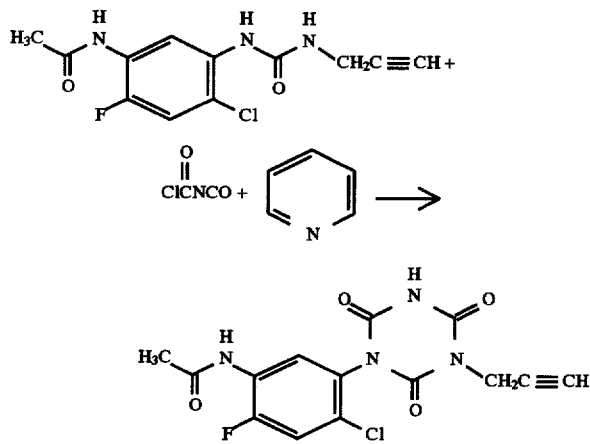

A mixture of 1-(5-acetamido-2-chloro-4-fluorophenyl)-3-(2-propynyl)urea (4.50 g, 15.9 mmol), and pyridine (2.56 mL, 31.8 mmol) in methylene chloride is treated with N-(chlorocarbonyl) isocyanate (1.92 mL, 23.9 mmol), stirred at room temperature overnight, refluxed for 90 minutes, cooled to room temperature, treated with additional pyridine (1.30 mL) and N-(chlorocarbonyl) isocyanate (1.92 mL), stirred for 10 minutes, cooled to room temperature, and filtered to obtain a solid. The solid is washed sequentially with water and hexanes, and dried to give the title product as a tan solid.

EXAMPLE 33

Preparation of 1-(5-Amino-2-chloro-4-fluorophenyl)-3-(2-propynyl)-s-triazine-2,4,6-(1H, 3H, 5H)-trione

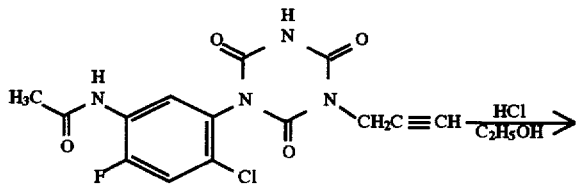

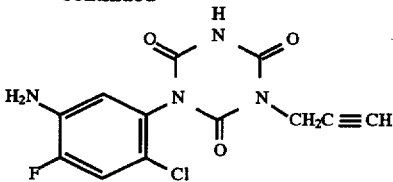

A mixture of 4'-chloro-2'-fluoro-5'-[hexahydro-2,4,6-trioxo-3-(2-propynyl)-s-triazin-1-yl]acetanilide (3.00 g, 8.5 mmol), and 3N hydrochloric acid (25 mL) in ethanol (50 mL) is refluxed for 3 hours, cooled to room temperature, and poured into ethyl acetate. 3N sodium hydroxide solution (25 mL) is added to the organic solution, and the phases are separated. The organic phase is washed sequentially with saturated sodium hydrogen carbonate solution and brine, and concentrated in vacuo to give the title product as a beige solid (2.17 g, mp 118°–121° C.).

EXAMPLE 34

Preparation of N-{4-Chloro-2-fluoro-5-[hexahydro-2,4,6-trioxo-3-(2-propynyl)-s-triazin-1-yl]phenyl}-1-cyclohexene-1,2-dicarboximide

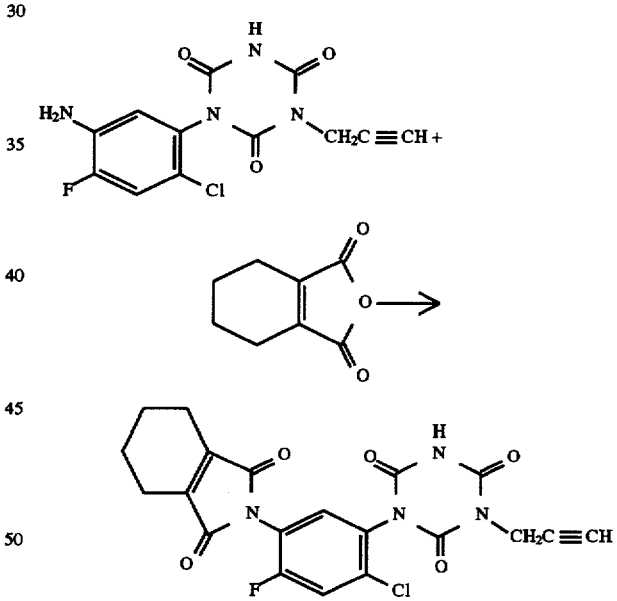

A solution of 1-(5-amino-2-chloro-4-fluorophenyl)-3-(2-propynyl)-s-triazine-2,4,6-(1H,3H,5H)-trione (1.50 g, 4.83 mmol), and 3,4,5,6-tetrahydrophthalic anhydride (0.73 g, 4.83 mmol) in acetic acid (3 mL) is heated at 100° C. for 5 hours, cooled, and poured into ethyl acetate. The organic mixture is washed sequentially with water, saturated sodium hydrogen carbonate solution and brine, dried over anhydrous magnesium sulfate, and concentrated in vacuo to obtain a yellow semi-solid. Flash column chromatography of the semi-solid using silica gel and an ethyl acetate/hexanes (1:2) solution gives the title product as a white solid (1.20 g, mp 127°–135° C.).

EXAMPLE 35

Preparation of N-(4-Chloro-2-fluorophenyl)-1-cyclohexene-1,2-dicarboximide

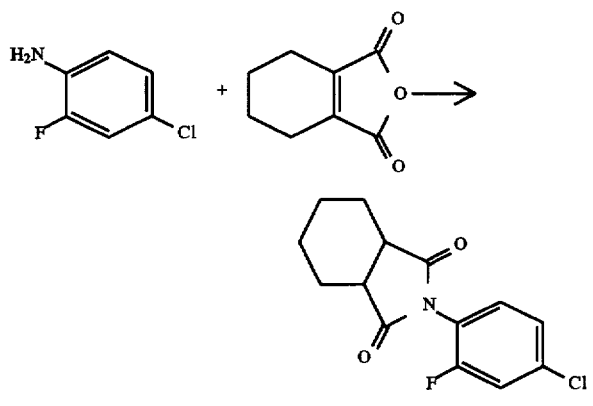

A mixture of 4-chloro-2-fluoroaniline (19.0 g, 130.6 mmol), and 3,4,5,6-tetrahydrophthalic anhydride (19.85 g, 130.6 mmol) in acetic acid (150 mL) is refluxed for 2 hours, treated with additional 4-chloro-2-fluoroaniline (3.0 g), refluxed for 90 minutes, stirred at room temperature overnight and poured into a water/ethyl acetate mixture. The organic phase is washed sequentially with water, saturated sodium hydrogen carbonate solution and brine, dried over anhydrous magnesium sulfate and concentrated in vacuo to obtain a purple oil. Flash column chromatography of the oil using silica gel and 15% to 20% ethyl acetate in hexanes solutions gives the title product as an off-white solid (25.3 g, mp 81°–82° C.).

EXAMPLE 36

Preparation of N-(4-Chloro-2-fluoro-5-nitrophenyl)-1-cyclohexene-1,2-dicarboximide

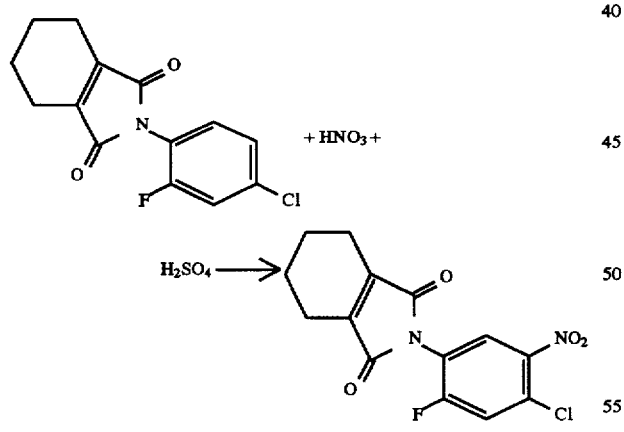

A mixture of N-(4-chloro-2-fluorophenyl)-1-cyclohexene-1,2-dicarboximide (24.4 g, 86.7 mmol) in sulfuric acid (150 mL) is cooled to −3° C., treated dropwise with nitric acid (70% real, 6.70 mL, 104 mmol) while maintaining the temperature at 0°–2° C., stirred at room temperature for 90 minutes, and poured onto ice. The aqueous mixture is stirred for several minutes, and filtered to obtain a solid which is washed with water and dried to give the title product as a white powder (28.6 g, mp 152°–155° C.).

EXAMPLE 37

Preparation of N-(5-Amino-4-chloro-2-fluorophenyl)-1-cyclohexene-1,2-dicarboximide

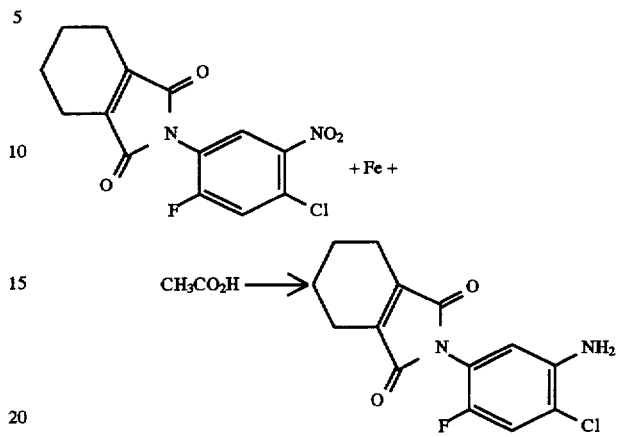

Iron powder (7.30 g, 130.7 mmol) is added portionwise to a mixture of N-(4-chloro-2-fluoro-5-nitrophenyl)-1-cyclohexene-1,2-dicarboximide (10.6 g, 32.7 mmol) in acetic acid (100 mL) at 65° C. After the addition is complete, the reaction mixture is stirred for 10 minutes, and filtered through diatomaceous earth. The filtrate is concentrated in vacuo to obtain a dark solid. A mixture of the solid in an ethyl acetate/saturated sodium hydrogen carbonate solution is filtered through diatomaceous earth, and the phases are separated. The organic phase is washed sequentially with saturated sodium hydrogen carbonate solution and brine, dried over anhydrous magnesium sulfate, and concentrated in vacuo to give the title product as a yellow solid.

EXAMPLE 38

Preparation of 1-Allyl-3-[2-chloro-5-(1-cyclohexene-1,2-dicarboximido)-4-fluorophenyl]urea

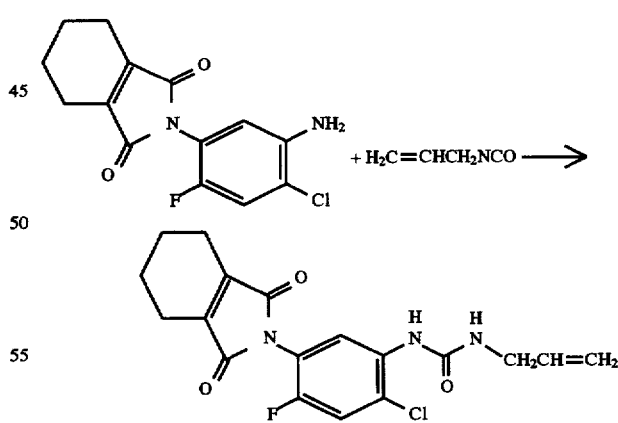

A mixture of N-(5-amino-4-chloro-2-fluorophenyl)-1-cyclohexene-1,2-dicarboximide (3.50 g, 11.9 mmol) in toluene (25 mL) is treated with allyl isocyanate (2.10 mL, 23.8 mmol), heated at 60° C. for 21 hours, treated with additional allyl isocyanate (0.53 mL), heated at 60° C. for 3 hours, cooled to 20°–30° C., and filtered to obtain a solid which is washed with hexanes to give the title product as a tan solid (3.15 g, mp 236°–238° C.).

EXAMPLE 39

Preparation of N-[5-(3-Allylhexahydro-2,4,6-trioxo-s-triazin-1-yl)-4-chloro-2-fluorophenyl]-1-cyclohexene-1,2-dicarboximide

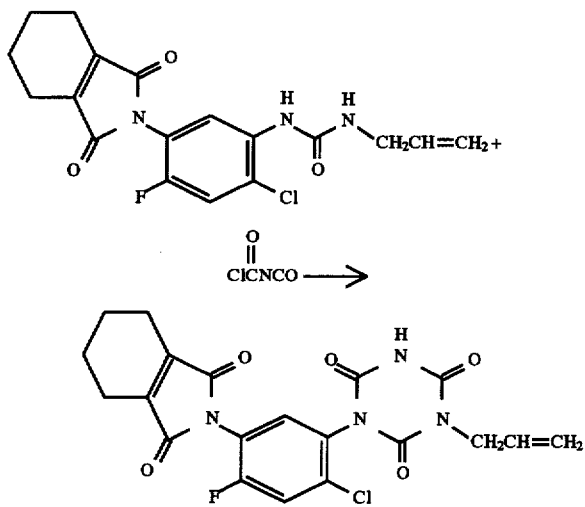

A mixture of 1-allyl-3-[2-chloro-5-(1-cyclohexene-1,2-dicarboximido)-4-fluorophenyl]urea (2.34 g, 6.21 mmol) in toluene (25 mL) is treated with N-(chlorocarbonyl) isocyanate (0.75 mL, 9.31 mmol), stirred at 60° C. for 3 hours, cooled to room temperature, and concentrated in vacuo to obtain an oil. Flash column chromatography of the oil using silica gel and an ethyl acetate/hexanes (2:3) solution gives the title product as a white solid (2.6 g, mp 130°–145° C.).

EXAMPLE 40

Preparation of N-{5-[3-Allylhexahydro-2,4,6-trioxo-5-(2-propynyl)-s-triazin-1-yl]-4-chloro-2-fluorophenyl}-1-cyclohexene-1,2-dicarboximide

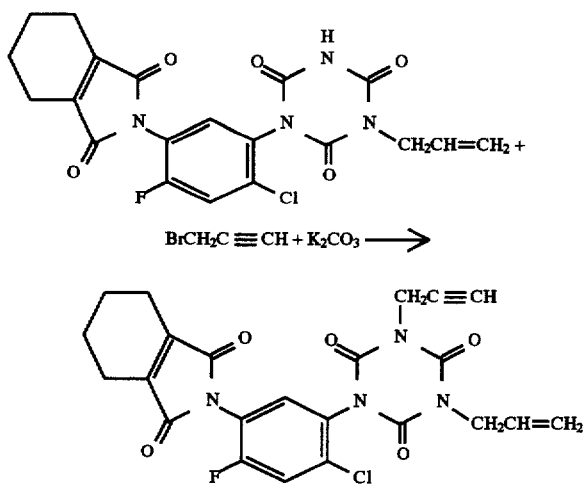

Propargyl bromide (0.37 mL, 3.36 mmol) is added to a mixture of N-[5-(3-allylhexahydro-2,4,6-trioxo-s-triazin-1-yl)-4-chloro-2-fluorophenyl]-1-cyclohexene-1,2-dicarboximide (1.00 g, 2.24 mmol), and potassium carbonate (0.62 g, 4.48 mmol) in N,N-dimethylformamide. The reaction mixture is stirred for 7 hours, and poured into ethyl acetate. The organic solution is washed sequentially with water and brine, dried over anhydrous magnesium sulfate, and concentrated in vacuo to obtain a yellow oil. Flash column chromatography of the oil using silica gel and an ethyl acetate/hexanes (1:4) solution gives the title product as a white solid (0.60 g, mp 107°–114° C.).

Using essentially the same procedure, but substituting allyl bromide for propargyl bromide, N-[4-chloro-5-(3,5-diallylhexahydro-2,4,6-trioxo-s-triazin-1-yl)-2-fluorophenyl]-1-cyclohexene-1,2-dicarboximide is obtained as a white solid, mp 80°–85° C.

EXAMPLE 41

Preparation of Isopropyl 3-[2-chloro-4-fluoro-5-(3-fluorophthalimido)phenyl]tetrahydro-5-methyl-2,4,6-trioxo-s-triazine-1(2H)-acetate

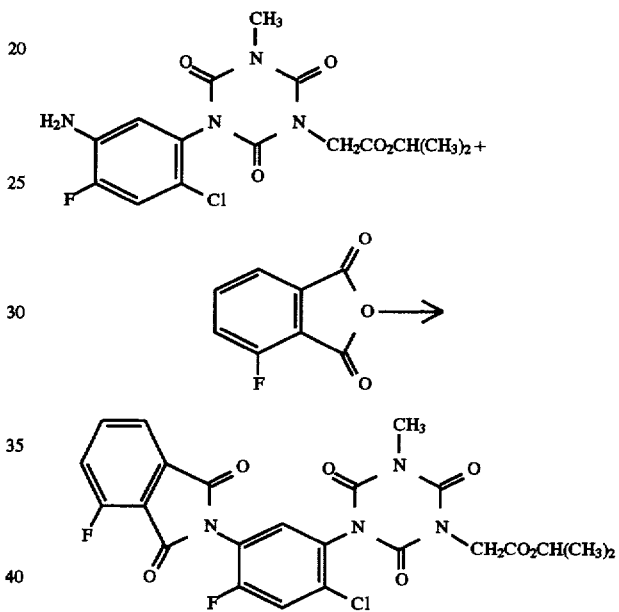

A solution of isopropyl 3-(5-amino-2-chloro-4-fluorophenyl)tetrahydro-5-methyl-2,4,6-trioxo-s-triazine-1(2H)-acetate (1.0 g, 2.6 mmol) and 3-fluorophthalic anhydride (0.51 g, 3.1 mmol) in acetic acid is refluxed for 6 hours, stirred at room temperature for several days and poured onto ice. The resultant aqueous mixture is filtered to obtain a solid. The solid is dried and chromatographed (silica gel/2.5% ether in methylene chloride solution) to give the title product as a yellow foam, mp 119°–125° C.

EXAMPLE 42

Postemergence Herbicidal Evaluation of Test Compounds

The postemergence herbicidal activity of the compounds of the present invention is demonstrated by the following tests, wherein a variety of dicotyledonous and monocotyledonous plants are treated with test compounds, dispersed in aqueous acetone mixtures. In the tests, seedling plants are grown in jiffy flats for about two weeks. The test compounds are dispersed in 50/50 acetone/water mixtures containing 0.5% TWEEN®20, a polyoxyethylene sorbitan monolaurate surfactant of Atlas Chemical Industries, in sufficient quantities to provide the equivalent of about 0.125 kg to 0.500 kg per hectare of active compound when applied to the plants through a spray nozzle operating at 40 psi for a predetermined time. After spraying, the plants are placed on greenhouse benches and are cared for in the usual manner, commensurate with conventional greenhouse practices. From four to five weeks after treatment, the seedling plants are examined and rated according to the rating system set forth below. Data obtained are reported in Table I below. Where more than one test is involved for a given compound, the data are averaged.

Plant species employed in these evaluations are reported by header abbreviation, common name and scientific name.

Compounds employed in this postemergence herbicidal evaluation and in the preemergence evaluation in the following example are given a compound number and identified by name. Data in Table I are reported by compound number.

Herbicide Rating Scale

Results of herbicide evaluation are expressed on a rating scale (0–9). The scale is based upon a visual observation of plant stand, vigor, malformation, size, chlorosis and overall plant appearance as compared with a control.

| Rating | Meaning | Control Compared to Check |
|---|---|---|
| 9 | Complete kill | 100 |
| 8 | Approaching Complete Kill | 91–99 |
| 7 | Good Herbicidal Effect | 80–90 |
| 6 | Herbicidal Effect | 65–79 |
| 5 | Definite Injury | 45–64 |
| 4 | Injury | 30–44 |
| 3 | Moderate Effect | 16–29 |
| 2 | Slight Effect | 6–15 |
| 1 | Trace Effect | 1–5 |
| 0 | No Effect | 0 |
| — | No Evaluation | |

PLANT SPECIES EMPLOYED IN HERBICIDAL EVALUATIONS

| Header Abb. | Common Name | Scientific Name |
|---|---|---|
| ABUTH | Velvetleaf | *ABUTILON THEOPHRASTI*, MEDIC. |
| AMBEL | Ragweed, Common | *AMBROSIA ARTEMISITFOLIA*, L. |
| CASOB | Sicklepod | *CASSIA OBTUSIFOLIA*, L. |
| CHEAL | Lambsquarters, Common | *CHENOPODIUM ALBUM*, L. |
| IPOSS | Morningglory Spp. | *IPOMOEA SPP.* |
| GALAP | Galium | *GALIUM APARINE* |
| ECHCG | Barnyardgrass | *ECHINOCHLOA CRUS-GALLI*, (L) BEAU |
| SETVI | Foxtail, Green | *SETARIA VIRIDIS*, (L) BEAU |
| GLXMAW | Soybean, Williams | *GLYCINE MAX(L)MERR.* CV. WILLIAMS |
| ORYSAT | Rice, Tebonnet | *ORYZA SATIVA*, L. TEBONNET |
| TRZAWO | Wheat, Winter, CV. APOLLO | *TRITICUM AESTIVUM*, CV. APOLLO |
| ZEAMX | Corn, Field | *ZEA MAYS* L. |

COMPOUNDS EVALUATED AS HERBICIDAL AGENTS

| Compound Number | |
|---|---|
| 1 | Methyl 3-[2-Chloro-5-(1-cyclohexene-1,2-dicarboximido)-4-fluorophenyl]tetrahydro-5-methyl-2,4,6-trioxo-s-triazine-1(2H)-acetate |
| 2 | Tert-butyl 3-[2-chloro-5-(1-cyclohexene-1,2-dicarboximido)-4-fluorophenyl]tetrahydro-5-methyl-2,4,6-trioxo-S-triazine-1(2H)-acetate |
| 3 | 3-[2-Chloro-5-(1-cyclohexene-1,2-dicarboximido)-4-fluorophenyl]tetrahydro-5-methyl-2,4,6-trioxo-s-triazine-1(2H)-acetic acid |
| 4 | Isopropyl 3-[2-chloro-5-(1-cyclohexene-1,2-dicarboximido)-4-fluorophenyl]tetrahydro-5-methyl-2,4,6-trioxo-s-triazine-1(2H)-acetate |
| 5 | Methyl 3-(5-(1-cyclohexene-1,2-dicarboximido)-2-fluorophenyl]tetrahydro-5-methyl-2,4,6-trioxo-s-triazine-1(2H)-acetate |
| 6 | Methyl 3-[2,4-dichloro-5-(1-cyclohexene-1,2-dicarboximido)phenyl]tetrahydro-5-methyl-2,4,6-trioxo-s-triazine-1(2H)-acetate |
| 7 | Tert-butyl 3-[2,4-dichloro-5-(1-cyclohexene-1,2-dicarboximido)phenyl]tetrahydro-5-methyl-2,4,6-trioxo-s-triazine-1(2H)-acetate |
| 8 | 5-[3-(1-Cyclohexene-1,2-dicarboximido)-4-fluorophenyl]dihydro-2,4,6-trioxo-s-triazine-1,3(2H,4H)-diacetic acid, 1-tert-butyl, ethyl ester |
| 9 | Ethyl 3-[3-(1-cyclohexene-1,2-dicarboximido)-4-fluorophenyl]tetrahydro-2,4,6-trioxo-s-triazine-1(2H)-acetate |
| 10 | Methyl 3-[5-(1-cyclohexene-1,2-dicarboximido)-2,4-difluorophenyl]-5-methyl-2,4,6-trioxo-s-triazine-1(2H)-acetate |
| 11 | Isopropyl 3-[2-chloro-4-fluoro-5-(3-fluorophthalimido)phenyl]tetrahydro-5-methyl-2,4,6-trioxo-s-triazine-1(2H)-acetate |
| 12 | Isopropyl 3-{2-chloro-4-fluoro-5-[5,6,8,8a-tetrahydro-1,3-dioxo-1H-imidazo[5,1c][1,4]-thiazin-2(3H)-yl]phenyl}tetrahydro-5-methyl-2,4,6-trioxo-s-triazine-1(2H)-acetate |
| 13 | Isopropyl 3-(2-chloro-4-fluoro-5-[(tetrahydro-3-oxo-1H,3H-[1,3,4]thiadiazolo[3,4-a]pyridazin-1-ylidene)amino]phenyl}tetrahydro-5-methyl-2,4,6-trioxo-s-triazine-1(2H)-acetate |
| 14 | Isopropyl 3-[2-chloro-4-fluoro-5-(tetrahydro-1,3,3-trioxo-1H-imidazo[5,1c][1,4]-thiazin-2(3H)-yl)phenyl]tetrahydro-5-methyl-2,4,6-trioxo-s-triazine-1(2H)-acetate |
| 15 | N-{4-Chloro-2-fluoro-5-[hexahydro-2,4,6-trioxo-3-(2-propynyl)-s-triazin-1-yl]-phenyl}-1-cyclohexene-1,2-dicarboximide |
| 16 | N-{4-Chloro-2-fluoro-5-[hexahydro-3-methyl-2,4,6-trioxo-5-(2-propynyl)-s-triazin-1-yl]phenyl}-1-cyclohexene-1,2-dicarboximide |
| 17 | N-[5-(3-Allylhexahydro-5-methyl--2,4,6-trioxo-s-triazin-1-yl)-4-chloro-2-fluorophenyl]-1-cyclohexene-1,2-dicarboximide |
| 18 | N-[5-(3-Allylhexahydro-2,4,6-trioxo-s-triazin-1-yl)-4-chloro-2-fluorophenyl]-1-cyclohexene-1,2-dicarboximide |
| 19 | N-[4-Chloro-5-(3,5-diallylhexahydro-2,4,6-trioxo-s-triazin-1-yl)-2-fluorophenyl]-1-cyclohexene-1,2-dicarboximide |
| 20 | N-{5-[3-Allylhexahydro-2,4,6-trioxo-5-(2-propynyl)-s-triazin-1-yl]-4-chloro-2-fluorophenyl}-1-cyclohexene-1,2-dicarboximide |

TABLE I

Postemergence Herbicidal Evaluations of Test Compounds

| Compound Number | Rate (kg/ha) | ABUTH | AMBEL | CASOB | CHEAL | IPOSS | GALAP | ECHCG | SETVI | GLXMAW | ORYSAT | TRZAWO | ZEAMX |
|---|---|---|---|---|---|---|---|---|---|---|---|---|---|
| 1 | 0.500 | 9.0 | 9.0 | 7.0 | 4.0 | 8.0 | 4.0 | 1.0 | 2.0 | 7.0 | 4.5 | 5.5 | 5.0 |
|   | 0.250 | 9.0 | 9.0 | 7.0 | 3.0 | 9.0 | 3.0 | 0.0 | 00 | 6.5 | 4.5 | 5.5 | 4.5 |
|   | 0.125 | 9.0 | 7.0 | 5.0 | 2.0 | 8.0 | 3.0 | 0.0 | 0.0 | 5.0 | 3.5 | 4.0 | 4.5 |
| 2 | 0.500 | 9.0 | 8.5 | 7.0 | 8.0 | 7.0 | 8.5 | 0.5 | 0.5 | 5.5 | 4.5 | 4.5 | 4.3 |
|   | 0.250 | 9.0 | 7.5 | 5.5 | 7.5 | 8.0 | 9.0 | 0.0 | 0.0 | 5.5 | 3.8 | 4.3 | 4.0 |
|   | 0.125 | 9.0 | 6.0 | 5.0 | 5.5 | 7.5 | 7.0 | 0.0 | 0.0 | 4.3 | 3.0 | 3.5 | 3.3 |
| 3 | 0.500 | 2.0 | 3.0 | 3.0 | 2.0 | 5.0 | 2.0 | 0.0 | 0.0 | 4.0 | 4.0 | 5.0 | 4.5 |
|   | 0.250 | 0.0 | 3.0 | 2.0 | 2.0 | 4.0 | 2.0 | 0.0 | 0.0 | 4.5 | 4.0 | 4.5 | 4.5 |
|   | 0.125 | 1.0 | 1.0 | 2.0 | 0.0 | 2.0 | 0.0 | 0.0 | 0.0 | 3.5 | 3.0 | 4.0 | 4.0 |
| 4 | 0.500 | 9.0 | 9.0 | 9.0 | 8.0 | 8.0 | 8.0 | 2.0 | 3.0 | 7.0 | 4.0 | 5.0 | 4.5 |
|   | 0.250 | 9.0 | 7.0 | 8.0 | 8.0 | 8.0 | 7.0 | 0.0 | 1.0 | 6.0 | 4.0 | 4.5 | 4.5 |
|   | 0.125 | 9.0 | 5.0 | 7.0 | 6.0 | 7.0 | 6.0 | 0.0 | 0.0 | 5.0 | 4.0 | 4.5 | 4.5 |
| 5 | 0.500 | 2.0 | 2.0 | 0.0 | 0.0 | 5.0 | 3.0 | 0.0 | 2.0 | 4.5 | 2.0 | 2.0 | 3.5 |
|   | 0.250 | 0.0 | 2.0 | 0.0 | 0.0 | 2.0 | 2.0 | 0.0 | 0.0 | 4.5 | 2.0 | 1.0 | 2.5 |
|   | 0.125 | 2.0 | 2.0 | 0.0 | 0.0 | 3.0 | 0.0 | 0.0 | 0.0 | 4.0 | 1.5 | 1.0 | 2.5 |
| 6 | 0.500 | 8.0 | 5.0 | 4.5 | 7.5 | 7.0 | 4.5 | 1.0 | 2.0 | 5.0 | 2.8 | 3.5 | 3.8 |
|   | 0.250 | 6.5 | 4.5 | 4.5 | 8.0 | 6.0 | 4.0 | 1.0 | 1.0 | 4.3 | 2.8 | 3.3 | 3.8 |
|   | 0.125 | 6.0 | 3.5 | 3.0 | 5.5 | 5.5 | 3.0 | 0.0 | 0.0 | 4.0 | 2.0 | 2.5 | 3.0 |
| 7 | 0.500 | 7.5 | 7.5 | 6.0 | 8.0 | 7.0 | 6.0 | 1.0 | 1.0 | 5.0 | 3.0 | 3.3 | 4.8 |
|   | 0.250 | 9.0 | 7.5 | 6.0 | 8.0 | 6.0 | 4.5 | 1.0 | 1.0 | 5.0 | 3.0 | 2.5 | 4.8 |
|   | 0.125 | 7.0 | 6.0 | 5.0 | 7.0 | 5.5 | 2.5 | 0.0 | 0.0 | 4.5 | 2.3 | 2.5 | 3.8 |
| 8 | 0.500 | 3.0 | 3.0 | 0.0 | 2.0 | 3.0 | 4.0 | 0.0 | 0.0 | 2.0 | 1.5 | 0.5 | 0.5 |
|   | 0.250 | 3.0 | 2.0 | 0.0 | 2.0 | 2.0 | 4.0 | 0.0 | 0.0 | 2.5 | 1.5 | 0.5 | 0.5 |
|   | 0.125 | 2.0 | 0.0 | 0.0 | 0.0 | 3.0 | 2.0 | 0.0 | 0.0 | 1.5 | 1.5 | 0.5 | 0.0 |
| 9 | 0.500 | 5.4 | 2.0 | 0.0 | 2.0 | 4.0 | 3.0 | 0.0 | 0.0 | 3.5 | 2.0 | 2.0 | 1.5 |
|   | 0.250 | 4.0 | 2.0 | 0.0 | 0.0 | 2.0 | 2.0 | 0.0 | 0.0 | 2.5 | 2.0 | 2.0 | 1.5 |
|   | 0.125 | 3.0 | 0.0 | 0.0 | 0.0 | 2.0 | 2.0 | 0.0 | 0.0 | 2.0 | 1.5 | 1.0 | 1.0 |
| 10 | 0.500 | 9.0 | 6.0 | 0.0 | 0.0 | 5.0 | 0.0 | 0.0 | 0.0 | 4.5 | 4.0 | 4.0 | 4.0 |
|    | 0.250 | 6.0 | 4.0 | 2.0 | 2.0 | 4.0 | 2.0 | 0.0 | 0.0 | 4.0 | 3.5 | 3.5 | 4.0 |
|    | 0.125 | 6.0 | 4.0 | 1.0 | 0.0 | 8.0 | 0.0 | 0.0 | 0.0 | 3.5 | 3.0 | 3.5 | 4.0 |
| 11 | 0.500 | 7.0 | 9.0 | 6.0 | 9.0 | 6.0 | 3.0 | 3.0 | 3.0 | 5.5 | 2.0 | 1.0 | 3.0 |
|    | 0.250 | 6.0 | 6.0 | 4.0 | 9.0 | 4.0 | 2.0 | 3.0 | 3.0 | 4.5 | 2.0 | 0.5 | 2.5 |
|    | 0.125 | 9.0 | 9.0 | 4.0 | 9.0 | 3.0 | 1.0 | 3.0 | 2.0 | 4.0 | 1.5 | 0.5 | 2.5 |
| 12 | 0.500 | 9.0 | 9.0 | 9.0 | 9.0 | 9.0 | 8.0 | 3.0 | 4.0 | 6.5 | 3.0 | 2.5 | 5.0 |
|    | 0.250 | 9.0 | 9.0 | 9.0 | 9.0 | 9.0 | 8.0 | 3.0 | 3.0 | 5.5 | 3.5 | 2.5 | 4.5 |
|    | 0.125 | 9.0 | 9.0 | 9.0 | 9.0 | 7.0 | 7.0 | 2.0 | 2.0 | 6.5 | 3.0 | 2.5 | 4.0 |
| 13 | 0.500 | 9.0 | 9.0 | 9.0 | 9.0 | 9.0 | 8.0 | 0.0 | 1.0 | 65 | 4.0 | 3.5 | 4.0 |
|    | 0.250 | 9.0 | 7.0 | 9.0 | 9.0 | 8.0 | 9.0 | 0.0 | 1.0 | 5.5 | 4.5 | 3.5 | 3.5 |
|    | 0.125 | 9.0 | 6.0 | 7.0 | 8.0 | 7.0 | 7.0 | 0.0 | 1.0 | 5.5 | 4.0 | 3.5 | 3.5 |
| 14 | 0.500 | 6.0 | 6.0 | 5.0 | 7.0 | 4.0 | 4.0 | 0.0 | 1.0 | 4.5 | 4.5 | 2.0 | 1.5 |
|    | 0.250 | 5.0 | 5.0 | 5.0 | 8.0 | 3.0 | 4.0 | 0.0 | 1.0 | 4.0 | 2.5 | 2.0 | 1.0 |
|    | 0.125 | 3.0 | 4.0 | 5.0 | 6.0 | 3.0 | 3.0 | 0.0 | 1.0 | 3.5 | 2.5 | 2.0 | 1.5 |
| 15 | 0.500 | 2.0 | 5.0 | 1.0 | 9.0 | 2.0 | 9.0 | 4.0 | 5.0 | 6.0 | 2.0 | 5.0 | 6.0 |
|    | 0.250 | 0.0 | 5.0 | 0.0 | 8.0 | 0.0 | 5.0 | 3.0 | 4.0 | 4.0 | 0.0 | 3.0 | 5.0 |
|    | 0.125 | 0.0 | 3.0 | 0.0 | 8.0 | 0.0 | 5.0 | 3.0 | 4.0 | 2.0 | 0.0 | 2.0 | 3.0 |
| 16 | 0.500 | 4.0 | 4.0 | 3.0 | 5.0 | 6.0 | 4.0 | 0.0 | 0.0 | 4.0 | 4.5 | 4.0 | 4.0 |
|    | 0.250 | 3.0 | 4.0 | 2.0 | 5.0. | 6.0 | 4.0 | 0.0 | 0.0 | 3.5 | 4.5 | 3.5 | 3.5 |
|    | 0.125 | 2.0 | 2.0 | 1.0 | 4.0 | 4.0 | 3.0 | 0.0 | 0.0 | 3.0 | 3.0 | 2.5 | 2.5 |
| 17 | 0.500 | 8.0 | 7.0 | 2.0 | 8.0 | 5.0 | 4.0 | 0.0 | 2.0 | 5.5 | 3.5 | 3.0 | 4.0 |
|    | 0.250 | 6.0 | 5.0 | 3.0 | 6.0 | 3.0 | 3.0 | 0.0 | 1.0 | 4.0 | 2.5 | 2.5 | 3.0 |
|    | 0.125 | 6.0 | 4.0 | 2.0 | 5.0 | 3.0 | 2.0 | 0.0 | 1.0 | 3.0 | 2.5 | 2.0 | 2.5 |
| 18 | 0.500 | 6.0 | 5.0 | 4.0 | 7.0 | 4.0 | 6.0 | 4.0 | 4.0 | 5.5 | 4.0 | 4.5 | 5.0 |
|    | 0.250 | 1.0 | 3.0 | 3.0 | 7.0 | 2.0 | 2.0 | 0.0 | 2.0 | 3.5 | 3.0 | 3.5 | 3.5 |
|    | 0.125 | 0.0 | 1.0 | 2.0 | 6.0 | 2.0 | 0.0 | 0.0 | 1.0 | 4.0 | 2.0 | 2.5 | 2.0 |
| 19 | 0.500 | 3.0 | 6.0 | 2.0 | 7.0 | 3.0 | 4.0 | 0.0 | 0.0 | 1.0 | 2.0 | 2.0 | 3.0 |
|    | 0.250 | 3.0 | 5.0 | 0.0 | 6.0 | 3.0 | 4.0 | 0.0 | 0.0 | 1.0 | 2.0 | 2.0 | 2.0 |
|    | 0.125 | 1.0 | 4.0 | 0.0 | 4.0 | 1.0 | 3.0 | 0.0 | 0.0 | 1.0 | 2.0 | 2.0 | 1.0 |
| 20 | 0.500 | 6.0 | 6.0 | 2.0 | 8.0 | 6.0 | 8.0 | 0.0 | 0 0 | 2.0 | 2.0 | 2.0 | 3.0 |
|    | 0.250 | 6.0 | 5.0 | 0.0 | 7.0 | 4.0 | 2.0 | 0.0 | 0.0 | 1.0 | 2.0 | 2.0 | 2.0 |
|    | 0.125 | 3.0 | 4.0 | 0.0 | 7.0 | 2.0 | 2.0 | 0.0 | 0.0 | 1.0 | 2.0 | 1.0 | 2.0 |

EXAMPLE 43

Preemergence Herbicidal Evaluation of Test Compounds

The preemergence herbicidal activity of the test compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.125 to 0.50 kg per hectare of test compound per cup. The treated cups are then placed on greenhouse benches, watered and cared for in accordance with conventional greenhouse procedures. From four to five weeks after treatment, the tests are terminated and each cup is examined and rated according to the rating system provided in Example 42.

The data obtained are reported in Table II below. The compounds evaluated are reported by compound number given in Example 42.

X and Y are each independently hydrogen, halogen, nitro, cyano, $C_1-C_4$alkyl, $C_1-C_4$haloalkyl, $C_1-C_4$alkoxy, $C_1-C_4$haloalkoxy or $S(O)_mR_2$;

TABLE II

Preemergence Herbicidal Evaluations Of Test Compounds

| Compound Number | Rate (kg/ha) | ABUTH | AMBEL | CASOB | CHEAL | IPOSS | GALAP | ECHCG | SETVI | GLXMAW | ORYSAT | TRZAWO | ZEAMX |
|---|---|---|---|---|---|---|---|---|---|---|---|---|---|
| 1 | 0.500 | 8.0 | 4.0 | 6.0 | 9.0 | 0.0 | 0.0 | 3.0 | 4.0 | 0.0 | 0.0 | 0.0 | 0.0 |
|   | 0.250 | 9.0 | 0.0 | 5.0 | 9.0 | 2.0 | 0.0 | 0.0 | 2.0 | 0.0 | 0.0 | 0.0 | 0.0 |
|   | 0.125 | 0.0 | 0.0 | 5.0 | 9.0 | 0.0 | — | 0.0 | 2.0 | 0.0 | 0.0 | 0.0 | 0.0 |
| 2 | 0.500 | 9.0 | 7.0 | 8.0 | 9.0 | 6.0 | 6.0 | 0.0 | 0.0 | 0.0 | 1.0 | 1.0 | 2.0 |
|   | 0.250 | 9.0 | 5.0 | 3.0 | 9.0 | 6.0 | 9.0 | 0.0 | 0.0 | 0.0 | 1.0 | 1.0 | 0.0 |
|   | 0.125 | 7.0 | 5.0 | 4.0 | 9.0 | 6.0 | 7.0 | 0.0 | 0.0 | 0.0 | 0.0 | 1.0 | 0.0 |
| 3 | 0.500 | 0.0 | 0.0 | 6.0 | 7.0 | 0.0 | 3.0 | 2.0 | 4.0 | 0.0 | 0.0 | 0.0 | 0.0 |
|   | 0.250 | 0.0 | 0.0 | 4.0 | 0.0 | 0.0 | 0.0 | 0.0 | 0.0 | 0.0 | 0.0 | 0.0 | 0.0 |
|   | 0.125 | 0.0 | 0.0 | 3.0 | 0.0 | 0.0 | 0.0 | 0.0 | 0.0 | 0.0 | 0.0 | 0.0 | 0.0 |
| 4 | 0.500 | 9.0 | 6.0 | 9.0 | 9.0 | 6.0 | 9.0 | 0.0 | 4.0 | 0.0 | 2.0 | 4.0 | 3.0 |
|   | 0.250 | 9.0 | 3.0 | 0.0 | 9.0 | 3.0 | 9.0 | 0.0 | 2.0 | 0.0 | 1.0 | 2.0 | 3.0 |
|   | 0.125 | 6.0 | 2.0 | 0.0 | 9.0 | 2.0 | 9.0 | 0.0 | 0.0 | 0.0 | 1.0 | 2.0 | 0.0 |
| 5 | 0.500 | 0.0 | 0.0 | 0.0 | 0.0 | 0.0 | 0.0 | 0.0 | 0.0 | 0.0 | 0.0 | 0.0 | 0.0 |
|   | 0.250 | 0.0 | 0.0 | 0.0 | 0.0 | 0.0 | 0.0 | 0.0 | 0.0 | 0.0 | 0.0 | 0.0 | 0.0 |
|   | 0.125 | 0.0 | 0.0 | 0.0 | 0.0 | 0.0 | 0.0 | 0.0 | 0.0 | 0.0 | 0.0 | 0.0 | 0.0 |
| 6 | 0.500 | 4.0 | 3.0 | 5.0 | 9.0 | 4.0 | 9.0 | 0.0 | 2.0 | 1.0 | 4.0 | 2.0 | 1.0 |
|   | 0.250 | 4.0 | 3.0 | 3.0 | 9.0 | 4.0 | 3.0 | 0.0 | 0.0 | 1.0 | 4.0 | 2.0 | 0.0 |
|   | 0.125 | 3.0 | 2.0 | 2.0 | 6.0 | 4.0 | — | 0.0 | 0.0 | 0.0 | 4.0 | 2.0 | 1.0 |
| 7 | 0.500 | 3.0 | — | 0.0 | 8.0 | 0.0 | 5.0 | 0.0 | 0.0 | 0.0 | 5.0 | 2.0 | 0.0 |
|   | 0.250 | 2.0 | 0.0 | 0.0 | 8.0 | 0.0 | 3.0 | 0.0 | 0.0 | 0.0 | 3.0 | 1.0 | 0.0 |
|   | 0.125 | 0.0 | 0.0 | 0.0 | 5.0 | 0.0 | 0.0 | 0.0 | 0.0 | 0.0 | 1.0 | 0.0 | 0.0 |
| 8 | 0.500 | 0.0 | 0.0 | 0.0 | 0.0 | 0.0 | 0.0 | 0.0 | 0.0 | 0.0 | 0.0 | 0.0 | 0.0 |
|   | 0.250 | 0.0 | 0.0 | 0.0 | 0.0 | 0.0 | 0.0 | 0.0 | 0.0 | 0.0 | 0.0 | 0.0 | 0.0 |
|   | 0.125 | 0.0 | 0.0 | 0.0 | 0.0 | 0.0 | 0.0 | 0.0 | 0.0 | 0.0 | 0.0 | 0.0 | 0.0 |
| 9 | 0.500 | 0.0 | 0.0 | 0.0 | 0.0 | 0.0 | 0.0 | 0.0 | 0.0 | 0.0 | 0.0 | 0.0 | 0.0 |
|   | 0.250 | 0.0 | 0.0 | 0.0 | 0.0 | 0.0 | 0.0 | 0.0 | 0.0 | 0.0 | 0.0 | 0.0 | 0.0 |
|   | 0.125 | 0.0 | 0.0 | 0.0 | 0.0 | 0.0 | 0.0 | 0.0 | 0.0 | 0.0 | 0.0 | 0.0 | 0.0 |
| 10 | 0.500 | 0.0 | 0.0 | 6.0 | 8.0 | 0.0 | 4.0 | 3.0 | 3.0 | 0.0 | 0.0 | 0.0 | 0.0 |
|    | 0.250 | 0.0 | 0.0 | 6.0 | 9.0 | 0.0 | 3.0 | 0.0 | 4.0 | 0.0 | 2.0 | 0.0 | 0.0 |
|    | 0.125 | — | 0.0 | 4.0 | 3.0 | 0.0 | — | 0.0 | 1.0 | 0.0 | 2.0 | 0.0 | 0.0 |
| 11 | 0.500 | 3.0 | 0.0 | 0.0 | 9.0 | 0.0 | — | 0.0 | 0.0 | 0.0 | 0.0 | 0.0 | 0.0 |
|    | 0.250 | 3.0 | 0.0 | 0.0 | 9.0 | 0.0 | — | 0.0 | 0.0 | 0.0 | 0.0 | 0.0 | 0.0 |
|    | 0.125 | 0.0 | 0.0 | 0.0 | 9.0 | 0.0 | — | 0.0 | 0.0 | 0.0 | 0.0 | 0.0 | 0.0 |
| 12 | 0.500 | 9.0 | 3.0 | 9.0 | 9.0 | 4.0 | — | 0.0 | 3.0 | 1.0 | 0.0 | 0.0 | 3.0 |
|    | 0.250 | 9.0 | 0.0 | 9.0 | 9.0 | 6.0 | — | 0.0 | 0.0 | 1.0 | 0.0 | 0.0 | 1.0 |
|    | 0.125 | 5.0 | 0.0 | 9.0 | 9.0 | 2.0 | — | 0.0 | 0.0 | 0.0 | 0.0 | 0.0 | 0.0 |
| 13 | 0.500 | 9.0 | 8.0 | 9.0 | 9.0 | 6.0 | 9.0 | 0.0 | 7.0 | 0.0 | 2.0 | 1.0 | 1.0 |
|    | 0.250 | 9.0 | 3.0 | 9.0 | 9.0 | 5.0 | 8.0 | 0.0 | 7.0 | 0.0 | 1.0 | 0.0 | 0.0 |
|    | 0.125 | 9.0 | 0.0 | 5.0 | 9.0 | 2.0 | 9.0 | 0.0 | 0.0 | 0.0 | 0.0 | 0.0 | 0.0 |
| 14 | 0.500 | 4.0 | 3.0 | 4.0 | 9.0 | 3.0 | 9.0 | 0.0 | 1.0 | 0.0 | 4.0 | 2.0 | 1.0 |
|    | 0.250 | 0.0 | 2.0 | 2.0 | 6.0 | 1.0 | 7.0 | 0.0 | 0.0 | 0.0 | 2.0 | 1.0 | 0.0 |
|    | 0.125 | 0.0 | 0.0 | 2.0 | 7.0 | 0.0 | 7.0 | 0.0 | 0.0 | 0.0 | 0.0 | 0.0 | 0.0 |
| 16 | 0.500 | 9.0 | 2.0 | 0.0 | 9.0 | 0.0 | 4.0 | 0.0 | 3.0 | 0.0 | 0.0 | 0.0 | 2.0 |
|    | 0.250 | 6.0 | 0.0 | 0.0 | 8.0 | 0.0 | 0.0 | 0.0 | 0.0 | 0.0 | 0.0 | 0.0 | 1.0 |
|    | 0.125 | 2.0 | 0.0 | 0.0 | 6.0 | 0.0 | 0.0 | 0.0 | 0.0 | 0.0 | 0.0 | 0.0 | 0.0 |
| 17 | 0.500 | 9.0 | 2.0 | 0.0 | 9.0 | 0.0 | 4.0 | 0.0 | 3.0 | 0.0 | 2.0 | 0.0 | 3.0 |
|    | 0.250 | 3.0 | 0.0 | 0.0 | 9.0 | 0.0 | 7.0 | 0.0 | 0.0 | 0.0 | 0.0 | 0.0 | 0.0 |
|    | 0.125 | 0.0 | 0.0 | 0.0 | 6.0 | 0.0 | 0.0 | 0.0 | 0.0 | 0.0 | 0.0 | 0.0 | 0.0 |
| 18 | 0.500 | 0.0 | 0.0 | 0.0 | 7.0 | 4.0 | 4.0 | 0.0 | 0.0 | 0.0 | 0.0 | 0.0 | 0.0 |
|    | 0.250 | 0.0 | 0.0 | 0.0 | 5.0 | 0.0 | 0.0 | 0.0 | 0.0 | 0.0 | 0.0 | 0.0 | 0.0 |
|    | 0.125 | 0.0 | 0.0 | 0.0 | 0.0 | 0.0 | 0.0 | 0.0 | 0.0 | 0.0 | 0.0 | 0.0 | 0.0 |

We claim:

1. A process for the preparation of a compound having the structural formula

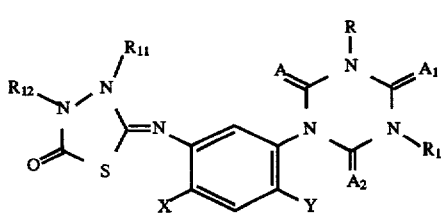

wherein m is an integer of 0, 1 or 2;

$R_2$ is $C_1-C_4$alkyl or $C_1-C_4$haloalkyl;

R is hydrogen, $C_1-C_6$alkyl, $C_2-C_{12}$alkoxyalkyl, $C_3-C_{12}$alkylcarbonylalkyl, $C_3-C_{12}$haloalkylcarbonylalkyl, $C_3-C_{12}$alkoxycarbonylalkyl, $C_3-C_{12}$haloalkoxycarbonylalkyl, $C_3-C_6$alkenyl, $C_3-C_6$alkynyl, phenyl optionally substituted with one to three halogen, $C_1-C_4$alkyl, $C_1-C_4$alkoxy or $C_1-C_4$haloalkoxy groups, or benzyl optionally substituted with one to three halogen, $C_1$–$C_4$alkyl, $C_1$–$C_4$alkoxy or $C_1$–$C_4$haloalkoxy groups;

$R_1$ is hydrogen, $C_3$–$C_6$alkenyl, $C_3$–$C_6$alkynyl, cyano, $C_1$–$C_{12}$alkyl optionally substituted with one or more halogen atoms, or one cyano, $C(O)R_3$, $OC(O)R_5$, $CH_2OC(O)R_5$, $OR_4$, $CH_2OR_4$ or $CR_6(OR_7)_2$ group, or one phenyl group optionally substituted with one to three halogen, $C_1$–$C_4$alkyl, $C_1$–$C_4$alkoxy or $C_1$–$C_4$haloalkoxy groups, or phenyl optionally substituted with one to three halogen, $C_1$–$C_4$alkyl, $C_1$–$C_4$alkoxy, or $C_1$–$C_4$haloalkoxy groups;

$R_3$ is $OR_8$, $SR_8$ or $NR_9R_{10}$;

$R_4$, $R_5$ and $R_6$ are each independently hydrogen, $C_1$–$C_4$alkyl or $C_1$–$C_4$haloalkyl;

$R_7$ is $C_1$–$C_4$alkyl;

$R_8$ is $C_1$–$C_6$alkyl optionally substituted with $C_1$–$C_4$alkoxy, $C_1$–$C_4$alkylthio, halogen, hydroxy, $C_3$–$C_6$cycloalkyl, furyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups, $C_3$–$C_6$alkenyl optionally substituted with $C_1$–$C_4$alkoxy, halogen, $C_3$–$C_6$cycloalkyl or phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups, $C_3$–$C_6$alkynyl optionally substituted with $C_1$–$C_4$alkoxy or halogen, or $C_3$–$C_6$cycloalkyl;

$R_9$ and $R_{10}$ are each independently hydrogen, $C_1$–$C_6$alkyl, benzyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups, or phenyl optionally substituted with one or more halogen, cyano, nitro, $C_1$–$C_4$alkyl, $C_1$–$C_4$haloalkyl, $C_1$–$C_4$alkoxy or $C_1$–$C_4$haloalkoxy groups;

$R_{11}$ and $R_{12}$ are each independently hydrogen, $C_1$–$C_6$alkyl optionally substituted with one or more halogen atoms, or $C_3$–$C_6$cycloalkyl optionally substituted with one or more halogen atoms, and when $R_{11}$ and $R_{12}$ are taken together with the atoms to which they are attached, they represent a four- to seven-membered saturated or unsaturated ring optionally interrupted by O, S(O)$_r$ or N, and optionally substituted with one to three methyl groups or one or more halogen atoms;

A, $A_1$ and $A_2$ are each independently O or S; and r is an integer of 0, 1 or 2, which process comprises reacting an isothiocyanate having the structural formula

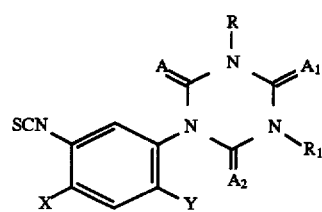

wherein X, Y, R, $R_1$, A, $A_1$ and $A_2$ are as described above with a hydrazine having the structural formula $R_{12}NHNHR_{11}$ wherein $R_{11}$ and $R_{12}$ are as described above to form an intermediate compound, having the structural formula

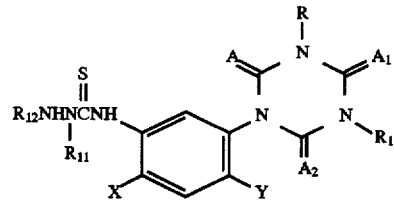

wherein X, Y, R, $R_1$, $R_{11}$, $R_{12}$, A, $A_1$ and $A_2$ are as described above, and reacting the intermediate compound with phosgene or a phosgene equivalent in the presence of a base.

2. The process according to claim 1 wherein

X is hydrogen or halogen;

Y is hydrogen, halogen, nitro or cyano;

R is hydrogen, $C_1$–$C_4$alkyl, $C_1$–$C_4$alkoxymethyl, ($C_1$–$C_4$alkoxy) carbonylmethyl, $C_3$–$C_6$alkenyl or $C_3$–$C_6$alkynyl;

$R_1$ is hydrogen, $C_3$–$C_6$alkenyl, $C_3$–$C_6$alkynyl or $C_1$–$C_6$alkyl optionally substituted with one $CO_2R_8$ group;

$R_8$ is $C_1$–$C_6$alkyl;

$R_{11}$ and $R_{12}$ are taken together with the atoms to which they are attached to form a ring in which $R_{11}R_{12}$ is a $C_2$–$C_5$alkylene group optionally interrupted by S(O)$_r$ and optionally substituted with one to three methyl groups or one or more halogen atoms, or $R_{11}R_{12}$ is represented by the structure: —$CR_{18}$=$CR_{19}$—$CR_{20}$=$CR_{21}$— where $R_{18}$, $R_{19}$, $R_{20}$ and $R_{21}$ are each independently hydrogen, halogen or methyl;

A, $A_1$ and $A_2$ are O; and r is an integer of 0, 1 or 2.

3. The process according to claim 1 wherein the intermediate compound is reacted with phosgene in the presence of a base.

* * * * *